US011690746B2

(12) United States Patent
Bushby

(10) Patent No.: US 11,690,746 B2
(45) Date of Patent: *Jul. 4, 2023

(54) PRE-CUT ADHESIVE SUPPORTS FOR ANATOMICAL SUPPORT, PAIN REDUCTION, OR THERAPEUTIC TREATMENT

(71) Applicant: Applied BioKinetics LLC, Spring, TX (US)

(72) Inventor: Donald P. Bushby, Spring, TX (US)

(73) Assignee: Applied BioKinetics LLC, Spring, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/384,503

(22) Filed: Jul. 23, 2021

(65) Prior Publication Data

US 2021/0346185 A1 Nov. 11, 2021
US 2022/0346999 A9 Nov. 3, 2022

Related U.S. Application Data

(63) Continuation of application No. 16/387,250, filed on Apr. 17, 2019, now Pat. No. 11,096,815, which is a (Continued)

(51) Int. Cl.
*A43B 7/14* (2022.01)
*A61F 5/01* (2006.01)
(Continued)

(52) U.S. Cl.
CPC ............ *A61F 5/0111* (2013.01); *A43B 7/141* (2013.01); *A43B 7/142* (2013.01); *A43B 7/143* (2013.01);
(Continued)

(58) Field of Classification Search
CPC ........ A61F 5/01; A61F 5/0111; A61F 13/067; A61F 2013/00246; A61F 2013/0091;
(Continued)

(56) References Cited

U.S. PATENT DOCUMENTS 825,050 A 7/1906 Hammer
861,348 A 7/1907 Baltz
(Continued)

FOREIGN PATENT DOCUMENTS

AU 5789894 A 10/1994
AU 673228 10/1996
(Continued)

OTHER PUBLICATIONS

U.S. Appl. No. 15/240,783, Notice of Allowance dated Mar. 26, 2019.
(Continued)

*Primary Examiner* — Tarla R Patel
(74) *Attorney, Agent, or Firm* — Brian F. Russell

(57) ABSTRACT

An elongate strap support system for anatomical support, pain reduction, or therapeutic treatment includes a package containing a first elongate strap support and at least one additional elongate strap support. In one example, the first elongate strap support includes a woven fabric support layer including synthetic fibers. The woven fabric is shaped so as to form an elongated strap with rounded portions. The woven fabric is substantially resistant to stretching in one direction under such test conditions as those specified in ASTM D3759. The first elongate strap support additionally includes an adhesive layer on the support layer for adhesive attachment of the woven fabric support layer to an outer skin surface of a body and a removable cover layer on the adhesive layer.

66 Claims, 27 Drawing Sheets

Related U.S. Application Data continuation of application No. 15/240,783, filed on Aug. 18, 2016, now Pat. No. 10,299,953, which is a continuation of application No. 13/783,632, filed on Mar. 4, 2013, now Pat. No. 10,212,987, which is a continuation of application No. 13/477,015, filed on May 21, 2012, now Pat. No. 8,834,397, which is a continuation of application No. 11/165,304, filed on Jun. 23, 2005, now Pat. No. 8,216,162, and a continuation-in-part of application No. 10/817,172, filed on Apr. 2, 2004, now Pat. No. 8,414,511.

(51) Int. Cl.

| | | |
|---|---|---|
| *B32B 3/02* | (2006.01) | |
| *B32B 3/26* | (2006.01) | |
| *B32B 5/02* | (2006.01) | |
| *B32B 7/06* | (2019.01) | |
| *B32B 7/12* | (2006.01) | |
| *A61F 13/00* | (2006.01) | |
| *A61F 13/06* | (2006.01) | |
| *B32B 27/06* | (2006.01) | |
| *A61F 5/00* | (2006.01) | |
| *B29D 11/00* | (2006.01) | |
| *A43B 13/34* | (2006.01) | |
| *A43B 7/1405* | (2022.01) | |
| *A43B 7/142* | (2022.01) | |
| *A43B 7/1425* | (2022.01) | |
| *A43B 7/143* | (2022.01) | |
| *A43B 7/1435* | (2022.01) | |
| *A43B 7/144* | (2022.01) | |
| *A43B 7/1445* | (2022.01) | |
| *A43B 7/145* | (2022.01) | |

(52) U.S. Cl.
CPC .............. *A43B 7/144* (2013.01); *A43B 7/145* (2013.01); *A43B 7/1425* (2013.01); *A43B 7/1435* (2013.01); *A43B 7/1445* (2013.01); *A43B 7/1495* (2013.01); *A61F 13/067* (2013.01); *B32B 3/02* (2013.01); *B32B 3/266* (2013.01); *B32B 5/022* (2013.01); *B32B 5/024* (2013.01); *B32B 7/06* (2013.01); *B32B 7/12* (2013.01); *B32B 27/06* (2013.01); *A61F 2013/0028* (2013.01); *A61F 2013/0091* (2013.01); *A61F 2013/00246* (2013.01); *A61F 2013/00272* (2013.01); *B32B 2255/02* (2013.01); *B32B 2262/04* (2013.01); *B32B 2307/54* (2013.01); *B32B 2307/724* (2013.01); *B32B 2307/732* (2013.01); *B32B 2307/744* (2013.01); *B32B 2307/748* (2013.01); *B32B 2405/00* (2013.01); *B32B 2535/00* (2013.01)

(58) Field of Classification Search
CPC ... A61F 2013/0028; A61F 2013/00272; A43B 7/14; A43B 23/02; A43B 21/24; A43B 7/28; A43B 7/143; A43B 7/142; A43B 7/1445; A43B 7/145; A43B 7/1425; A43B 7/144; A43B 7/1495; A43B 7/141; A43B 7/1435; B32B 5/022; B32B 5/024; B32B 7/06; B32B 7/12; B32B 27/06; B32B 3/02; B32B 3/266; B32B 2262/04; B32B 2255/02; B32B 2307/724; B32B 2307/732; B32B 2307/744; B32B 2307/748; B32B 2405/00; B32B 2535/00; B32B 2307/54
USPC ....... 602/1, 28, 29; 36/140, 43, 44; 706/924, 706/932, 934; 704/270; 206/363, 438, 206/440, 441, 828; 423/111, 108–118
See application file for complete search history.

(56) References Cited

U.S. PATENT DOCUMENTS

| | | |
|---|---|---|
| 866,934 A | 9/1907 | Katz |
| 1,351,248 A | 8/1920 | Hill |
| 1,441,708 A | 1/1923 | Overbury |
| 1,492,514 A | 4/1924 | Harris |
| 1,566,063 A | 12/1925 | Barry |
| 1,577,203 A | 3/1926 | Cramer |
| 1,717,609 A | 6/1929 | Ludwig |
| 1,788,852 A | 1/1931 | Arthur |
| 1,980,621 A | 11/1934 | Innis |
| 2,013,757 A | 9/1935 | Jung, Jr. |
| 2,182,843 A | 12/1939 | Flynn et al. |
| 2,310,082 A | 2/1943 | Holbrooke |
| 2,312,378 A | 3/1943 | Baum |
| 2,349,709 A | 5/1944 | Evans |
| 2,358,966 A | 9/1944 | Einstoss |
| 2,399,545 A | 4/1946 | Davis |
| 2,410,078 A | 10/1946 | Waldo |
| 2,454,836 A | 11/1948 | Rayner |
| 2,508,855 A | 5/1950 | Brown |
| 2,544,315 A | 3/1951 | Heldmann |
| 2,572,152 A | 10/1951 | Horlacher |
| 2,633,130 A | 3/1953 | Scholl |
| 2,646,040 A | 7/1953 | Stanton |
| 2,729,193 A | 1/1956 | Scholl |
| 2,940,591 A | 6/1960 | Swedish et al. |
| 2,940,868 A | 6/1960 | Patchell |
| 2,961,348 A | 11/1960 | Finnegan et al. |
| 2,963,386 A | 12/1960 | Weschler et al. |
| 2,985,970 A | 5/1961 | McCarthy |
| 3,038,295 A | 6/1962 | Humphreys |
| 3,050,053 A | 8/1962 | Peckham |
| 3,053,253 A | 9/1962 | Liloia et al. |
| 3,073,303 A | 1/1963 | Schaar |
| 3,089,786 A | 5/1963 | Nachtsheim et al. |
| 3,143,208 A | 8/1964 | Sizemore, Jr. |
| 3,199,548 A | 8/1965 | Conant |
| 3,282,727 A | 11/1966 | Crone et al. |
| 3,312,219 A | 4/1967 | Peckham |
| 3,327,410 A | 6/1967 | Park et al. |
| 3,342,028 A | 9/1967 | Matsubayashi et al. |
| 3,355,974 A | 12/1967 | Carmichael |
| 3,357,425 A | 12/1967 | Morgan |
| 3,364,063 A | 1/1968 | Donatas |
| 3,387,451 A | 6/1968 | Cape et al. |
| 3,425,412 A | 2/1969 | Pope |
| 3,449,844 A | 6/1969 | Spence |
| 3,457,919 A | 7/1969 | Harbard |
| 3,482,683 A | 12/1969 | Desnoyers |
| 3,508,544 A | 4/1970 | Moore et al. |
| 3,530,494 A | 9/1970 | Baratta |
| 3,584,622 A | 6/1971 | Domenico |
| 3,618,754 A | 11/1971 | Hoey |
| 3,716,132 A | 2/1973 | Lewyckyj |
| 3,794,038 A | 2/1974 | Buell |
| 3,811,438 A | 5/1974 | Economou |
| 3,849,332 A | 11/1974 | Bailey et al. |
| 3,853,598 A | 12/1974 | Raguse |
| 3,926,186 A | 12/1975 | Nirschl |
| 3,965,786 A | 6/1976 | D'Luhy |
| 3,973,563 A | 8/1976 | Green et al. |
| 3,989,041 A | 11/1976 | Davies |
| 3,991,754 A | 11/1976 | Gertzman |
| 4,136,686 A | 1/1979 | Arluck |
| 4,215,687 A | 8/1980 | Shaw |
| 4,271,605 A | 6/1981 | Raczka |
| 4,292,360 A | 9/1981 | Riedel et al. |
| 4,345,590 A | 8/1982 | Nakajima |
| 4,355,720 A | 10/1982 | Hofberg et al. |
| 4,366,814 A | 1/1983 | Riedel |
| 4,373,519 A | 2/1983 | Errede et al. |
| 4,377,160 A | 3/1983 | Romaine |
| 4,392,487 A | 7/1983 | Selmer et al. |
| 4,428,809 A | 1/1984 | Heimbach et al. |
| 4,510,699 A | 4/1985 | Nakamura et al. |
| 4,588,871 A | 5/1986 | Etcheparre et al. |

(56) References Cited

U.S. PATENT DOCUMENTS

| | | | |
|---|---|---|---|
| 4,638,796 A | 1/1987 | Sims | |
| 4,654,254 A | 3/1987 | Gerry et al. | |
| 4,696,289 A | 9/1987 | Gardner et al. | |
| 4,702,948 A | 10/1987 | Sieber-Gadient | |
| 4,734,320 A | 3/1988 | Ohira et al. | |
| 4,735,342 A | 4/1988 | Goldstein | |
| 4,751,784 A | 6/1988 | Petker et al. | |
| 4,753,228 A | 6/1988 | Selmer et al. | |
| 4,782,196 A | 11/1988 | Ukai | |
| 4,801,494 A | 1/1989 | Datta et al. | |
| 4,807,753 A | 2/1989 | Goldstein | |
| 4,860,464 A | 8/1989 | Misevich et al. | |
| 4,875,476 A | 10/1989 | Garcia | |
| 4,984,566 A | 1/1991 | Sekine et al. | |
| 4,997,709 A | 3/1991 | Huddleson et al. | |
| 5,133,477 A | 7/1992 | Etheredge, III et al. | |
| 5,154,690 A | 10/1992 | Shiono | |
| 5,167,995 A | 12/1992 | Johnson et al. | |
| 5,203,793 A | 4/1993 | Lyden | |
| 5,230,701 A | 7/1993 | Meyer et al. | |
| 5,240,775 A | 8/1993 | Tannenbaum | |
| 5,256,134 A | 10/1993 | Ingham | |
| 5,382,445 A | 1/1995 | Yasis | |
| 5,397,298 A | 3/1995 | Mazza et al. | |
| 5,449,550 A | 9/1995 | Yasis et al. | |
| 5,453,083 A | 9/1995 | Kasahara | |
| 5,460,601 A | 10/1995 | Shannahan | |
| 5,473,781 A | 12/1995 | Greenberg | |
| 5,474,522 A | 12/1995 | Scholz et al. | |
| 5,488,889 A | 2/1996 | Kang | |
| 5,496,605 A | 3/1996 | Augst et al. | |
| 5,503,908 A | 4/1996 | Faass | |
| 5,505,692 A | 4/1996 | Cho | |
| 5,537,905 A | 7/1996 | Zimmer et al. | |
| 5,540,982 A | 7/1996 | Scholz et al. | |
| 5,559,165 A | 9/1996 | Paul | |
| 5,590,785 A | 1/1997 | Seitzinger | |
| 5,613,964 A | 3/1997 | Grenier | |
| 5,616,387 A | 4/1997 | Augst et al. | |
| 5,620,413 A | 4/1997 | Olson | |
| 5,681,301 A | 10/1997 | Yang et al. | |
| 5,711,312 A | 1/1998 | Staudinger | |
| 5,725,487 A | 3/1998 | Freeman et al. | |
| 5,755,681 A | 5/1998 | Plews | |
| 5,762,623 A | 6/1998 | Murphy et al. | |
| 5,772,621 A | 6/1998 | Unruh | |
| 5,782,496 A | 7/1998 | Casper et al. | |
| 5,782,786 A | 7/1998 | Tomaiuolo | |
| 5,792,091 A | 8/1998 | Staudinger | |
| 5,795,834 A | 8/1998 | Deeb et al. | |
| 5,807,368 A | 9/1998 | Helmer | |
| 5,840,053 A | 11/1998 | Roth | |
| 5,861,348 A | 1/1999 | Kase | |
| 5,865,779 A | 2/1999 | Gleason | |
| 5,891,078 A | 4/1999 | Turngren et al. | |
| 5,897,518 A | 4/1999 | Shaw | |
| 5,931,798 A | 8/1999 | Green et al. | |
| 5,938,631 A | 8/1999 | Colman | |
| 5,957,871 A | 9/1999 | Darcey | |
| 5,973,221 A | 10/1999 | Collyer et al. | |
| 5,981,823 A | 11/1999 | Turngren | |
| 5,992,055 A | 11/1999 | Connor | |
| 6,007,468 A | 12/1999 | Giacometti | |
| 6,048,806 A | 4/2000 | Deeb et al. | |
| 6,074,354 A | 6/2000 | Scholz et al. | |
| 6,074,965 A | 6/2000 | Bodenschatz et al. | |
| 6,090,076 A | 7/2000 | Lane | |
| 6,107,219 A | 8/2000 | Joseph et al. | |
| 6,120,470 A | 9/2000 | Bodenschatz et al. | |
| 6,120,473 A | 9/2000 | Oliverio | |
| 6,133,173 A | 10/2000 | Riedel et al. | |
| 6,146,344 A | 11/2000 | Bader | |
| 6,159,173 A | 12/2000 | Morales | |
| 6,213,343 B1 | 4/2001 | Damikolas | |
| 6,261,252 B1 | 7/2001 | Darcey | |
| 6,262,330 B1 | 7/2001 | Fujisawa et al. | |
| 6,297,421 B1 | 10/2001 | Kitazaki et al. | |
| 6,302,867 B1 | 10/2001 | Brown, Jr. et al. | |
| 6,315,749 B1 | 11/2001 | Sunayama | |
| 6,358,220 B1 | 3/2002 | Langen et al. | |
| 6,387,973 B1 | 5/2002 | Saleh et al. | |
| 6,410,464 B1 | 6/2002 | Menzies et al. | |
| 6,422,848 B1 | 7/2002 | Allen et al. | |
| 6,436,020 B1 | 8/2002 | Weingand | |
| 6,436,528 B1 | 8/2002 | Külper et al. | |
| 6,447,470 B2 | 9/2002 | Bodenschatz et al. | |
| 6,485,448 B2 | 11/2002 | Lamping et al. | |
| 6,503,855 B1 | 1/2003 | Menzies et al. | |
| 6,558,339 B1 | 5/2003 | Graham | |
| 6,573,419 B2 | 6/2003 | Naimer | |
| 6,632,522 B1 | 10/2003 | Hyde et al. | |
| 6,635,334 B1 | 10/2003 | Jackson et al. | |
| 6,640,465 B1 | 11/2003 | Burgess | |
| 6,641,550 B1 | 11/2003 | Johnson | |
| 6,676,619 B2 | 1/2004 | Arden | |
| 6,684,442 B1 | 2/2004 | Parker et al. | |
| 6,699,209 B2 | 3/2004 | Turtzo | |
| 6,756,519 B2 | 6/2004 | Johnson et al. | |
| 6,775,929 B2 | 8/2004 | Katz et al. | |
| 6,849,057 B2 | 2/2005 | Satou et al. | |
| 6,886,276 B2 | 5/2005 | Hlavac | |
| 6,894,204 B2 | 5/2005 | Dunshee | |
| 6,901,712 B2 | 6/2005 | Lionel | |
| 6,929,613 B2 | 8/2005 | Henderson et al. | |
| 6,953,620 B2 | 10/2005 | Schneider et al. | |
| 6,991,610 B2 | 1/2006 | Matsumoto et al. | |
| 7,041,075 B2 | 5/2006 | Sullivan | |
| 7,082,703 B2 | 8/2006 | Greene et al. | |
| 7,107,705 B2 | 9/2006 | Dalton et al. | |
| 7,115,106 B2 | 10/2006 | Bodenschatz et al. | |
| 7,138,169 B2 | 11/2006 | Shiota et al. | |
| 7,146,893 B2 | 12/2006 | Aichele | |
| 7,173,161 B1 | 2/2007 | Kandt | |
| 7,195,605 B1 | 3/2007 | White | |
| 7,396,338 B2 | 7/2008 | Huber et al. | |
| 7,419,476 B2 | 9/2008 | Oohira et al. | |
| 7,430,820 B2 | 10/2008 | Andreoli et al. | |
| 7,465,284 B2 | 12/2008 | Huppert | |
| 7,498,477 B2 | 3/2009 | Wada et al. | |
| 7,568,580 B2 | 8/2009 | Fenton | |
| 7,594,461 B2 | 9/2009 | Aichele et al. | |
| 7,753,864 B2 | 7/2010 | Beckwith et al. | |
| 7,780,612 B2 | 8/2010 | Ross | |
| 7,886,776 B2 | 2/2011 | Jung et al. | |
| 7,902,420 B2 | 3/2011 | Kase | |
| 7,914,476 B2 | 3/2011 | Ball et al. | |
| 7,942,838 B2 | 5/2011 | Farrow | |
| 8,105,450 B2 | 1/2012 | Stelter et al. | |
| 8,216,162 B2 * | 7/2012 | Bushby | A61F 5/0127 602/61 |
| 8,216,415 B2 | 7/2012 | Quinn | |
| 8,414,511 B2 * | 4/2013 | Bushby | A43B 7/145 602/61 |
| 8,486,524 B2 | 7/2013 | Kishioka et al. | |
| 8,506,508 B2 | 8/2013 | Avitable et al. | |
| 8,742,196 B2 | 6/2014 | Arbesman et al. | |
| 8,814,818 B2 * | 8/2014 | Bushby | A61F 5/0111 523/108 |
| 8,834,397 B2 * | 9/2014 | Bushby | B65B 5/10 523/108 |
| 8,834,398 B2 | 9/2014 | Bushby | |
| 8,968,229 B2 | 3/2015 | Bushby | |
| 9,039,643 B2 | 5/2015 | Bolla | |
| 9,200,390 B2 | 12/2015 | Kimura et al. | |
| 9,228,859 B2 | 1/2016 | Ranky et al. | |
| 9,279,069 B2 | 3/2016 | Takahashi et al. | |
| 9,308,115 B2 | 4/2016 | Quinn | |
| 9,376,824 B2 | 6/2016 | Neill et al. | |
| 10,159,606 B2 | 12/2018 | Murphy et al. | |
| 10,212,987 B2 | 2/2019 | Bushby | |
| 10,299,953 B2 * | 5/2019 | Bushby | A43B 7/1435 |
| 11,096,815 B2 * | 8/2021 | Bushby | B32B 5/022 |
| 11,206,894 B2 * | 12/2021 | Bushby | B26D 3/10 |
| 2002/0040202 A1 | 4/2002 | Levin | |

(56) References Cited

U.S. PATENT DOCUMENTS

| | | |
|---|---|---|
| 2002/0062097 A1 | 5/2002 | Simpson |
| 2002/0099318 A1 | 7/2002 | Suehr et al. |
| 2002/0162250 A1 | 11/2002 | Campbell et al. |
| 2002/0165477 A1 | 11/2002 | Dunshee |
| 2002/0177797 A1 | 11/2002 | Henderson et al. |
| 2002/0183671 A1 | 12/2002 | Henderson et al. |
| 2002/0188239 A1 | 12/2002 | Turtzo |
| 2002/0193718 A1 | 12/2002 | Henderson et al. |
| 2002/0193724 A1 | 12/2002 | Stebbings et al. |
| 2003/0069530 A1 | 4/2003 | Satou et al. |
| 2003/0138479 A1 | 7/2003 | Mizota et al. |
| 2003/0145495 A1 | 8/2003 | Green |
| 2003/0171707 A1 | 9/2003 | Bodenschatz et al. |
| 2003/0183053 A1 | 10/2003 | Amend et al. |
| 2003/0212358 A1 | 11/2003 | Cavanagh et al. |
| 2004/0006814 A1 | 1/2004 | Holden |
| 2004/0118017 A1 | 6/2004 | Dalton et al. |
| 2004/0118020 A1 | 6/2004 | Hlavac |
| 2004/0175527 A1 | 9/2004 | Shiota et al. |
| 2004/0261294 A1 | 12/2004 | Kawata |
| 2005/0011084 A1 | 1/2005 | Stephenson |
| 2005/0042269 A1 | 2/2005 | Tateishi et al. |
| 2005/0131324 A1 | 6/2005 | Bledsoe |
| 2005/0240139 A1 | 10/2005 | Bushby |
| 2005/0251073 A1 | 11/2005 | Roth |
| 2006/0065098 A1 | 3/2006 | Cranna |
| 2006/0089585 A1 | 4/2006 | Takemura et al. |
| 2006/0147667 A1 | 7/2006 | Salmon |
| 2006/0154546 A1 | 7/2006 | Murphy et al. |
| 2007/0010777 A1 | 1/2007 | Dunshee et al. |
| 2007/0082023 A1 | 4/2007 | Hopman et al. |
| 2007/0141937 A1 | 6/2007 | Hendrix et al. |
| 2007/0184735 A1 | 8/2007 | Yun et al. |
| 2007/0212520 A1 | 9/2007 | Furumori et al. |
| 2007/0259163 A1 | 11/2007 | Connolly et al. |
| 2007/0283597 A1 | 12/2007 | Logan |
| 2008/0076310 A1 | 3/2008 | Kishioka et al. |
| 2008/0154169 A1 | 6/2008 | Kase |
| 2008/0280518 A1 | 11/2008 | Takahashi et al. |
| 2008/0299855 A1 | 12/2008 | Morihashi |
| 2009/0075052 A1 | 3/2009 | Hopf |
| 2009/0192256 A1 | 7/2009 | Lin |
| 2010/0016771 A1 | 1/2010 | Arbesman et al. |
| 2010/0087116 A1 | 4/2010 | Takahashi et al. |
| 2010/0098846 A1 | 4/2010 | Ding et al. |
| 2010/0191163 A1 | 7/2010 | Dennis et al. |
| 2010/0277102 A1 | 9/2010 | Keener et al. |
| 2010/0298747 A1 | 11/2010 | Quinn |
| 2011/0056621 A1 | 3/2011 | Quinn |
| 2011/0059281 A1 | 3/2011 | Wada |
| 2011/0208101 A1 | 8/2011 | Keller et al. |
| 2011/0245749 A1 | 10/2011 | Kikuta et al. |
| 2011/0271854 A1 | 11/2011 | Quinn |
| 2012/0109031 A1 | 5/2012 | Vollbrecht et al. |
| 2012/0232452 A1 | 9/2012 | Bushby |
| 2012/0301660 A1 | 11/2012 | Bartusiak |
| 2015/0005687 A1 | 1/2015 | Bushby |
| 2015/0018741 A1 | 1/2015 | Lieberson et al. |

FOREIGN PATENT DOCUMENTS

| | | |
|---|---|---|
| AU | 673228 B2 | 10/1996 |
| CA | 2041576 C | 8/2001 |
| CA | 2202296 C | 10/2002 |
| DE | 825448 C | 12/1951 |
| DE | 2356950 A1 | 5/1975 |
| DE | 19950509 C1 | 11/2001 |
| DE | 20018575 U1 | 3/2002 |
| DE | 20018575 U1 | 4/2002 |
| DE | 10357231 A1 | 7/2005 |
| EP | 0478784 A1 | 4/1992 |
| EP | 0621023 A2 | 10/1994 |
| EP | 1097975 | 5/2001 |
| EP | 1097975 A3 | 6/2001 |
| FR | 791796 A | 12/1935 |
| FR | 791796 A | 12/1935 |
| FR | 2697156 A1 | 4/1994 |
| FR | 2697156 A1 | 4/1994 |
| FR | 2896808 A1 | 8/2007 |
| GB | 825050 A | 12/1959 |
| GB | 866934 A | 5/1961 |
| JP | 08131477 | 5/1996 |
| JP | H08131477 | 5/1996 |
| JP | 10033741 A | 2/1998 |
| JP | H1033741 A | 2/1998 |
| JP | H11199835 A | 7/1999 |
| JP | 2000220685 A | 8/2000 |
| JP | 2000245771 A | 9/2000 |
| JP | 2000245771 A | 9/2000 |
| JP | 3100300 B2 | 10/2000 |
| JP | 2000328025 A | 11/2000 |
| JP | 2001000463 A | 1/2001 |
| JP | 2001000463 A | 1/2001 |
| JP | 2001008961 A | 1/2001 |
| JP | 2001008961 A | 1/2001 |
| JP | 2001104366 A | 4/2001 |
| JP | 2001104366 A | 4/2001 |
| JP | 2001115680 A | 4/2001 |
| JP | 2002035196 A | 2/2002 |
| JP | 2002035196 A | 2/2002 |
| JP | 2002105703 A | 4/2002 |
| JP | 2002177319 A | 6/2002 |
| JP | 2002177319 A | 6/2002 |
| JP | 2002209931 A | 7/2002 |
| JP | 2002306529 A | 10/2002 |
| JP | 2002306529 A | 10/2002 |
| JP | 2003164484 A | 6/2003 |
| JP | 2003164484 A | 6/2003 |
| JP | 2003329413 A | 11/2003 |
| JP | 2004248842 A | 9/2004 |
| JP | 2004305533 A | 11/2004 |
| JP | 2004305533 A | 11/2004 |
| JP | 2004305540 A | 11/2004 |
| JP | 2004305540 A | 11/2004 |
| JP | 2005095203 A | 1/2005 |
| JP | 2005095203 A | 4/2005 |
| JP | 2003105158 A5 | 6/2005 |
| JP | 2005152402 A | 6/2005 |
| JP | 2008136656 | 6/2008 |
| KR | 20040048672 A | 6/2004 |
| TW | 459080 B | 10/2001 |
| WO | 8001758 | 9/1980 |
| WO | 9402091 A1 | 2/1994 |
| WO | 9613995 A1 | 5/1996 |
| WO | 9624316 | 8/1996 |
| WO | 9624316 A1 | 8/1996 |
| WO | 9965433 A1 | 12/1999 |
| WO | 0029225 | 5/2000 |
| WO | 0029225 A1 | 5/2000 |
| WO | 2002000052 A1 | 1/2002 |
| WO | 0243517 | 6/2002 |
| WO | 0243518 | 6/2002 |
| WO | 0243519 | 6/2002 |
| WO | 02072162 A3 | 5/2003 |
| WO | 2006067876 | 6/2006 |

OTHER PUBLICATIONS

U.S. Appl. No. 10/817,172, Non-Final Office Action dated Dec. 1, 2006.
U.S. Appl. No. 10/817,172, Final Office Action dated May 7, 2007.
U.S. Appl. No. 10/817,172, Non-Final Office Action dated Sep. 10, 2007.
U.S. Appl. No. 10/817,172, Final Office Action dated Apr. 16, 2008.
U.S. Appl. No. 10/817,172, Non-Final Office Action dated Sep. 23, 2008.
U.S. Appl. No. 10/817,172, Final Office Action dated Jun. 25, 2009.
U.S. Appl. No. 10/817,172, Non-Final Office Action dated Aug. 4, 2009.
U.S. Appl. No. 10/817,172, Pre-Brief Appeal Conference Decision dated Nov. 23, 2009.
U.S. Appl. No. 10/817,172, Examiners Answer to Appeal Brief dated Apr. 26, 2010.

(56) References Cited

OTHER PUBLICATIONS

U.S. Appl. No. 10/817,172, Patent Board Decision dated Oct. 16, 2012.
U.S. Appl. No. 10/817,172, Notice of Allowance dated Jan. 30, 2013.
U.S. Appl. No. 13/477,025, Notice of Allowance dated Aug. 13, 2014.
U.S. Appl. No. 13/477,015, Notice of Allowance dated Aug. 6, 2014.
U.S. Appl. No. 13/602,150, Notice of Allowance dated Dec. 22, 2014.
U.S. Appl. No. 11/165,304, Non-Final Office Action dated Sep. 17, 2008.
U.S. Appl. No. 11/165,304, Final Office Action dated Aug. 4, 2009.
U.S. Appl. No. 11/165,304, Non-Final Office Action dated Jan. 21, 2010.
U.S. Appl. No. 11/165,304, Final Office Action dated Aug. 5, 2010.
U.S. Appl. No. 11/165,304, Notice of Allowance dated Apr. 26, 2012.
U.S. Appl. No. 13/365,237, Notice of Allowance dated Jul. 22, 2014.
U.S. Appl. No. 13/783,632, Non-Final Office Action dated Aug. 6, 2015.
U.S. Appl. No. 13/783,632, Final Office Action dated Apr. 6, 2016.
U.S. Appl. No. 13/783,632, Non-Final Office Action dated Oct. 6, 2016.
U.S. Appl. No. 13/783,632, Final Office Action dated Mar. 22, 2017.
U.S. Appl. No. 13/783,632, Advisory Action dated May 18, 2017.
U.S. Appl. No. 13/783,632, Examiner's Answer dated Sep. 28, 2017.
U.S. Appl. No. 13/783,632, Decision on Appeal dated Sep. 20, 2018.
U.S. Appl. No. 13/783,632, Notice of Allowance dated Jan. 9, 2019.
Supplemental European Search Report from EPO, App No. EP12814131 dated Mar. 12, 2015.
Office Action from U.S. Appl. No. 13/188,319 dated Dec. 11, 2014.
Office Action from, Canadian Patent Application No. 2845061 dated Feb. 16, 2015.
Office Action from Korean Patent Application No. 10-2014-7004559 dated Jan. 6, 2015.
International Search Report and Written Opinion dated Sep. 22, 2005.
Schulthies et al.; A Modified Low-Dye Taping Technique to Support the Medial Longitudinal Arch and Reduce Excessive Pronation; J Anti Train; 30(3):266-268; Sep. 1995.
Dreamy Feet Co.; Adhesive Paddings (product info ); 9 pgs.; downloaded Mar. 3, 2005 from the internet: (http://www.dreamyfeet.co.uk/adhesive_padding.htm).
My Foot Shop; Plantar Fasciitis (information); © 2001; 10 pgs.; downloaded Sep. 11, 2008 from the internet: (httpllweb.archive.org/web/20030709195412/myfootshop.comldetail.asp?Condition=Plant).
Sports Injury Clinic; Taping for Plantar Fasciitis (instructions); 2 pgs.; downloaded Mar. 10, 2004 from the internet: (http: www.sportsinjuryclinic.netlcybertherapis/frontlfootlplantarfasciitis/plantartaping.php).
Ace; Coach's Taping Kit (product image); 1 pg.; downloaded May 8, 2005 from the internet: (http://tsa.imageg.net/graphics/productimages/pGO 1-1 049858dt.jpg).
The Sports Authority; Ace Coach's Taping Kit (product info.); 2 pgs.; downloaded May 10, 2005 from the internet: (http://www.thesportsauthority.com/sm-ace-coach-taping-kit-pi-134240).
Dr. Scholl's; Moleskin Plus Padding (product page); 1 pg.; downloaded May 10, 2005 from the internet: (http://www.drscholls.com/product.aspx?prodid=5).
KBA Coach; Spenco Adhesive Knit (product info.); 1 pg.; downloaded May 10, 2005 from the internet: (http://www.kbacoach.com/spenadkit).
Kinesio Taping; taping instructions; 2 pgs.; downloaded May 10, 2005 from the internet: (http://kinesiotaping .com/content.asp?CustComKey=96149&CategoryKey=31687 &pn=Pag).
Jaybird & Mais; Adhesive Tape (product info.); 4 pgs.; downloaded May 10, 2005 from the internet: (hUp:llwww.jaybird.co/RigidTape.asp).
wisdomking.com; Leukotape P Sports Tape (product info.); 1 pg.; downloaded May 10, 2005 from the internet (http://www.wisdomking.com/product12127.html).
FIELDTEX; Ankle Taping (product info. & taping procedure); 2 pgs.; downloaded from the internet: www.fieldtex.com; (this web address was available to applicant(s) at least as of Jun. 23, 2005).
READYKOR; Basic Sports Taping Kit (product info.); 1 pg.; downloaded from the Internet May 8, 2005 from (hUpllwww.readykor.com/sport/BP-697.html).
Grisogono; Running Fitness and Injuries. A Self-Help Guide; New Zealand Ed.; Reed Publishing, Auckland, NZ; pp. 126-127; (year of pub. sufficiently earlier than effective US filing date and any foreign priority date) 1995.
Austin et al.; Illustrated Guide to Taping Techniques; A Moseby Ltd.; Oxford GB; pp. 58-71; (year of pub. sufficiently earlier than effective US filing date and any foreign priority date) 1994.
Applied Biokinetics LLC; FasciaDerm® Product Information; printed from website (http://www.fasciaderm.com); 4 pgs.; printed U.S. Appl. No. 11/712,013.
Larue; Adhesive Strapping in Sports for Foot (Videotape); Publisher: Roland E. LaRue, Lincoln, NE; 33 min.; (year of pub. sufficiently earlier than effective US filing date and any foreign priority date) 1998.
Vonhof; Fixing Your Feet: Prevention and Treatments for Athletes, 4th Edition; Wilderness Press; pp. 270-277; Jun. 19, 2012.
Case 6:21-cv-00557-ADA Document 13—p. 1, 25-32, and 44; Filed Aug. 9, 2021.
Case 6:21-cv-00556-ADA Document 13—p. 1, 32-39, and 56; Filed Aug. 9, 2021.
Case 6:21-cv-00555-ADA Document 13—p. 1, 26-34, and 47; Filed Aug. 9, 2021.
CVS Pharmacy, Inc.'S Final Invalidity Contentions, Apr. 11, 2022, pp. 1-251, *Applied BioKinetics, LLC* v. *CVS Pharmacy, Inc.*, No. 6:21-cv-00557-ADA (W.D. Tex.).
3M 361 Glass Cloth Tape, Product Data Sheet, Updated Mar. 1996.
3M 3998 Waterproof Cloth Tape, Product Data Sheet, Updated Mar. 1996.
3M Thermosetable Glass Cloth Tapes, 365 * 3650, Technical Data, May 2003.
Wilerson, Gary B.; Biomechanical and Neuromuscular Effects of Ankle Taping and Bracing, Journal of Athletic Training vol. 37—No. 4, Dec. 2002.
Simoneau, Guy G. et al.; Changes in Ankle Joint Proprioception Resulting From Strips of Athletic Tape Applied Over the Skin, Journal of Athletic Training, vol. 32—No. 2, Jun. 1997.
Lynch, Matt D., DPM et al.; Conservative Treatment of Plantar Fasciitis: A Prospective Study, vol. 88—No. 8, Aug. 1998.
Wolgin, Mark, MD et al.; Conservative Treatment of Plantar Heel Pain: Long-Term Follow-Up, American Orthopedic Foot and Ankle Society, Inc. Copyright 1994.
Bragg, Richard W.; Failure and fatigue characteristics of adhesive athletic tape, American College if Sports Medicine Copyright 2002.
Scherer, Paul R., DPM; Heel Spur Syndrome: Pathomechanics and Nonsurgical Treatment, Journal of the American Podiatric Medical Association, vol. 81—No. 2, Feb. 1991.
Roy, Steven, MD; How I Manage Plantar Fasciitis, The Physician and Sports Medicine, vol. 11—No. 10, Oct. 1983.
Schaeffer, Steven L., Dr.; Journal of Industrial Technology, vol. 16, No. 1, Nov. 1999-Jan. 2000.
Riddle, Dan L. et al.; Management of a Patient with a Diagnosis of Bilateral Plantar Fasciitis and Achilles Tendinitis, vol. 68—No. 12, Dec. 1988.
Hertling, Darlene et al.; Management of Common Musculoskeletal Disorders: Physical Therapy Principles and Methods, 2nd Edition, Copyright 1990.

(56) References Cited

OTHER PUBLICATIONS

Lohrer, Heinz et al.; Neuromuscular Properties and Functional Aspects of Taped Ankles, The American Journal of Sports Medicine, vol. 27—No. 1, Copyright 1999.
Davis, Pamela F., M.D. et al.; Painful Heel Syndrome: Results of Nonoperative Treatment, the American Orthopedic Foot and Ankle Society, Inc. Copyright 1994.
Kosmahl, Edmund M. et al.; Painful Plantar Heel, Plantar Fasciitis, and Calcaneal Spur: Etiology and Treatment, The Orthopedic and Sports Physical Therapy Sections of the American Physical Therapy Association, Copyright 1987.
Schepsis, Anthony A. et al.; Plantar Fasciitis, Etiology, Treatment, Surgical Results, and Review of the Literature, No. 266, May 1991.
Cornwall, Mark W., PT, PhD, CPed et al.; Plantar Fasciitis: Etiology and Treatment, Journal of Orthopedic & Sports Physical Therapy, Copyright 1999.
ASTM International; Standard Test Method for Tensile Strength and Elongation of Pressure-Sensitive Tapes, Published May 1996.
Georgia Institute of Tecnology ILL, Test methods for pressure sensitive adhesive tapes, pp. 9-20, 1994.
Ator, Rita, BS, PT, ATC et al.; The Effect of Adhesive Strapping on Medial Longitudinal Arch Support before and after Exercise, vol. 24—No. 1, Jul. 1991.
Manfroy, Pierre P. et al.; The Effects of Exercise, Prewrap, and Athletic Tape on the Maximal Active and Passive Ankle Resistance to Ankle Inversion, vol. 25—No. 2, 1997.
Sun, Tai-ping; The Effect of Two Taping Methods on Controlling Plantar Fasciitis, MGH Institute of Health Professions, Mar. 1999.
Sanzo, Paolo; The Effects of Low Dye Taping on Poot Pressure in Subjects with Plantar Fasciitis, Oct. 1995.
ASTM International, D 5330/D 5330M-01 Standard Specification for Pressure-Sensitive Tape for Packaging, Filament-Reinforced, Published Dec. 2001.
Kase et al., Clinical Therapeutic Applications of the Kinesio Taping Method 2nd Edition, Copyright 2003.
U.S. Appl. No. 16/387,250, Notice of Allowance dated Oct. 12, 2021.
Kenzo Kase, D.C., Illustrated Kinesio Taping—4th Edition, Copyright 2003 (Book).
Kinesio Taping Association, Kinesio Taping Perfect Manual—Amazing Taping Therapy to Eliminate Pain and Muscle Disorders, Copyright 2003 (Book).
Kenzo Kase, et al., Clinical Therapeutic Applications of the Kinesio Taping Method, Copyright 2003 (Book).
Kinesio Taping Association, Clinical Kinesio Taping, Copyright 1999 (Video).
CVS_InvalidityContentions-21-cv-555-556-557 dated Oct. 18, 2021.
Exhibit A-01—Invalidity Claim Chart—U.S. Pat. No. 8,414,511 dated Jun. 2, 2021.
Exhibit A-02—Invalidity Claim Chart—U.S. Pat. No. 8,216,162 dated Jun. 2, 2021.
Exhibit A-06—Invalidity Claim Chart—U.S. Pat. No. 10,212,987 dated Jun. 2, 2021.
U.S. Appl. No. 16/387,266, Notice of Allowance dated Nov. 2, 2021.
Jaybird & Mais, Inc., Sports Medicine Adhesive Tape Catalog, 2004, 8 pages.
Jaybird & Mais, Inc., Sports Medicine Adhesive Tape Catalog, 2005, 8 pages.
Jaybird & Mais, Inc., Sports Medicine Adhesive Tape Catalog, 2003, 8 pages.
3M, Technical Information Sheet Product No. 1530L, 3M Medical White Nonwoven Tape on Liner, Dec. 2003, 2 pages.
3M, Medical Nonwoven Tapes selection Guide—Rayon, undated, 1 page.
3M, Index,undated, 1 page.
3M, Technical Information Sheet Product No. 1776, 3M Medical Nonwoven Tape, Dec. 2003, 2 pages.
3M, 3M Medical Specialties Product Guide, undated, 78 pages.
3M, Medical Single Coated Film Tapes Selection Guide, undated, 1 page.
3M, Medical Nonwoven and Woven Tapes Selection Guide—Polyurethane and Rayon Acetate, undated, 1 page.
3M, Technical Information Sheet Product No. 1516 3M Single Coated Polyester Medical Tape, Dec. 2003, 2 pages.
English translation of EP1097975A2, Google Patents, 7 pages.
AMF Bowler's Tape, accessed from https://web.archive.org/web/20020809213542/http://www.amfproducts.com:80/prod/acc.asp, 1 page.
Listing of Tape Products, 1 page.
"KT Tape: Plantar Fasciitis" (Video) accessed Dec. 7, 2022 at https://www.youtube.com/watch?v=x272_NziK2g, Apr. 18, 2009, 1 page.
Halseth T, McChesney JW, Debeliso M, Vaughn R, Lien J. The effects of kinesio™ taping on proprioception at the ankle. J Sports Sd Med. Mar. 1, 2004;3(1):1-7. PMID: 24497814; PMCID: PMC3896108.
Giddings. V. L., Beaupre, G. S., Whalen, R. T., and Carter, D. R., Calcaneal loading during walking and running, Medicine & Science in Sports & Exercise, vol. 32, No. 3. 8 pages, 2000, Official Journal of the American College of Sports Medicine, Stanford, CA, US.
Boakye, Lorraine MD, Chambers, Monique C. MD, MSL, Carney, Dwayne MPH, Yan, Alan MD, Hogan, Macalus V. MD, and Ewalefo, Samuel O. BS, Management of Symptomatic Plantar Fasciitis, Operative Techniques in Orthopaedics, 2018, 7 pages, Elsevier Ltd, Amsterdam, NL.
Riddle, Daniel L. PT, PHD, Pulisic, Matthew PT, OCS, Pidcoe, Peter PT, PHD, & Johnson, Robert E. PHD, Risk Factors for Plantar Fasciitis: A Matched Case-Control Study, 2003, 7 pages, vol. 85-A, No. 5, The Journal of Bone and Joint Surgery, Inc., Needham, MA, USA.
Buchbinder, Rachelle MB, BS, FRACP, Clinical Practice: Plantar Fasciitis, The New England Journal of Medicine, May 20, 2004, 8 pages, vol. 350, No. 21, Massachusetts Medical Society, Waltham, MA, USA.
Selva, Francisco, Pardo, Alberto, Aguado, Xavier, Montava, Ignacio, Gil-Santos, Luis, and Barrios, Carlos, A study of reproducibility of kinesiology tape applications: review, reliability and validity, BMC Musculoskeletal Disorders, Apr. 9, 2019, 12 pages, vol. 20, BioMed Central, London, UK, GB.
Andreasson, Gunnar and Edberg, Bengt, Rheological Properties of Medical Tapes Used to Prevent Athletic Injuries, Textile Research Journal, Apr. 1983, 6 pages, Sages Publishing, Rosemont, IL, USA.
Aldape-Esquivel, Pedro DPM, and Shapiro, Jarrod DPM, FACPM, FACFAS, Plantar fasciitis: A New Approach to an Old Problem (https://lermagazine.com/article/plantar-fasciitis-a-new-approach-to-an-old-problem), Oct. 2019, 5 pages, Lower Extremity Review Magazine, Albany, NY, USA.
Ugbolue UC, Yates EL, Wearing SC, et al., Sex differences in heel pad stiffness during in vivo loading and unloading, Journal of Anatomy, 2020, 9 pages, Anatomical Society of Great Britain and Ireland, London, UK, GB.
Beeson, P. BSC, MSC, PHD, FFPM RCSP, Plantar fasciopathy: Revisiting the risk factors, Foot and Ankle Surgery, 2014, 6 pages, vol. 20, Elsevier Ltd, Amsterdam, NL.
Wearing, Scott C., Smeathers, James E., Urry, Stephen R., Hennig, Ewald M., and Hills, Andrew P., The Pathomechanics of Plantar Fasciitis, Sports Medicine, Feb. 2006, 29 pages, 36 (7), ADIS International Limited, BV.
Hicks, J. H., The Mechanics of the Foot. II. The Plantar Aponeurosis and the Arch, Journal of Anatomy, Jan. 1954, 7 pages, vol. 88, Part 1, Anatomical Society of Great Britain and Ireland, London, UK, GB.
Kalniev, M.A., Krastev, D., Krastev, N., Vidinov, K., Veltchev, L., and Mileva, M., Abnormal Attachments Between A Plantar Aponeurosis and Calcaneus, Clujul Medical, 2013, 3 pages, vol. 86 No. 3, Iuliu Hatieganu University of Medicine and Pharmacy, Cluj-Napoca, RO.
Matteoli, S., Madsen, M., Virga, A., Wilhjelm, J. E., Corvi, A., and Torp-Pedersen, S. T., In Vivo Heel Pad Elasticity Investigation: Comparing Males to Females. Abstract from International Tissue Elasticity Conference, Deauville, FR, 2012, 2 pages, Technical University of Denmark, DK.

(56) References Cited

OTHER PUBLICATIONS

Priesand, Sari J., Schmidt, Brian M., Ang, Lynn, Wrobel, James S., Munson, Michael, Ye, Wen, & Pop-Busui, Rodica, Plantar fasciitis in patients with type 1 and type 2 diabetes: A contemporary cohort study, Journal of Diabetes and Its Complications, Jun. 20, 2019, 5 pages, vol. 33, Elsevier Ltd, Amsterdam, NL.

Roxas, Mario ND, Plantar Fasciitis: Diagnosis and Therapeutic Considerations, 2005, 11 pages, vol. 10, No. 2, Alternative Medicine Review, Beaverton OR, USA.

Goff, James D. Do, and Crawford, Robert MD, Diagnosis and Treatment of Plantar Fasciitis, American Family Physician, Sep. 15, 2011, 7 pages, vol. 84 No. 6, American Academy of Family Physicians, Leawood, KS, USA.

Buchanan, Benjamin K., & Kushner, Donald, Plantar Fasciitis, Jul. 25, 2021, 11 pages, StatPearls Publishing LLC, Orlando, FL, USA.

Spears, I.R., Miller-Young, J. E., Waters, M., and Rome, K., The Effect of Loading Conditions on Stress in the Barefooted Heel Pad, Medicine & Science in Sports & Exercise, 2005, 8 pages, vol. 37 No. 6, Official Journal of the American College of Sports Medicine, Stanford, CA, US.

Sullivan, Justin, Pappasa, Evangelos, and Burns, Joshua, Role of mechanical factors in the clinical presentation of plantar heel pain: Implications for management, The Foot, 2020, 7 pages, vol. 42, Elsevier Ltd, Amsterdam, NL.

Trojian, Thomas MD, MMB, and Tucker, Alicia K. MD, Plantar Fasciitis, American Family Physician, 2019, 7 pages. vol. 99 No. 12, American Academy of Family Physicians, Leawood, KS, USA.

Barry, Melissa MD, Causation and risk factors of Plantar Fasciitis: Evidence-based review, Apr. 2016, 37 pages, ACC Research: Evidence Based Healthcare Review, NZ.

Vohra, Praveen K., DPM, Kincaid, Brian R., DC, Japour, Christopher J. DPM, MS, and Sobel, Ellen DPM, PHD, Ultrasonographic Evaluation of Plantar Fascia Bands: A Retrospective Study of 211 Symptomatic Feet, Journal of the American Podiatric Medical Association, Sep. 2002 • vol. 92 • No. 8, 6 pages, American Podiatric Medical Association, Bethesda, MD, USA.

Zhang, Hongmei, Xu, Lei, Liu, Zhihui, Lu, Shukuan, Yin, Jichao, Tian, Sibo, Yang, Xiaofeng, and Wan, Mingxi, Statistical and Texture Descriptors of Symptomatic Plantar Fasciitis Using Ultrasound Shear Wave Elastography, IEEE Access, Jul. 13, 2020, 14 pages, vol. 8, Institute of Electrical and Electronics Engineers, Manhattan, NY, USA.

Huerta, Javier Pascual, and Garcia, Juan Maria Alarcon, Effect of gender, age and anthropometric variables on plantar fascia thickness at different locations in asymptomatic subjects, European Journal of Radiology, 2007, 5 pages, vol. 62, Elsevier Ireland Ltd, IE.

Shiotani, Hiroto, Marnyama, Nana, Kurumisawa, Keisuke, Yamagishi, Takaki, and Kawakami, Yasuo, Human plantar fascial dimensions and shear wave velocity change in vivo as a function of ankle and metatarsophalangeal joint positions, No Date Provided, 33 pages, Waseda University, Tokyo, JP.

Todros, S., Biz, C., Ruggieri, P., and Pavan, P.G., Experimental Analysis of Plantar Fascia Mechanical Properties in Subjects with Foot Pathologies, Applied Sciences, 2021, 11 pages, MDPI, Basel, CH.

Hedrick, Mark R., The Plantar Aponeurosis, Foot & Ankle International, Oct. 1996, 4 pages, vol. 17, No. 10, American Orthopaedic Foot and Ankle Society, Inc., Rosemont, IL, USA.

Gariani, Karim, Waibel, Felix WA, Viehofer, Arnd F, & Uckay, Iiker, Plantar Fasciitis in Diabetic Foot Patients: Risk Factors, Pathophysiology, Diagnosis, and Management, Dove Press Journal: Diabetes, Metabolic Syndrome and Obesity: Targets and Therapy, 2020, 9 pages, vol. 13, Dove Medical Press Ltd, Macclesfield, Cheshire UK, GB.

Lemont, Harvey DPM, Ammirati, Krista M. BS, & Usen, Nsima MPH, Clinical Pathology: Plantar Fasciitis A Degenerative Process (Fasciosis) Without Inflammation, Journal of the American Pediatric Medical Association, May/Jun. 2003, 4 pages, vol. 93 No. 3, American Medical Association, IL, USA.

Guo, Junchao, Liu, Xiaoyu, Ding, Xili, Wang, Lizhen, & Fan, Yuba, Biomechanical and mechanical behavior of the plantar fascia in macro and micro structures, Journal of Biomechanics, 2018, 7 pages, vol. 76, Elsevier Ltd, Amsterdam, NL.

McDonald, KA, Stearne, SM, Alderson, JA, North, I, Pires, NJ, and Rubenson, J, The Role of Arch Compression and Metatarsophalangeal Joint Dynamics in Modulating Plantar Fascia Strain in Running, Apr. 7, 2016, 16 pages, PLoS ONE, San Francisco, CA, USA.

Belhan, Oktay, Kaya, Mehmet, and Gurger, Murat, The thickness of heel fat-pad in patients with plantar fasciitis, Turkish Association of Orthopaedics and Traumatology, Acta Orthopaedica et Traumatologica Turcica, 2019, 5 pages, vol. 53, Elsevier Ltd, Amsterdam, NL.

TAS, Serkan MSC, PT, BEK, Nilgun PT, Onur, Mehmet Ruhi MD, and Korkusuz, FEZA MD, Effects of Body Mass Index on Mechanical Properties of the Plantar Fascia and Heel Pad in Asymptomatic Participants, 2017, 6 pages, vol. 38 No. 7, American Orthopaedic Foot and Ankle Society, Inc., Rosemont, IL, USA.

Choudhary, Ranjeet, & Kunal, Kishor, Modifiable Risk Factors of Plantar Fasciitis in Non-Athletic Patients and Proposal of a New Objective Assessment System—RKISP, Revista Brasileira de Ortopedia, Sociedade Brasileira de Ortopedia e Traumatologia, 2021, 4 pages, vol. 56 No. 3, Elsevier Ltd, Amsterdam, NL.

Nahin, Richard L., Prevalence and Pharmaceutical Treatment of Plantar Fasciitis in United States Adults, The Journal of Pain, Aug. 2018, 12 pages, vol. 19, No. 8, Elsevier Ltd, Amsterdam, NL.

Gefen, Amit, The In Vivo Elastic Properties of the Plantar Fascia During the Contact Phase of Walking, Foot & Ankle International, Mar. 2003, 7 pages, vol. 24, No. 3, American Orthopaedic Foot and Ankle Society, Inc., Rosemont, IL, USA.

Cheng, Hsin-Yi Kathy PHD, Lin, Chun-Li PHD, Chou, Shih-Wei PHD, and Wang, Hsien-Wen MS, Nonlinear Finite Element Analysis of the Plantar Fascia due to the Windlass Mechanism, Foot & Ankle International, Aug. 2008, 8 pages, vol. 29, No. 8, American Orthopaedic Foot and Ankle Society, Inc., Rosemont, IL, USA.

McGonagle, Dennis, Marzo-Ortega, Helena, O'Connor, Philip, Gibbon, Wayne, Pease, Colin, Reece, Richard, and Emery, Paul, The Role of Biomechanical Factors and HLA-B27 in Magnetic Resonance Imaging-Determined Bone Changes in Plantar Fascia Enthesopathy, Arthritis & Rheumatism, American College of Rheumatology, Feb. 2002, 5 pages, vol. 46 No. 2, Wiley-Liss, Inc, Hoboken, NJ, USA.

Van Leeuwen, K D B, Rogers, J, Winzenberg, T, & Van Middelkoop, M, Higher body mass index is associated with plantar fasciopathy/'plantar fasciitis': systematic review and meta-analysis of various clinical and imaging risk factors, British Journal Sports Medicine, 2016, 54 pages, vol. 50, BMJ Journals, London, UK, GB.

Pekala, P.A., Kaythampillai, L., Skinningsrud, B., Loukas, M., Walocha, J.A., and Tomaszewski, K.A., Anatomical Variations of the Plantar Fascia's Origin with Respect to Age and Sex—An MRI Based Study, Clinical Anatomy, Apr. 1, 2019, 6 pages, vol. 32, Wiley Periodicals, Inc, Hoboken, NJ, USA.

Linwei, Chen, Biomechanics of The Plantar Fascia In Running and the Implication for Plantar Fasciitis, 2020, 221 pages. The Hong Kong Polytechnic University, HK.

Lee, Sae Yong, Hertel, Jay, and Lee, Sung Cheol, Rearfoot eversion has indirect effects on plantar fascia tension by changing the amount of arch collapse, The Foot, 2010, 7 pages, vol. 20, Elsevier Ltd, Amsterdam, NL.

Shiotani, Hirota, Yamashita, Ryo, Mizokuchi, Tomohiro, Sado, Natsuki, Naito, Munekazu, & Kawakami, Yasuo, Track distance runners exhibit bilateral differences in the plantar fascia stiffness, Scientific Reports, 2021, 8 pages, vol. 11, Nature Portfolio, London, UK, GB.

Orchard, John MD, Clinical Review: Plantar fasciitis, BMJ Journals, Oct. 10, 2012, 12 pages, BMJ Publishing Group Ltd, London, UK, GB.

Schwartz, Emily N MD, and Su, John MD, Plantar Fasciitis: A Concise Review, The Permanente Journal, Winter 2014, 3 pages, vol. 18 No. 1, The Permanente Federation LLC, Oakland, CA, USA.

TAS, Serkan, PhD, PT, Effect of Gender on Mechanical Properties of the Plantar—Fascia and Heel Fat Pad, Foot & Ankle Specialist, 2021, 7 pages, vol. 11, No. 5, Sages Publishing, Rosemont, IL, USA.

(56) References Cited

OTHER PUBLICATIONS

Ritter, Merrill A. & Albohm, Marjorie J., Your Injury: A Common Sense Guide to Sports Injuries, 1994, 6 pages, Masters Press, Indianapolis, IN, USA.
Zylks, Donald Ray ATC, MS, Alternative Taping for Plantar Fasciitis, Athletic Training, The Journal of The National Athletic Trainers Association, Inc., Winter 1987, 3 pages, vol. 22 No. 4, Allen Press, Lawrence, KS, USA.
Arnheim, Daniel D. DPE, ATC, Modern Principles of Athletic Training, 1989, 20 pages, Times Mirror / Mosby College Publishing, St. Louis MO, USA.
Walker, Archibald Brian MB, ChB., A Sports Injury Clinic: A Five Year Experience, Nov. 1989, 193 pages, No. 1417367, ProQuest Information and Learning Company, Ann Arbor, MI, USA.
FR2697156A1 (English translation) accessed from Google Patents on Mar. 17, 2023.
JP2000245771A (English translation) accessed from Google Patents on Mar. 17, 2023.
JP2001000463A (English translation) accessed from Google Patents on Mar. 17, 2023.
JP2001008961A (English translation) accessed from Google Patents on Mar. 17, 2023.
JP2001104366A (English translation) accessed from Google Patents on Mar. 17, 2023.
JP2002035196A (English translation) accessed from Google Patents on Mar. 17, 2023.
JP2002105703A (English translation) accessed from Google Patents on Mar. 17, 2023.
JP2002177319A (English translation) accessed from Google Patents on Mar. 17, 2023.
JP2002306529A (English translation) accessed from Google Patents on Mar. 17, 2023.
JP2003164484A (English translation) accessed from Google Patents on Mar. 17, 2023.
JP2004305533A (English translation) accessed from Google Patents on Mar. 17, 2023.
JP2004305540A (English translation) accessed from Google Patents on Mar. 17, 2023.
JP2005095203A (English translation) accessed from Google Patents on Mar. 17, 2023.
JP3100300B2 (English translation) accessed from Google Patents on Mar. 17, 2023.
JPH08131477A (English translation) accessed from Google Patents on Mar. 17, 2023.
JPH1033741A (English translation) accessed from Google Patents on Mar. 17, 2023.
JPH11199835A (English translation) accessed from Google Patents on Mar. 17, 2023.
KR20040048672 (English translation) accessed from Google Patents on Mar. 17, 2023.
TW459080B (English translation) accessed from Google Patents on Mar. 17, 2023.
3M Technical Information Sheet, Product No. 1785, 3M Medical Heatsealable Nonwoven Tape, Dec. 2003, 2 pages.
3M Technical Information Sheet, Product No. 1530, 3M Medical White Rayon Nonwoven Tape, Sep. 2003, 2 pages.
3M Technical Information Sheet, Product No. 1530L, 3M Medical White Rayon Nonwoven Tape on Liner, Dec. 2003, 2 pages.
3M Medical Nonwoven Tapes Selection Guide—Rayon, 1 page.
3M Technical Information Sheet, Product No. 1529, 3M Printable White Rayon Nonwoven Medical Tape, Dec. 2003, 2 pages.
3M Technical Information Sheet, Product No. 1515, 3M Medical White Film/ Nonwoven Composite Tape, Dec. 2003, 2 pages.
3M Technical Information Sheet, Product No. 9860, 3M Single Coated Medical Tape, Dec. 2003, 2 pages.
3M Technical Information Sheet, Product No. 9915, 3M Value Spunlace Medical Nonwoven Tape, Dec. 2003, 2 pages.
3M Listing of Tapes, 1 page.
3M Technical Information Sheet, Product No. 1538L, 3M Medical Rayon Woven Tape on Liner, Dec. 2003, 2 pages.
3M Technical Information Sheet, Product No. 1776, 3M Medical Nonwoven Tape on Liner, Dec. 2003, 2 pages.
3M Technical Information Sheet, Product No. 9916, 3M Medical Tan Nonwoven Tape, Jan. 2004, 2 pages.
3M Medical Specialities, Customer Focused Solutions for Medical Business to Business Markets, 78 pages.
3M Medical Single Coated Film Tapes Selection Guide, 1 page.
3M Technical Information Sheet, Product No. 1538, 3M Medical Rayon Woven Tape, Dec. 2003, 2 pages.
3M Technical Information Sheet, Product No. 9952 3M Single Coated Medical Plastic Tape, Dec. 2003, 2 pages.
3M Medical Nonwoven and Woven Tapes Selection Guide—Polyurethane and Rayon Acetate, 1 page.
3M Technical Information Sheet, Product No. 1533L, 3M Medical Tan Rayon Nonwoven Tape on Liner, Dec. 2003, 2 pages.
3M Technical Information Sheet, Product No. 1533, 3M Medical Tan Rayon Nonwoven Tape, Dec. 2003, 2 pages.
3M Technical Information Sheet, Product No. 1516, 3M Single Coated Polyester Medical Tape on Line, Dec. 2003, 2 pages.
Jaybird & Mais, Inc., Sports Medicine Adhesive Tape Catalog, 8 pages, 2003.
Jaybird & Mais, Inc., Sports Medicine Adhesive Tape Catalog, 8 pages, 2004.
Jaybird & Mais, Inc., Sports Medicine Adhesive Tape Catalog, 8 pages, 2005.
Jaybird & Mais, Inc., Athletic Trainers Products, 6 pages, 1997.
Hajaghazadeh, Mohammad & Minaei, Roya & Allahyari, Teimour & Khalkhali, Hamidreza, Anthropometric Dimensions of Foot in Northwestern Iran and Comparison with Other Populations, Health Scope, Aug. 2018, 9 pages, vol. 7 No. 3, Kowsar Medical Institute, Heerlen, NL.
Kennedy, Robert & Chen, Sanping & Pressman, Irwin & Yamashita, Akira & Pressman, Ari, A Large-Scale Statistical Analysis of Barefoot Impressions, Journal of Forensic Sciences, 2005, 11 pages, vol. 50, Wiley Periodicals, Inc, Hoboken, NJ, USA.
Kouchi, Makiko, Foot Dimensions and Foot Shape: Differences Due to Growth, Generation and Ethnic Origin, Anthropological Science, 1998, 28 pages, vol. 106 Supplement, Anthropological Science, The Anthropological Society of Nippon, Tokyo, JP.
Zhang, Xianyi & Pauel, Rinus & Deschamps, Kevin & Jonkers, Ilse & Vanwanseele, Benedicte, Differences in foot muscle morphology and foot kinematics between symptomatic and asymptomatic pronated feet, Scandinavian Journal of Medicine & Science in Sports, 2019, 25 pages, vol. 29 (Pre-Publication View), Wiley Periodicals, Inc, Hoboken, NJ, USA.
Qian Z, Jiang Z, Wu J, Chang F, Liu J, Ren L and Ren L, Morphology and Mechanical Properties of Plantar Fascia in Flexible Flatfoot: A Noninvasive In Vivo Study, Frontiers in Bioengineering and Biotechnology, Sep. 2021, 9 pages, vol. 9, Frontiers Media, Lausanne, CH.
Mukhra, Richa & Krishan, Kewal & Nirenberg, Michael & Ansert, Elizabeth & Kanchan, Tanuj, Comparative analysis of static and dynamic bare footprint dimensions in a north Indian population, Forensic Science International, 2020, 9 pages, vol. 308, Elsevier Science Ireland Ltd, IE.
Ansuategui Echeita, Jone & Humans, Juha & Smits, Sharon & Woude, Lucas & Postema, Klaas, Age-related differences in women's foot shape, Maturitas, 2016, 24 pages, vol. 94, Elsevier Ireland Ltd, IE.
Krauß, Inga & Grau, Stefan & Janssen, Pia & Maiwald, Christian & Mauch, Marlene & Horstmann, Thomas, Gender Differences In Foot Shape, 2023, 2 pages, Medical Clinic, Department of Sports Medicine, University Clinics Tubingen, DE.
Pawlaczyk, Mariola & Lelonkiewicz, Monika & Wieczorowski, Michal, Age-dependent biomechanical properties of the skin, 2013, 5 pages, Postepy dermatologii i alergologii, Poznan, PL.
Jammes Y, Viala M, Dutta W, Weber JP, Guieu R, Skin Hardness and Epidermal Thickness Affect the Vibration Sensitivity of the Foot Sole, Clinical Research on Foot & Ankle, 2017, 5 pages, vol. 5 No. 3, OMICS Publishing Group, Hyderabad, Telangana, IN.
Ariser, David & Ballard, Angela, Topical Therapies in Hyperhidrosis Care, Dermatologic Clinics, 2014, vol. 32, WB Saunders / Elsevier, Philadelphia, PA, USA.

(56) References Cited

OTHER PUBLICATIONS

Panagoulias GS, Eleftheriadou I, Papanas N, Manes C, Kamenovz, Tesic 0, Bousboulas S, Tentolouris A, Jude EB and Tentolouris N, Dryness of Foot Skin Assessed by the Visual Indicator Test and Risk of Diabetic Foot Ulceration: A Prospective Observational Study Frontiers in Endocrinology, 2020, 11 pages, vol. 11 Article 625 , Frontiers Media, Lausanne, CH.

Stolman, Lewis P. MD, FACP, FRCP, Hyperhidrosis Medical and Surgical Treatment, Eplasty, Open Science, Jan. 18, 2008, 11 pages, vol. 8, PLOS, San Francisco, CA, USA.

Menz, Hylton, Biomechanics of the Ageing Foot and Ankle: A Mini-Review. Journal of Foot and Ankle Research, 2014, 8 pages, vol. 5, BioMed Central, London, UK, GB. Note: Also published later in Gerontology 2015, vol. 61.

Derler, Siegfried & Gerhardt, Lutz-Christian, Tribology of Skin: Review and Analysis of Experimental Results for the Friction Coefficient of Human Skin, Tribology Letters, 2012, 27 pages, vol. 45, Springer Nature, London, UK, GB.

Schlereth, Tanja & Dieterich, Marianne & Birklein, Frank, Hyperhidrosis-Causes and Treatment of Enhanced Sweating, Deutsches Arzteblatt International, 2009, 8 pages, vol. 106, Deutscher Arzte-Verlag, Cologne, DE.

James, Kirstyn & Orkaby, Ariela & Schwartz, Andrea, Foot Examination for Older Adults, The American Journal of Medicine, 2020, 6 pages, vol. 134, Elsevier Ltd, Amsterdam, NL.

Haider, Aamir & Solish, Nowell, Focal hyperhidrosis: Diagnosis and management. CMAJ : Canadian Medical Association Journal, 2005, 7 pages, vol. 172, Canadian Medical Association, Ontario, CA.

Tasron, Diyana & Thurston, T.J. & Carre, Matt, Frictional Behaviour of Running Sock Textiles Against Plantar Skin, Procedia Engineering, 2015, 6 pages, vol. 112, Elsevier Ltd, Amsterdam, NL.

Kwan, Rachel & Zheng, Yong-Ping & Cheing, Gladys, The effect of aging on the biomechanical properties of plantar soft tissues. Clinical Biomechanics (Bristol, Avon), 2010, vol. 25, Elsevier Ltd, Amsterdam, NL.

Wright, D. G., and Rennels, D. C., A Study of the Elastic Properties of Plantar Fascia, The Journal of Bone and Joint Surgery, Apr. 1964, 11 pages, vol. 46-A, No. 3, The Journal of Bone and Joint Surgery, Inc., Needham, MA, USA.

Pavan, P. G., Stecco, C., Darwish, S., Natali, A. N., and De Caro, R., Investigation of the mechanical properties of the plantar aponeurosis, Surgical and Radiologic Anatomy, Sep. 2011, 8 pages, vol. 33, Springer Verlag, Berlin, DE.

Erdemir, Ahmet PHD, Hamel, Andrew J. PHD, Fauth, Andrew R. MSc, Piazza, Stephen J. PHD, and Sharkey, Neil A. PHD, Dynamic Loading of the Plantar Aponeurosis in Walking, The Journal of Bone and Joint Surgery, Mar. 2004, 8 pages, vol. 86-A, No. 3, The Journal of Bone and Joint Surgery, Inc., Needham, MA, USA.

Park, Se-Yeon, Bang, Hyun-Seok, and Park, Du-Jin, Potential for foot dysfunction and plantar fasciitis according to the shape of the foot arch in young adults, Journal of Exercise Rehabilitation, 2018, 6 pages, vol. 14 No. 3, Korean Society of Exercise Rehabilitation, KR.

Cua, A. B. Wilhelm K.-P., and Maibach H. I., Elastic Properties of Human Skin: Relation to Age, Sex, and Anatomical Region, 1990, 6 pages, Archives of Dermatological Research, Springer Verlag, Berlin, DE.

Perrin, David H., Athletic Taping and Bracing, 2012, 150 pages, 3rd Ed, Human Kinetics, Champaign, IL, USA.

Gross, Reuben H. M CP, Burnett, E.K., The Practice of Podiatry, 1933, 50 pages, Harriman Printing Company, Inc., New York, NY, USA.

Prentice, William E. Phd, AT, C, PT, Rehabilitation Techniques In Sports Medicine, 1990, 397 pages, CV Mosby Company, St. Louis, MS, USA.

Hauser, Emil D W, MS, MD, Diseases of the Foot, 1950, 78 pages, 2nd Ed, W. B. Saunders Company, London, UK, GB.

McMinn, Robert M H, Hutchings, Ralph T, and Logan, Bari M, Color Atlas of Foot and Ankle Anatomy, 1996, 123 pages, 2nd Ed, Mosby-Wolfe, London, England, GB.

Verbruggen, Laura A., Thompson, Melissa M., and Durall, Chris J., The Effectiveness of Low-Dye Taping in Reducing Pain Associated With Plantar Fasciitis, Journal of Sport Rehabilitation, 2018, 6 pages, vol. 27 No. 1, Human Kinetics, Inc., Champaign, IL, USA.

Viljakka, Timo, Mechanics of knee and ankle bandages, Acta Orthopaedica Scandinavica, 1986, 6 pages, vol. 57, Taylor & Francis Group, Oxfordshire, UK, GB.

Denyer, Joanna, The Effects of Foot Structure and Athletic Taping on Lower Limb Biomechanics, Oct. 2012, 285 pages. University of Hertfordshire, Hertfordshire, UK, GB.

Carter, Kate MSC, & Chockalingam, Nachiappan PHD, An Assessment of Strapping Techniques Commonly Used for Pronated Foot Deformities, Journal of the American Podiatric Medical Association, Sep./Oct. 2009, 9 pages, vol. 99 No. 5, American Podiatric Medical Association, Bethesda, MD, USA.

Franettovich, Melinda, Chapman, Andrew and Vicenzino, Bill, Tape That Increases Medial Longitudinal Arch Height Also Reduces Leg Muscle Activity: A Preliminary Study, Medicine & Science in Sports & Exercise, 8 pages, 2008, vol. 40, No. 4, Official Journal of the American College of Sports Medicine, Stanford, CA, US.

Park, Chan MS, PT, Lee, Sangyong PhD, PT, Lim, Dong-Young, Yi, Chae-Woo PT, Kim, Jang Hwan, Jeon, Chunbae PhD, PT, Effects of the application of Low-Dye taping on the pain and stability of patients with plantar fasciitis, Journal of Physical Therapy Science, 2015, 3 pages, vol. 27, No. 8, The Society of Physical Therapy Science, IPEC Inc., Fort Atkinson, WI, USA.

Hunt, Gary C., Brocato, Ronald S., & Cornwall, Mark W., Gait: Foot Mechanics and Neurobiomechanics, Physical Therapy of the Foot and Ankle, Jan. 1995, 35 pages, Chapter 3, Churchill Livingstone, Philadelphia, PA, USA.

Tarrant, Michelle M.Ed., ATC, LAT, Effects of Various Arch Support Techniques on the Human Running Gait, Dec. 2003, 20 pages, UMI No. 3114330, Texas Woman's University, Denton, TX, USA.

Petrofsky, Jerrold and Lee, Haneul, Greater Reduction of Balance as a Result of Increased Plantar Fascia Elasticity at Ovulation during the Menstrual Cycle, Tohoku J Exp. Med., 2015, 8 pages, vol. 237, Tohoku University Medical Press, Sendai, Miyagi, JP.

Zhang, Lei, Cheng, Han-Wen, Xiong, Lu-Jing, Xia, Zhang-Rong, Zhang, Meng-Yao, Fu, Shi-Jie, and Nang, Guo-You, The Relationship between Calcaneal Spur Type and Plantar Fasciitis in Chinese Population, BioMed Research International, 7 pages, Jun. 5, 2020, vol. 2020, Article ID 5679629, Hindawi, London, UK, GB.

D'Août, K., Pataky, T.C., De Clercq, D. & Aerts, P., The effects of habitual footwear use: foot shape and function in native barefoot walkers, Footwear Science, Jun. 2009, 15 pages, vol. 1, No. 2, Taylor & Francis Group, Oxfordshire, UK, GB.

Song, Jinsup BS, Hillstrom, Howard J. PhD, Secord, David DPM, & Levitt, James DPM, Foot Type Biomechanics: Comparison of Planus and Rectus Foot Types, Journal of the American Pediatric Medical Association, Jan. 1996, 8 pages, vol. 86 • No. 1, American Medical Association, IL, USA.

Nirenberg, Michael S., Krishan, Kewal, & Kanchan, Tanuj, A metric study of insole foot impressions in footwear of identical twins, Journal of Forensic and Legal Medicine, Sep. 11, 2017, 6 pages, vol. 52, Elsevier Ltd, Amsterdam, NL.

Jurca, Ales, Zabkar, Jure & Dzeroski, Saso, Analysis of 1.2 million foot scans from North America, Europe and Asia, Scientific Reports, 2019, 10 pages, vol. 9, Nature Portfolio, London, UK, GB.

Menz, HN, Roddy, E, Marshall, M, Thomas, MJ, Rathod, T, Peat, GM, & Croft, PR, Epidemiology of Shoe Wearing Patterns Over Time in Older Women: Associations With Foot Pain and Hallux Valgus, Journals of Gerontology: Medical Sciences 2016, 6 pages, vol. 71, No. 12, Oxford Press, Oxford, England, UK.

Kennedy, Robert B., Ongoing Research Into Barefoot Impression Evidence, Forensic Science and Medicine, Forensic Medicine of the Lower Extremity: Human Identification and Trauma Analysis of the Thigh, Leg, and Foot, 2005, 13 pages, Ch. 14, The Humana Press Inc., Totowa, NJ, USA.

Mootanah, R., Song, J., Lenhoff, M.W., Hafer, J.F., Backus, S.L, Gagnon, D., Deland III, J.T., and Hillstrom, H.J., Foot Type

(56) References Cited

OTHER PUBLICATIONS

Biomechanics Part 2: Are structure and anthropometries related to function? Gait Posture. Mar. 2013; 11 pages, vol. 37 No. 3, Elsevier B.V., Amsterdam, NL.

Hillstrom, H.J., Song, J., Kraszewski, A.P., Hafer, J.F., Mootanah, R., Dufour, A.B., Chow, B.S., and Deland III, J.T., Foot Type Biomechanics Part 1: Structure and Function of the Asymptomatic Foot, Gait Posture. Mar. 2013; 16 pages, vol. 37 No. 3, Elsevier B.V., Amsterdam, NL.

Tsung, Bonnie Yuk San Mphil, Zhang, Ming PHD, Fan, Yu Bo PHD, Boone, & David Alan CP, Mphil, Quantitative comparison of plantar foot shapes under different weight-bearing conditions, Journal of Rehabilitation Research and Development, Nov./Dec. 2003, 10 pages, vol. 40, No. 6, United States Department of Veterans Affairs, USA.

Fukano, Mako & Fukubayashi, Tom, Gender-based differences in the functional deformation of the foot longitudinal arch, The Foot, 2012, 4 pages, vol. 22, , Elsevier Ltd, Amsterdam, NL.

Domjanic, J, Fieder, M, Seidler, H, & Mitteroecker, P, Geometric morphometric footprint analysis of young women, Journal of Foot and Ankle Research, 2013, 8 pages, vol. 6 No. 27, BioMed Central, London, UK, GB.

Wunderlich, R, and Cavanagh, PR, Gender differences in adult foot shape: implications for shoe design, Medicine & Science in Sports & Exercise, 2001, 7 pages, vol. 33, No. 4, Official Journal of the American College of Sports Medicine, Stanford, CA, US.

Mei, Q., Gu, Y., Xiang, L et al., Foot shape and plantar pressure relationships in shod and barefoot populations, Biomechanics and Modeling in Mechanobiology, Sep. 30, 2019, 15 pages, vol. 19 No. 4, Springer-Verlag GmbH, DE.

Bhattacharjee, S, Ashrafuzzaman, MD, & Chakraborty, S, Assessment of Foot Shape in Adult Females of Bangalee and Chakma Ethnic Groups, Chattogram Maa-O-Shishu Hospital Medical College Journal, Jan. 2020, vol. 19, Iss. 1, Chattogram Maa-O-Shishu Hospital Medical College, Agrabad, Chattogram, BD.

Holowka, Nicholas B., Wallace, Ian J., & Lieberman, Daniel E., Foot strength and stiffness are related to footwear use in a comparison of minimally- vs. conventionally-shod populations, Scientific Reports, 2018, 12 pages, vol. 8, Nature Portfolio, London, UK, GB.

Martin-Casado, L; Barquin, C.; Aldana-Caballero, A.; Marcos-Tejedor, F.; Aguado, X., Environmental Factors as a Cause of Differences in the Feet of Ecuadorian Children and Its Relation to Their Footwear, Children, May 27, 2021, 8 pages, vol. 8, MDPI, Basel, CH.

Rossi, William A., The High Incidence of Mismated Feet in the Population, Foot & Ankle, 1983, 9 pages, vol. 4, No. 2, American Orthopaedic Foot and Ankle Society, Inc., Rosemont, IL, USA.

Ran, S., Liu, H., Yan, S., Li, R., Badurova, J. & Yang, L., Comparison of Foot Morphology Between Chinese and Mongolian Children, Leather and Footwear Journal, 2020, 12 pages, vol. 20 No. 2, CERTEX Publishing House, Bucharest, RO.

Lee, Yu-Chi, Kouchi, Makiko, Mochimaru, Masaaki, and Wang, Mao-Jiun, Comparing 3D Foot Shape Models Between Taiwanese and Japanese Females, Journal of Human Ergology, 2015, 10 pages, vol. 44, HumanErgology Society, Tokyo, JP.

Tomassoni, D., Traini, E., & Amenta, F., Gender and age related differences in foot morphology, Maturitas, Jul. 30, 2014, 8 pages, Elsevier Ireland Ltd, IE.

Mickle, KJ, Munro, BJ, Lord, SR, Menz, HB, and Steele, Jr, Foot shape of older people: implications for shoe design, Footwear Science, Sep. 2010, 10 pages, vol. 2, No. 3, Taylor & Francis Group, Oxfordshire, UK, GB.

Welte L, Kelly LA, Lichtwark GA, Rainbow MJ., Influence of the windlass mechanism on arch-spring mechanics during dynamic foot arch deformation, The Journal of the Royal Society Interface, 2018, 8 pages, vol. 15, The Royal Society Publishing, London, England, UK.

Tantisiriwat N, Janchai S., Mismated feet in diabetes, Chulalongkorn Medical Journal, Aug. 2006, 10 pages, vol. 50 No. 8, Chulalongkorn University, Bangkok, TH.

Saghazadeh, M. Kitano, N., Okura, T., Gender differences of foot characteristics in older Japanese adults using a 3D foot scanner, Journal of Foot and Ankle Research, 2015, 7 pages, vol. 8 No. 29, BioMed Central, London, UK, GB.

Xu, Miaomiao, Hong, Youlian, Li, Jing Xian, & Wang, Lin, Foot Morphology in Chinese School Children Varies by Sex and Age, Medical Science Monitor, Jul. 1, 2018, 11 pages, vol. 24 , International Scientific Information, Melville, New York, USA.

Shu Y, Mei Q, Fernandez J, Li Z, Feng N, Gu Y, Foot Morphological Difference between Habitually Shod and Unshod Runners, 2015, 13 pages, PLoS ONE, San Francisco, CA, USA.

McKay MJ, Baldwin JN, Ferreira P, Simic M, Vanicek N, Wojciechowski E, Mudge A, Burns J; 1000 Norms Project Consortium. Spatiotemporal and plantar pressure patterns of 1000 healthy individuals aged 3-101 years, Gait Posture. Oct. 2017; 33 pages, vol. 58, Elsevier B.V., Amsterdam, NL.

Al-Magsoosi, Suhad Kareem Rabi, Body Mass Index and Its Effect on Plantar Pressure in Overweight and Obese Adults, 2019, 203 pages, University of Southern Queensland, AU.

Kennedy, Robert B., Uniqueness of bare feet and its use as a possible means of identification, Forensic Science International, 1996, 7 pages, vol. 82, Elsevier Science Ireland Ltd, IE.

Xioing, Shuping & Goonetilleke, Ravindra & Zhao, Jianhui & Li, Wenyan & Witana, Channa, Foot deformations under different load-bearing conditions and their relationships to stature and body weight, 2009, 12 pages. vol. 117 No. 2, Anthropological Science, The Anthropological Society of Nippon, Tokyo, JP.

Sacco, Isabel & Onodera, Andrea & Bosch, Kerstin & Rosenbaum, Dieter, Comparisons of foot anthropometry and plantar arch indices between German and Brazilian children, BMC Pediatrics, 2015, 6 pages, vol. 15 No. 4, BioMed Central, London, UK, GB.

Kennedy, Robert & Pressman, Irwin & Chen, Sanping & Petersen, Peter & Pressman, Ari, Statistical Analysis of Barefoot Impressions. Journal of Forensic Sciences, 2003, 9 pages, vol. 48 No. 1, Wiley Periodicals, Inc, Hoboken, NJ, USA.

Krishan, Kewal, Individualizing characteristics of footprints in Gujjars of North India-Forensic aspects, Forensic Science International, 2007, 8 pages. vol. 169, Elsevier Science Ireland Ltd, IE.

Boppana, Abhishektha & Anderson, Allison, Dynamic foot morphology explained through 4D scanning and shape modeling, Journal of Biomechanics, Jul. 21, 2020, 29 pages, Preprint, Elsevier Ltd, Amsterdam, NL.

Kouchi, Makiko, Inter-Generation Differences in Foot Morphology: Aging or Secular Change?, Journal of Human Ergology, 2003, 26 pages, vol. 32, HumanErgology Society, Tokyo, JP.

Wong, Lilian & Hunt, Adrienne & Burns, Joshua & Crosbie, Jack, Effect of Foot Morphology on Center-of-Pressure Excursion During Barefoot Walking, Journal of the American Podiatric Medical Association, Mar. 2008, 7 Pages, vol. 98 • No. 2, American Podiatric Medical Association, Bethesda, MD, USA.

Hagedorn, Thomas & Dufour, Alyssa & Golightly, Yvonne & Riskowski, Jody & Hillstrom, Howard & Casey, Virginia & Hannan, Marian, Factors affecting center of pressure in older adults: The Framingham Foot Study, Journal of Foot and Ankle Research, 2013, 5 pages, vol. 6 No. 18, BioMed Central, London, UK, GB.

Shiotani, Hiroto & Yamashita, Ryo & Mizokuchi, Tomohiro & Naito, Munekazu & Kawakami, Yasuo, Site- and sex-differences in morphological and mechanical properties of the plantar fascia: A supersonic shear imaging study, Journal of Biomechanics, 2019, 6 pages, vol. 85, Elsevier Ltd, Amsterdam, NL.

Hollander, Karsten & De Villiers, Elbe & Sehner, Susanne & Wegscheider, Karl & Braumann, K-M & Venter, Ranel & Zech, Astrid, Growing-up (habitually) barefoot influences the development of foot and arch morphology in children and adolescents, Scientific Reports, Aug. 2017, 9 pages, vol. 7, Nature Portfolio, London, UK, GB.

WB, Vidona & Anibeze, Chike & EA, Esunwoke, Anthropometric Evaluation of Foot Shape Dimensions and Patterns for Ancestral Determination of South-East Nigerians, 2019, 8 pages, vol. 10 No. 1, Anatomical Society of Nigeria, NG.

(56) References Cited

OTHER PUBLICATIONS

DE10357231A1 (English translation) accessed from https://patents.google.com/patent/DE10357231A1/en?oq=DE10357231A1 on Mar. 17, 2023.

DE19950509C1 (English translation) accessed from https://patents.google.com/patent/DE19950509C1/en?oq=DE19950509 on Mar. 17, 2023.

DE20018575U1 (English translation) accessed from https://patents.google.com/patent/DE20018575U1/en?oq=DE20018575 on Mar. 17, 2023.

DE2356950A1 (English translation) accessed from https://patents.google.com/patent/DE2356950A1/en?oq=DE2356950 on Mar. 17, 2023.

EP1097975 (English translation) accessed from https://patents.google.com/patent/EP1097975A2/en?oq=EP1097975A2 on Mar. 17, 2023.

FR2697156A1 (English translation) accessed from https://patents.google.com/patent/FR2697156A1/en?oq=FR2697156 on Mar. 17, 2023.

FR791796A (English translation) generated by Google Translate on Mar. 17, 2023.

JP2000328025A (English translation) accessed from https://patents.google.com/patent/JP2000328025A/en?oq=JP2000328025 on Mar. 17, 2023.

JP2001115680A (English translation) accessed from https://patents.google.com/patent/JP2000328025A/en?og=JP2001115680 on Mar. 17, 2023.

JP2002209931A (English translation) accessed from https://patents.google.com/patent/JP2002209931A/en?oq=JP2002209931 on Mar. 17, 2023.

JP2003105158A5 (English translation) accessed from https://patents.google.com/patent/JP2002209931A/en?oq=JP2003105158 on Mar. 17, 2023.

JP2003329413A (English translation) accessed from https://patents.google.com/patent/JP2002209931A/en?oq=JP2003329413 on Mar. 17, 2023.

JP2005152402A (English translation) accessed from https://patents.google.com/patent/JP2002209931A/en?oq=JP2005152402 on Mar. 17, 2023.

Jaybird & Mais, Product Data Sheet (EX25 Pro-White—Rigid White Adhesive Tape), Mar. 5, 2015, 1 page, Jaybird & Mais, Inc., Lawrence, MA, USA.

Wallis, Jim MS, ATC, Kinesio Taping Method Video, No Date Provided, Bar Code: 693316-101-39 www.kinesiotaping.com, Kinesio Taping Association, Albuquerque NM, USA.

Kinesio Taping Association, Clinical Kinesio Taping Video, 1999, www.kinesiotaping.com, Kinesio Taping Association, Albuquerque NM, USA.

Wilkerson, Gary B., Biomechanical and Neuromuscular Effects of Ankle Taping and Bracing, Journal of Athletic Training, 2002, 10 pages, 37(4), National Athletic Trainers' Association, Inc, Chattanooga, TN, USA.

Halseth, Travis, McChesney, John W., Debeliso, Mark, Vaughn, Ross, and Lien, Jeff, The Effects Of Kinesio Taping on Proprioception at the Ankle, 2004, 7 pages, vol. 3, Journal of Sports Science and Medicine, Bursa TR.

Bragg, Richard W., Macmahon, John M., Overom, Erin K., Yerby, Scott A., Matheson, Gordon 0., Darter, Dennis R., and Thomas P. Andriachi, Failure and Fatigue Characteristics of Adhesive Athletic Tape, Medicine & Science In Sports & Exercise, 2002, 8 pages, 0195-9131 /02/3303-0403, American College of Sports Medicine, Indianapolis, IN USA.

Simoneau, Guy G. PHD, ATC, PT, Degner, Rebecca M. PT, Kramper, Cindi A. PT, Kittleson, Kent H. PT, Changes in Ankle Joint Proprioception Resulting From Strips of Athletic Tape Applied Over the Skin, Journal of athletic Training, Jun. 1997, 7 pages, vol. 32 • No. 2, Allen Press, Lawrence, KS, USA.

Cornwall, Mark W. PT, PHD, CPED, and McPoil, Thomas G., PT, PHD, ATC, Plantar Fasciitis: Etiology and Treatment, Journal of Orthopaedic & Sports Physical Therapy, 1999, 9 pages, vol. 29 No. 12, The Journal of Orthopaedic and Sports Physical Therapy, Alexandria, VA, USA.

Schepsis, Anthony A., MD, Leach, Robert E. MD, and Gorzyca, John MD, Plantar Fasciitis Etiology, Treatment, Surgical Results, and Review of the Literature, Clinical Orthopaedics and Related Research, May 1991, 12 pages. No. 266, Springer Science+Business Media, Berlin, DE.

Manfroy, Pierre P., Ashton-Miller, James A. PHD, and Wojtys, Edward M., The Effect of Exercise, Prewrap, and Athletic Tape on the Maximal Active and Passive Ankle Resistance to Ankle Inversion, American Journal of Sports Medicine, 1997, 8 pages, vol. 25, No. 2, American Orthopaedic Society for Sports Medicine, Sages Publishing, Rosemont, IL, USA.

Roy, Steven MD, How I Manage Plantar Fasciitis, The Physician and Sportsmedicine, Oct. 1983, 4 pages, vol. 11 • No. 10, Informa, PLC, London, England, UK.

Wolgin, Mark MD, Cook, Charles MD, Graham, Charles MD, and Mauldin, Don MD, Conservative Treatment of Plantar Heel Pain: Long-Term Follow-Up, Mar. 1994, 6 pages, vol. 15 No. 3, American Orthopaedic Foot and Ankle Society, Inc., Rosemont, IL, USA.

Riddle, Dan L., and Freeman, Denise B., Management of a Patient with a Diagnosis of Bilateral Plantar Fasciitis and Achilles Tendinitis, Physical Therapy, Dec. 1988, 4 pages, vol. 68 No. 12, American Physical Therapy Association, Oxford University Press, USA.

Lynch, D.Matt DPM, Goforth, W. Preston DPM, Martin, Joe E. DPM, Odom, Richard D. DPM, Preece, Cheryl Kasberg MS, Kotter, Michael W. DPM, Conservative Treatment of Plantar Fasciitis A Prospective Study, Journal of the American Pediatric Medical Association, Aug. 1998, 6 pages, vol. 88 • No. 8, American Medical Association, IL, USA.

Lohrer, Heinz MD, Alt, Wilfried PHD, and Gollhofer, Albert PHD, Neuromuscular Properties and Functional Aspects of Taped Ankles, The American Journal of Sports Medicine, 1999, 7 pages, vol. 27, No. 1, American Orthopaedic Society for Sports Medicine , Sages Publishing, Rosemont, IL, USA.

Davis, Pamela F. MD, Severud, Erik MD, and Baxter, Donald E. MD, Painful Heel Syndrome: Results of Nonoperative Treatment, Foot & Ankle International, Oct. 1994, 5 pages, vol. 15, No. 10, American Orthopaedic Foot and Ankle Society, Inc., Rosemont, IL, USA.

Scherer, Paul R. DPM, Heel Spur Syndrome Pathomechanics and Nonsurgical Treatment, Journal of the American Podiatric Medical Association, Feb. 1991, 5 Pages, vol. 81 • No. 2, American Podiatric Medical Association, Bethesda, MD, USA.

Kase, Kenzo, Wallis, Jim, and Kase Tsuyoshi, Clinical Therapeutic Applications of the Kinesio Taping Method Video, 2003, 249 pages, 2nd Edition, Kinesio Taping Association, Albuquerque NM, USA.

Kase, Kenzo, Wallis, Jim, and Kase Tsuyoshi, Clinical Therapeutic Applications of the Kinesio Taping Method Video, 2003, 239 pages, Kinesio Taping Association, Albuquerque NM, USA.

No Author Listed, Appendages A, B, C, D, Test Methods for Pressure Sensitive Adhesive Tapes, 1994, 13 pages, ILLiad TN: 467853, Georgia Institute of Technology ILL, Atlanta, GA, USA.

ASTM International, Standard Test Method for Tensile Strength and Elongation of Pressure-Sensitive Tapes, Annual Book of ASTM Standards, Dec. 1997, 7 pages, D 3759/D 3759M, ASTM International, West Conshohocken, PA, USA.

No Author Listed, PSTC-3 Standard Adhesion to Steel, Test Methods For Pressure Sensitive Adhesive Tapes, 1994, 5 pages, ILLiad TN: 467853, Georgia Institute of Technology ILL, Atlanta, GA, USA.

ASTM International, Standard Specification for Pressure-Sensitive Tape for Packaging, Filament-Reinforced, Annual Book of ASTM Standards, Dec. 2001, 4 pages, D 5330/D 5330M, ASTM International, West Conshohocken, PA, USA.

Schaeffer, Dr. Steven L., Slusarski, MS. Jill, Vantiem, MS. Valeria and Johnson, Dr. M.L., Tensile Strength Comparison of Athletic Tapes: Assessed Using ASTM D3759M-96, Standard Test Method for Tensile Strength and Elongation of Pressure-Sensitive Tapes,

(56) References Cited

OTHER PUBLICATIONS

Journal of Industrial Technology, Nov. 1999, 6 pages, vol. 16, No. 1, National Association of Industrial Technology, North Huntingdon, PA USA.
3M, Thermosetable Glass Cloth Tapes 365 / 360, Technical Data, May 2003, 2 pages, 3M Industrial Business, St. Paul, MN, USA.
3M, 3998 Waterproof Cloth Tape, Product Data Sheet, Mar. 1996, 2 pages, 3M Industrial Business, St. Paul, MN, USA.
3M, 361 Glass Cloth Tape, Product Data Sheet, Mar. 1996, 2 pages, 3M Industrial Business, St. Paul, MN, USA.
Kaplan, Charles DPM, Natale, Peter D. DPM, and Spilken, Terry L. DPM, Paddings and Strappings of the Foot, 1982, 3 pages, Futura Publishing Company, Inc., Mount Kisco, NY, USA.
Weisenfeld, Murray F. and Burr, Barbara, The Runners' Repair Manual, 1980, 5 pages, St. Martin's Press, Inc., New York, NY, USA.
Callaghan, Michael J., Role of ankle taping and bracing in the athlete, British Journal Sports Medicine, 1997, 7 pages. vol. 31, British Journal Sports Medicine, BMJ Journals, London, UK, GB.
Austin, Karin, Gwynn-Brett, Kathryn, and Marshall, Sarah, Illustrated Guide to Taping Techniques, 1994, 10 pages, Mosby-Wolfe, London, England, GB.
Kane, Peggy, Schlefman, Barbara S., Vickers, and Nancy Sinnott, Podiatric Office Management and Procedure, 1992, 3 pages, Mosby-Year Book, Inc., St. Louis, MO, USA.
Cozen, Lewis MD, FACS, Brockway, Alma MD, and McMaster, Paul E. MD, FACS, Operative Orthopedic Clinics, 1955, 56 Pages, J. B. Lippincott Company, Philadelphia, PA, USA.
Subotnick, Steven I., Sports Medicine of the Lower Extremity, 1999, 806 pages, 2nd Ed, Churchill Livingstone, Philadelphia, PA, USA.
Dorman, Thomas A., and Ravin, Thomas H., Diagnosis And Injection Techniques in Orthopedic Medicine, 1991, 322 pages, Williams & Wilkins, Baltimore, MA, USA.
Varzos, Peter N. DPM, Podiatric Emergencies: Their Prevention and Initial Care by the Industrial Nurse, Presented at the AAIN Conference, Chicago, IL, Apr. 14, 1970, Sep. 1970, 6 pages, Occupational Health Nursing, Chicago, IL, USA.
Wise, David D. B SC, PT, MD, Physiotherapeutic treatment of athletic injuries to the muscle-tendon complex of the leg, Canadian Medical Association Journal, Sep. 17, 1977, 3 pages, vol. 117, Canadian Medical Association, Ontario, CA.
Garfinkel, Daniel MD, and Rothenberger, Lee A. MA, Foot Problems in Athletes, Problems in Family Practice, The Journal of Family Practice, 1984, 12 pages, vol. 19, No. 2, Appleton-Century Crofts, USA.
Retzky, Sandra S. Do, MBA, and Baker, Timothy MD, MPH, Electronic Health Records and Marketplace Influences, Maryland Medicine, Summer 2010, 3 pages, MEDCHI, Baltimore, MD, USA.
Sanzo, P. and Bauer, T., The Effects of Low Dye Taping on Foot Pressure In Subjects With Plantar Fasciitis, No Date, 3 pages, Lakehead University, Ontario, CA.
Landorf, Karl B., Radford, Joel A., Keenan, Anne-Maree, and Redmond, Anthony C., Effectiveness of Low-Dye Taping for the Short-term Management of Plantar Fasciitis, Journal of the American Podiatric Medical Association, Nov./Dec. 2005, 6 pages, vol. 95 No. 6, American Podiatric Medical Association, Bethesda, MD, USA.
Atkins, D., Crawford, F., Edwards, J., and Lambert, M., A Systematic Review of Treatments for the Painful Heel, Rheumatology, 1999; 6 pages, vol. 38, British Society for Rheumatology, London, UK, GB.
Taunton, Jack E., Ryan, Michael B., Clement, Douglas B., McKenzie, Donald C., and Lloyd-Smith, D. Robert, Plantar fasciitis: a retrospective analysis of 267 cases, Physical Therapy In Sport, 2002, 9 pages, vol. 3, Elsevier Science Ltd., New York, NY, USA.
Radford, Joel A., Landorf, Karl B., Buchbinder, Rachelle and Cook, Catherine, Effectiveness of low-Dye taping for the short-term treatment of plantar heel pain: a randomised trial, BMC Musculoskeletal Disorders, Aug. 9, 2006, 7 pages, vol. 7, BioMed Central, London, UK, GB.
Arya, Aishwarya, & Nijhawan, Megha Arora, Comparative Effectiveness of Kinesiotaping and Low Dye Taping in Improving Pain and Disability in Subjects with Plantar Fasciitis, International Journal of Health Sciences & Research, Sep. 2019, 7 pages, vol. 9 Iss. 9; www.ijhsr.org.
Sanzo, Paolo, & Bauer, Tony, The Effects of Low Dye Taping on Vertical Foot Pressure in Subjects with Plantar Fasciitis, International Journal of Prevention and Treatment, 2015, 7 pages, vol. 4, Scientific & Academic Publishing (online), USA.
Chen, Tony Lin-Wei, Wong, Duo Wai-Chi, Peng, Yinghu, & Zhang, Ming, Prediction on the plantar fascia strain offload upon Fascia taping and Low-Dye taping during running, Journal of Orthopaedic Translation, 2020, 9 pages, vol. 20, Elsevier (Singapore) Pte Ltd on behalf of Chinese Speaking Orthopaedic Society, SG.
Podolsky, Roman & Kalichman, Leonid, Taping for plantar fasciitis, Journal of Back and Musculoskeletal Rehabilitation, 2015, 6 pages, vol. 28, IOS Press, Amsterdam, NL.
Aishwarya, N.C., & Sai, K. Venkata, Immediate Effect of Calcaneal Taping Versus Windlass Taping on Calcaneal Angle in Subjects With Plantar Fasciitis, 2016, 5 pages, vol. 33, International Journal of Therapeutic Applications, Bangalore, IN.
Erdemir, Ahmet PHD, Hamel, Andrew J. PHD, Fauth, Andrew R. MSc, Piazza, Stephen J. PHD, & Sharkey, Neil A. PHD, Dynamic Loading of the Plantar Aponeurosis in Walking, Mar. 2004, 7 pages, vol. 86-A No. 3, The Journal of Bone and Joint Surgery, Inc., Needham, MA, USA.
AMF, Bowler's Tape, 2002, 1 page, AMF Bowling Worldwide, Inc., https://web.archive.org/web/20020809213542/http://www.amfproducts.com:80/prod/acc.asp.
Jam, Bahram and Varamini, Abbas, A Clinical Manual On Therapeutic Taping For Peripheral and Spinal Syndromes, 2004, 104 pages, Part 1, Advanced Physical Therapy Education Institute (APTEI), Ontario, CA.
Mueller Sports Medicine, Tape, 2003, 2 pages, Mueller Sports Medicine, Inc., https://web.archive.org/web/20030204231315/http://www.muellersportsmed.com/tape.htm.
Hertling, Darlene and Kessler, Randolph M., Management of Common Musculoskeletal Disorders Physical Therapy Principles and Methods, 1990, 8 pages, Second Edition, J. B. Lippincott Company, Philadelphia, PA, USA.
Kosmahl, Edmund M. and Kosmahl, Herbert Kosmahl, Painful Plantar Heel, Plantar Fasciitis, and Calcaneal Spur: Etiology and Treatment, The Journal of Orthopaedic and Sports Physical Therapy, 1987, 8 pages, The Orthopaedic and Sports Physical Therapy Section in The American Physical Therapy Association, USA.
Sanzo, Paolo, The Effects of Low Dye Taping on Foot Pressure in Subjects With Plantar Fasciitis, Oct. 1995, 116 pages, ProQuest LLC, Ann Arbor, MI, USA.
BSN Medical, Leukotape® P Rigid Strapping Tape, Jun. 2003, 2 pages, BCN Medical Limited, Hull, UK.
Sun, Tai-Ping, The Effect of Two Taping Methods on Controlling Plantar Fasciitis, 1994, 77 pages, UMI #: 1393354; UMI Company, Ann Arbor, MI, USA.
Foy, Chris, Application: Basic Achilles Taping Procedure, 2003, 6 pages, Jaybird & Mais, Inc., Lawrence, MA, USA.
Poitras, Artie, Application: Basic Ankle Taping Procedure, 2003, 6 pages, Jaybird & Mais, Inc., Lawrence, MA, USA.
Perkins, ED, Application: Elbow Taping Procedure, 2003, 5 pages, Jaybird & Mais, Inc., Lawrence, MA, USA.
Bragg, R.W., Mcmahon, J. M., Overdom, E. K., Yerby, S. A., Matheson, G. O., Carter, D. R. and T. P. Andriacchi, Failure and Fatigue Characteristics of Adhesive Athletic Tape, Medicine & Science in Sports & Exercise, vol. 33, No. 3. 8 pages, 2002, Official Journal of the American College of Sports Medicine, Stanford, CA, US.
Shelton, Bridgette L., Implications of Achilles Tendon Taping on Muscle Activity of the Lower Leg, Aug. 2003, 89 pages, UMI No. 1417367, ProQuest Information and Learning Company, Ann Arbor, MI, USA.

(56) References Cited

OTHER PUBLICATIONS

Ator, Rita, BS, PT, ATC, Gunn, Kay, BS, PT, ATC, McPoil, Thomas G., PHD, PT, ATC, and Knecht, Harry G. Edd, PT, The Effect of Adhesive Strapping on Medial Longitudinal Arch Support before and after Exercise, Journal of Orthopaedics Sports Physical Therapy, Jul. 1991, 7 pages, vol. 14 No. 1, The Journal of Orthopaedic and Sports Physical Therapy, Alexandria, VA, USA.
Jaybird & Mais, Product Data Sheet (#5000 Jaylastic Plus II Tan & #5500 Jaylastic Plus II White), Mar. 5, 2015, 1 page, Jaybird & Mais, Inc., Lawrence, MA, USA.
Jaybird & Mais, Product Data Sheet (EX1 Jaybird One—Rigid White Adhesive Tape), Mar. 5, 2015, 1 page, Jaybird & Mais, Inc., Lawrence, MA, USA.
Jaybird & Mais, Product Data Sheet (#90 Tan/#95 White Jaystrap), 2001,2 pages, Jaybird & Mais, Inc., Lawrence, MA, USA. https://web.archive.org/web/20010303130455/http://www.jaybird.com.
Jaybird & Mais, Product Data Sheet (EX1 Jaybird One), 2001, 2 pages, Jaybird & Mais, Inc., Lawrence, MA, USA. https://web.archive.org/web/20010415015109/http://www.jaybird.com.
Jaybird & Mais, Product Data Sheet (#7700 Jaylastic Hybrid), Mar. 6, 2015, 1 page, Jaybird & Mais, Inc., Lawrence, MA, USA.
Jaybird & Mais, Product Data Sheet (#4500 Jaylastic), 2002, 2 pages, Jaybird & Mais, Inc., Lawrence, MA, USA. https://web.archive.org/web/20020115042759/http://www.jaybird.com.
Jaybird & Mais, Product Data Sheet (#4600 Jaylastic Select), Mar. 5, 2015, 1 page, Jaybird & Mais, Inc., Lawrence, MA, USA.
Jaybird & Mais, Sports Medicine Tape Products, 2001, 2 pages, Jaybird & Mais, Inc., Lawrence, MA, USA. https://web.archive.org/web/20001028155904/http://www.jaybird.com/SportsMed.htm.
Jaybird & Mais, Product Data Sheet (#40 Polyester Cotton Blend—Rigid White Adhesive Tape), Mar. 5, 2015, 1 page, Jaybird & Mais, Inc., Lawrence, MA, USA.
Jaybird & Mais, Product Data Sheet (95 White Jaystrap), Jan. 2019, 1 page, Jaybird & Mais, Inc., Lawrence, MA, USA.
Jaybird & Mais, Product Data Sheet (#EX25 Pro-White non-elastic sports medicine adhesive tape), 2001, 2 pages, Jaybirds Mais, Inc., Lawrence, MA, USA. https://web.archive.org/web/20010303173551/http://www.jaybird.com.
Jaybird & Mais, Product Data Sheet (#7000 Jaybird MST), 2001, 2 pages, Jaybird & Mais, Inc., Lawrence, MA, USA. https://web.archive.org/web/20010303131116/http://www.jaybird.com.
Jaybird & Mais, Product Data Sheet (#90 Jaystrap Tan), Jan. 2019, 1 page, Jaybird & Mais, Inc., Lawrence, MA, USA.
Jaybird & Mais, Product Data Sheet (#4500B Jaylastic Black Lightweight Adhesive Stretch Tape), Mar. 5, 2015, 1 page, Jaybird & Mais, Inc., Lawrence, MA, USA.
Jaybird & Mais, Product Data Sheet (#5000/#5500 Jaylastic Plus II), 2001, 2 pages, Jaybird & Mais, Inc., Lawrence, MA, USA. https://web.archive.org/web/20010303071633/http://www.jaybird.com.
Jaybird & Mais, Product Data Sheet (#EX25F Pro-Flesh), 2002, 2 pages, Jaybird & Mais, Inc., Lawrence, MA, USA. https://web.archive.org/web/20020712064104/http://www.jaybird.com/EX25F.htm.
Hart, Joseph M. PHD, ATC, Grindstaff, Terry L. PT, DPT, ATC, SCS, CSCS, Beazell, James R. PT, DPT, OCS, FAAOMPT, ATC; Magrum, Eric M. PT, OCS, FAAOMPT; and Hertel, Jay PHD, ATC, FACSM, FNATA, Taping Technique for Restricted Ankle Dorsiflexion, Athletic Training & Sports Health Care, 2009, 1 page, vol. 1, No. 4, Charlottesville, VA, USA.
Schulthies, Shane S. PHD, PT, ATC, and Draper, David 0. Edd, ATC, A Modified Low-Dye Taping Technique to Support the Medial Longitudinal Arch and Reduce Excessive Pronation, Journal of Athletic Training, Sep. 1995, 3 pages, vol. 30 No. 3, Allen Press, Lawrence, KS, USA.
MACTAC, Product Announcement: Three Levels of Strength, Jan. 2009, 2 pages, MACtac, Stow, OH, USA.
Knight, Brett MS, LAT, ATC, Oney, Jeff MS, AT, L/AT, CSCS, Miller, Michael G. Edd, AT, ATC, CSCS, and Gymkos, Amy MA, HFI, Comparison of Self-Adherent and Cloth Tape on Dynamic Ankle Inversion Before and After Exercise, Athletic Training & Sports Health Care, 2012, 7 pages, vol. 4 No. 2, SLACK Incorporated, Thorofare, NJ, USA.
Mausar, Joe, Passing the Torch, www.adhesivesmag.com eMagazine, Oct. 2011, 5 pages, BNP Media, Troy, MI, USA.
Lange, Belinda BSC, B Physiotherapy, Chipchase, Lucy Mapa, M APP SC, and Evans, Angela DIP APP SC, GRAD DIP SOC SC, FAAPSM, The Effect of Low-Dye Taping on Plantar Pressures, During Gait, in Subjects with Navicular Drop Exceeding 10 mm, Orthop Sports Phys Ther, Apr. 2004, vol. 34 • No. 4, The Journal of Orthopaedic and Sports Physical Therapy, Alexandria, VA, USA.
Kam Lun, Leung, Systematic Objective Evaluation of Flexible Flat Foot and a Rationale of Orthotic Treatment, Jul. 2003, 265 pages, The Chinese University of Hong Kong, Hong Kong, CN.
Anonymous, What's New, www.adhesivesmag.com eMagazine, Jul. 2008, 6 pages, BNP Media, Troy, MI, USA.
MACTAC, Product Offering: Medical Adhesive Systems, 2010, 56 pages, MACtac, Stow, OH, USA.
Hurst, Nicole Anna, Controlling Navicular Height Before and After Exercise: Comparing a Modified Low-Dye Taping Technique and a Navicular Strap Taping Technique, Jul. 3, 2008, 78 pages, UMI No. 1457866, ProQuest LLC, Ann Arbor, MI, USA.
Burkitt, Brian, Reilly, Brian, and Peak, Danielle, New Technologies in Silicone Adhesives, www. adhesivesmag.com eMagazine, Aug. 2012, 3 pages, BNP Media, Troy, MI, USA.
McGuiggan, PM, Chiche, A, Filliben, JJ, Phelan, FR, JR, and Fasolka, M, High-Throughput Peel Measurement of a Pressure-Sensitive Adhesive, www.adhesivesmag.com eMagazine, Apr. 2006, 6 pages, BNP Media, Troy, MI, USA.
Wittich, FW, AM, MD + Multiple Add'l Contributors, The Journal of the National Association of Chiropodists, Nov. 1, 1932, 41 pages, vol. 22 No. 11, The National Association of Chiropodists, Rockland, MA, USA.
Austin, Karin, Gwynn-Brett, Kathryn, and Marshall, Sarah, Illustrated Guide to Taping Techniques, 1994, 234 pages, Mosby-Wolfe, London, England, GB.
Findtape.com, Product Description (Jaybird & Mais EX25 Non-Elastic Athletic Tape), Jan. 8, 2022, 7 pages, FindTape.com, NJ, USA.
Findtape.com, Product Description (Jaybird & Mais EX1 Jaybird One Premium Non-Elastic Athletic Tape), 2022, 7 pages, FindTape.com, NJ, USA.
Findtape.com, Product Description (Jaybird & Mais 90/95 Jaystrap Heavy-Duty Taping Sports Medicine Tape), 2022, 5 pages, FindTape.com, NJ, USA.
Jaybird & Mais, Product Data Sheet (95 Jaystrap White—Rigid White Heavy-Duty Adhesive Tape), Jan. 2019, 1 page, Jaybird & Mais, Inc., Lawrence, MA, USA.
*Applied BioKinetics LLC* v. *KT Health, LLC*, 22-638-RGA-JLH Invalidity Claim Charts—U.S. Pat. No. 8,968,229.
*Applied BioKinetics LLC* v. *KT Health, LLC*, 22-638-RGA-JLH Invalidity Claim Charts—U.S. Pat. No. 8,834,398.
*Applied BioKinetics LLC* v. *KT Health, LLC*, 22-638-RGA-JLH Invalidity Claim Charts—U S. Pat. No. 8,414,511.
*Applied BioKinetics LLC* v. *KT Health, LLC*, 22-638-RGA-JLH Invalidity Claim Charts—U S. Pat. No. 11,096,815.
*Applied BioKinetics LLC* v. *KT Health, LLC*, 22-638-RGA-JLH Invalidity Claim Charts—U S. Pat. No. 8,814,818.
*Applied BioKinetics LLC* v. *KT Health, LLC*, 22-638-RGA-JLH Invalidity Claim Charts—U.S. Pat. No. 11,206,894.
*Applied BioKinetics LLC* v. *KT Health, LLC*, 22-638-RGA-JLH Invalidity Claim Charts—U S. Pat. No. 10,299,953.
*Applied BioKinetics LLC* v. *KT Health, LLC*, 22-638-RGA-JLH Invalidity Claim Charts—U S. Pat. No. 10,212,987.

\* cited by examiner

PRE-CUT ADHESIVE SUPPORTS FOR ANATOMICAL SUPPORT, PAIN REDUCTION, OR THERAPEUTIC TREATMENT

BACKGROUND OF THE INVENTION

The present invention generally relates to a stretch resistant plantar fascia support system. More particularly, the present invention relates to a stretch resistant plantar fascia support system that may be adhesively applied to a foot to provide relief from plantar fasciitis.

FIG. 1 is a dissected bottom view of a human foot 100 provided to illustrate some of the parts of a plantar fascia 110 located in the bottom of the human foot 100. As shown in FIG. 1, the plantar fascia 110 extends from about the location of the heel 101 to about the location of the ball 102 of the foot. The plantar fascia 110 includes medial plantar fascia 120, superficial tracts 130, a central component of the plantar fascia 140, and a lateral component of the plantar fascia 150. The separate portions of the plantar fascia 110 act as a shock absorber while walking and transfer tensile forces along the bottom of the foot 100.

FIG. 2 illustrates a simplified side view of tissue and bone structure in the human foot 100. As shown in FIG. 2, the human foot 100 includes the plantar fascia 110, a plantar calcaneus 160, a talus 162, a navicular 164, a cuneiform 166, a cuboid 168, metatarsals 170, phalanges 172, a sesamoid 174, a fat pad area 176, and an outer skin surface 178. From the side view in FIG. 2, the plantar calcaneus 160, the talus 162, the navicular 164, the cuneiform 166, the cuboid 168, the metatarsals 170, and the sesamoid 174 form what resembles the shape of an arch. This shape is commonly referred to as the longitudinal arch. Another arch commonly referred to as the transverse arch (metatarsal) also exists in about the same area in a perpendicular direction that runs laterally across the width of the foot.

The plantar fascia 110 serves the vital role of maintaining the shape of the two anatomical arches of the foot, the transverse arch and the longitudinal arch. As illustrated in FIGS. 1 and 2, the plantar fascia 110 runs across the bottom of the foot 100 from the heel 101 to the ball 102 and spreads out across the width of the foot 100. As longitudinal and lateral tensile stresses are produced in the bottom of the foot 100, the plantar fascia 110 absorbs the tensile forces and maintains the shape of the two anatomical arches.

For example, while standing or while in motion, forces experienced by the foot 100 act in a direction which tends to flatten the arches. The stress line 300 in FIG. 2 shows an approximation of the line of forces transferred through foot 100 during typical motion. As shown in FIG. 2, the stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

If the tension on the plantar fascia 110 becomes excessive, the plantar fascia 110 may be damaged and produce a condition called plantar fasciitis. Plantar fasciitis is a painful medical condition resulting from inflammation of the plantar fascia 110. The plantar fascia 110 is thick and essentially inelastic. Overstressing the plantar fascia 110 may produce tears in the plantar fascia 110 or separate the plantar fascia 110 from bone and other surrounding materials. Tearing and separation of the plantar fascia 110 produces the painful inflammation known as plantar fasciitis. Frequently, the inflamed areas 305 are along the arch of the foot 100 or near the heel 101 of the foot 100 as shown in FIG. 2.

Plantar fasciitis may be quite debilitating in that everyday activities such as walking and standing may be very painful. Typical treatments for plantar fasciitis may involve oral anti-inflammatories, ice packs, bedrest, stretching, steroid injections, night splints and wedge-shaped arch supports. In extreme cases, treatment of plantar fasciitis may require corrective surgery.

For example, a design for an orthotic device for treatment of plantar fasciitis is disclosed in Gleason, U.S. Pat. No. 5,865,779. The device of Gleason is an elastic sock that is worn on a patient's foot. The elastic sock exerts compressive forces along the longitudinal and transverse axes of the patient's foot.

While some patients may be willing to wear an elastic sock, the elastic sock is both inconvenient and cumbersome. In order to be installed on the foot, the elastic sock must be stretched to fit over the heel and toe of the foot. Because the sock is elastic, the sock allows the foot to move and stretch. Consequently, the plantar fascia may still be subjected to excessive tensile forces during the critical heeling process. Re-subjecting the plantar fascia to tensile forces before it has completely healed may re-aggravate damaged portions of the plantar fascia and undermine the healing process.

In addition, the elastic sock is meant to be worn multiple times and may require regular cleaning to avoid odors and foot infections. Also, the sock may not fit inside a shoe while being worn and may be considered unsightly while walking around with bare feet. Consequently, the elastic sock does not prevent excessive stretching of the plantar fascia and is both inconvenient and cumbersome.

Another typical example of treatment for plantar fasciitis includes medical personnel strapping strips of tape to the bottom of an injured foot. Strips of tape are applied at various angles across the bottom of the foot. The tape is difficult to remove from the rolls and bunches up during the taping process. Thus, care must be exercised during the application of the tape to avoid blister-causing wrinkles in the tape and other problems.

As the patient walks with the taped foot, the tape works loose and stretches with time. In addition, the tape cannot be effectively applied by the patient to the patient's own foot and requires application by another individual such as a trained medical technician. Consequently, taping the foot is cumbersome, inefficient, and ineffective in preventing excessive stretching of the plantar fascia.

Sometimes when current methods of treatment for plantar fasciitis are ineffective, expensive surgical procedures are required to relieve the pain of plantar fasciitis. To get at the plantar fascia, surgeons may perform either an endoscopic procedure requiring small incisions or conventional direct visualization requiring the underside of the foot to be opened up. With either painful procedure, scars may result and recovery time may be from weeks to months.

Even with treatment, improper treatment of plantar fasciitis may lead to other medical problems. For example, if inflammation near the heel is allowed to continue for a long period of time, calcium deposits may build-up in the damaged region. As the calcium builds-up, bony outcroppings may develop in the heel that are commonly referred to as "heel spurs". The longer the plantar fascia remains inflamed around the heel, the stronger the conditions are for the development of heel spurs. Protrusion of the heel spurs into the surrounding tissue may result in a cycle of irritation, inflammation, and pain known as heel spur syndrome.

Heel spur syndrome is commonly treated with a surgical procedure requiring removal of the heel spurs from within the foot. An endoscopic procedure is typically not used for removal of heel spurs and open surgery is typically required. Recovery time from such surgery may range from weeks to months, during which time the patient has to curtail the amount of stress placed on the foot.

Thus, it may be highly desirable to have a system for avoiding and/or treating the pain of plantar fasciitis. It may also be highly desirable to have a system for treating plantar fasciitis that is economical and may be easily applied by the patient. It may also be highly desirable to have a system for treating plantar fasciitis that is discretely attached to the sole of the patient's foot and includes a substantially stretch resistant material to reduce tensile forces in the plantar fascia.

BRIEF SUMMARY OF THE INVENTION

A preferred embodiment of the present invention provides a system for treatment of plantar fasciitis. The system is economical and may be easily applied by a patient.

A stretch resistant plantar fascia support system is provided with a foot sole support. The foot sole support may be a thin one-piece device made of a uniform substantially stretch resistant material of a uniform thickness or the foot sole support may be made with a strip of substantially stretch resistant material bounded by a more deformable material. The foot sole support may be shaped to conform to the outline of the bottom of a foot or shaped to cover only a portion of the bottom of a foot. Straps and tabs may be included with the foot sole support for providing additional support to both the foot and other portions of the stretch resistant plantar fascia support system. The foot sole support, straps, and tabs have adhesive applied to portions of the surface of the foot sole support, the straps, and the tabs. Removable protective covers are applied over the adhesive and the removable protective covers may include indicia signifying the order in which the portions of the stretch resistant plantar fascia support system are to be applied to the foot.

To relieve the symptoms of plantar fasciitis, tensile stresses in the plantar fascia are reduced. The tensile stresses in the plantar fascia are reduced by adhering the foot sole support to the foot of the patient. The foot sole support absorbs tensile stress in the lower foot thereby reducing the tensile stress experienced by the plantar fascia and surrounding tissues. The straps and tabs may be attached in the prescribed order to the foot sole support and wrapped around or attached to portions of the foot to provide additional support to the stretch resistant plantar fascia support system.

Certain embodiments of the present invention include an article of manufacture that is a kit for at least one of providing anatomical support to the arch of the foot, treating arch pain, treating heel pain, increasing tissue healing and rehabilitation in a human afflicted with plantar fasciitis, and preventing injury to the plantar fascia. The kit includes a sheet of material having a support layer, an adhesive layer for applying at least a portion of the support layer to the foot, and a cover layer that covers at least a portion of the adhesive layer and that may be removed from the support layer and adhesive layer. The kit includes instructions for applying the support layer to the foot for at least one of supporting the arch, reducing stress on the plantar fascia or surrounding tissues, and treating plantar fasciitis. The kit includes packaging carrying the sheet and instructions.

Certain embodiments of the present invention include a kit for managing foot pain. The kit includes a sheet of material configured to be affixed to at least a portion of a foot, the sheet including a stretch resistant support layer joined to a cover layer by adhesive, wherein the cover layer is removed from the adhesive and the support layer is affixed to the portion of the foot by the adhesive. The kit includes instructions instructing how to apply the support layer to the portion of the foot.

Certain embodiments of the present invention include a process for controlling stress on a plantar fascia of a foot. The process includes providing a sheet of material and instructions for using the sheet of material to control stress on the plantar fascia, wherein the sheet has a stretch resistant support layer joined to a cover layer by adhesive. The process includes reviewing the instructions, conforming the sheet of material to the shape of a portion of a foot, removing the cover layer from the adhesive and the support layer, applying the support layer to the portion of the foot such that the adhesive retains the support layer to the portion of the foot, and adjusting the support layer to the portion of the foot where the applying step results in an unsatisfactory application.

Certain embodiments of the present invention include an article of manufacture for managing foot pain. The article includes a sheet of material including a substantially stretch resistant Rayon support layer having a thickness of less than 15 mils, an adhesive layer, and a release liner. The sheet of material is configured to be conformed with cutting tools to the shape of at least a portion of the human foot. The support layer of the conformed sheet is affixed to the foot by the adhesive layer in order to control stress on the plantar fascia or support the arch of the foot.

Certain embodiments of the present invention include a sheet of material having a Rayon layer having a nominal thread count of 3600, a hypoallergenic adhesive on the layer, and a release liner affixed to the adhesive. The sheet of material has a thickness of less than 30 mils.

DETAILED DESCRIPTION OF PREFERRED EMBODIMENTS

Figure 1:
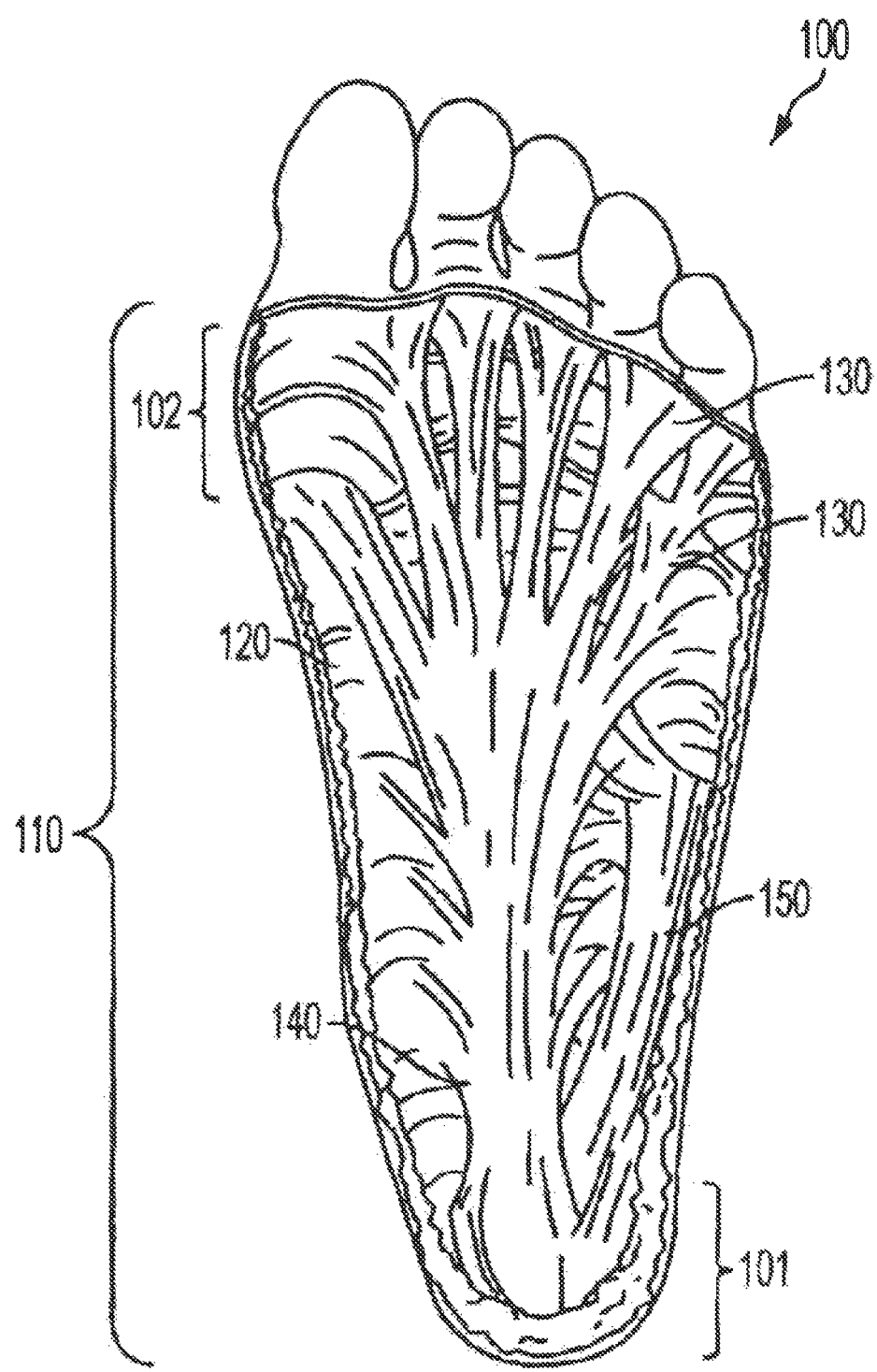
FIG. 1 illustrates parts of a plantar fascia in a dissected bottom view of a human foot.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

Figure 3:
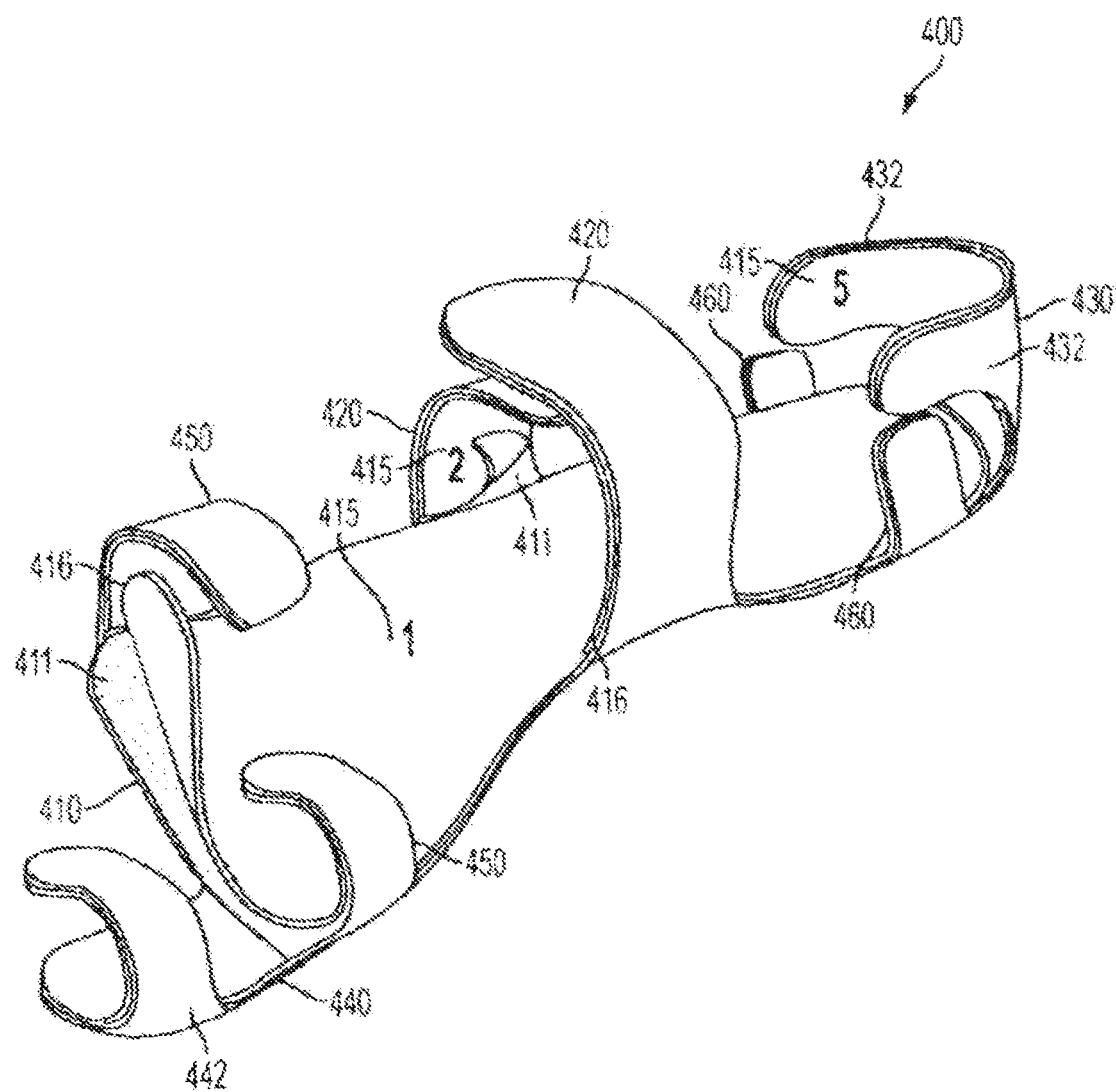
FIG. 3 illustrates a stretch resistant plantar fascia support system in accordance with an embodiment of the present invention.

FIG. 3 illustrates a stretch resistant plantar fascia support system 400 in accordance with an embodiment of the present invention. The stretch resistant plantar fascia support system 400 includes a foot sole support 410, an adhesive layer 411, indicia 415, removable protective covers 416, arch straps 420, heel strap 430, heel strap tabs 432, toe strap 440, toe strap tab 442, front straps 450, and heel tabs 460.

The arch straps 420, the heel strap 430, the toe strap 440, the front straps 450, and the heel tabs 460 are connected to the foot sole support 410. The arch straps 420 project from the sides of the foot sole support 410 approximately midway along the longitudinal axis of the foot sole support 410. The heel strap 430 projects from the back edge of the foot sole support 410 and the heel strap tabs 432 project from the sides of the heel strap 430. The toe strap 440 projects from the front edge of the foot sole support 410 and the toe strap tab projects from a side of the toe strap 440. The front straps 450 project from the sides of the of the foot sole support 410 adjacent the front edge of the foot sole support 410. The heel tabs 460 project from the sides of the foot sole support 410 adjacent the back edge of the foot sole support 410.

The adhesive layer 411 is applied to the top or inner surface of the foot sole support 410, the arch straps 420, the heel strap 430, the toe strap 440, the front straps 450, and the heel tabs 460. The removable protective covers 416 are removably adhered to the adhesive layer 411. Indicia 415 are printed on the removable protective covers 416.

In operation, the stretch resistant plantar fascia support system 400 is adhesively attached to a human foot 100. To adhesively attach the stretch resistant plantar fascia support system 400 to the human foot 100, the removable protective cover 416 adhered to the top of the foot sole support 410 is removed. The foot sole support 410 is pressed against the outer skin surface 178 on the bottom of the human foot 100.

Adhesion of the foot sole support 410 to the outer skin surface 178 on the bottom of the human foot 100 prevents extension and stretching of tissue on the bottom of the foot. By restricting extension of the tissue on the bottom of the foot, the level of tensile stress on the plantar fascia is reduced.

In the alternative, adhesive may be applied to select portions of the foot sole support 410, the straps 420, 430, 440 and 450, and the tabs 432, 442, and 462. For example, to reduce the chance of irritation to sensitive skin regions along an arch of the foot or to accommodate users with high arches, adhesive may only be applied to the portion of the foot sole support 410 contacting the ball of the foot and the heel of the foot.

In another alternative embodiment, adhesive may be applied to the sole of the foot. For example, adhesive sprays may be used to spray an adhesive layer on select portions of the foot. If a strong enough adhesive spray is used that would hold the foot sole portion 410 in place, then the stretch resistant plantar fascia support system 400 may be supplied without the adhesive layer 411 and removable protective covers 416.

To help maintain the position of the foot sole support 410 on the bottom of the human foot 100 and further reduce tensile stress on the plantar fascia, the arch straps 420 may be wrapped laterally over the arch of the foot. To install the arch straps 420, the removable protective cover 416 adhered to the inner surface of the arch straps 420 is removed. The arch straps 420 are then wrapped up and over the top of the foot 100. To secure the arch straps 420 in place, one of the arch straps 420 may overlap another arch strap 420 and be adhered to the outer surface of the other arch strap 420.

In the alternative, only one arch strap 420 may be used. With only one arch strap 420, the arch strap 420 may wrap laterally over the top of the arch and adhere to the bottom surface of the foot sole support 410 on the opposite side of the foot 100.

In another alternative embodiment, only one arch strap 420 may be used and the arch strap 420 may be separate and distinct from the foot sole support 410. With the foot sole support 410 already installed on the bottom of the foot 100, the arch strap 420 may be adhered to the foot sole support 410 on one side of the foot 100. The arch strap 420 may then be wrapped laterally over the arch, down the opposite side of the foot 100, and adhered to the foot sole support 410 on the opposite side of the foot 100.

Installation of the arch straps 420 also reduces stress on the plantar fascia. As presented earlier with regard to FIG. 2, the stress line 300 in FIG. 2 resembles an archer's bow. The stress line 300 passes through the talus 162, the navicular 164, the cuneiform 166, and the cuboid 168. Laterally wrapping the arch straps 420 over and around the top of the foot near the arch provides resistance to vertical and lateral movement of the talus 162, the navicular 164, the cuneiform 166, and the cuboid 168. Provision of the resistance to vertical and lateral movement by the arch straps 420 reduces flexure of the "bow" and related changes in stress on the plantar fascia.

To provide extra support to the heel of the human foot 100 and help maintain the position of the foot sole support 410 on the bottom of the human foot 100, the heel strap 430 may be adhered to the heel of the foot 100. To further support the heel and help maintain the position of the foot sole support 410, the heel strap 430 includes heel strap tabs 432. To install the heel strap 430 and heel strap tabs 432, the removable protective cover 416 adhered to the inner surface of the heel strap 430 and heel strap tabs 432 are removed. The heel strap 430 is then pressed against the back of the heel of the foot 100 and secured in place by contact between the adhesive layer 411 and the outer skin surface 178. The heel strap tabs 432 are pressed against the outer skin surface 178 along the sides of the heel of the foot 100.

In an alternative embodiment, the stretch resistant plantar fascia support system 400 may include a heel strap 430 without heel strap tabs 432. The heel strap 430 may be installed as described above by removing the removable protective cover 416 and adhering the heel strap 430 to the back of the heel.

Installation of the heel strap 430 provides extra support to the heel and helps maintain the position of the foot sole support 410. Adhesion of the heel strap 430 to the back of the heel provides an anchor point for the rear portion of the foot sole support 410. During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the heel strap 430 to the heel of the foot 100 provides extra resistance to lateral and longitudinal forces that may otherwise cause the foot sole support 410 to shift around on the bottom of the foot.

Additionally, the heel strap 430 provides extra support to the heel of the foot 100. The human foot has a complex structure of tissue and bones. Tissues in the heel interact with other tissues in the foot to transfer forces exhibited during walking. As shown in FIG. 1, portions of the plantar fascia attach to the heel and other tissues that continue up around the back of the heel. Through these attachments, tissues in the heel transfer forces to and from the plantar fascia. Providing extra support to the heel of the foot 100 reduces the amount of stress transferred between the heel and the plantar fascia.

The stretch resistant plantar fascia support system 400 also includes heel tabs 460. Similar to the heel strap 430, the heel tabs 460 assist in maintaining the position of the foot sole support 410. To install the heel tabs 460, the removable protective covers 416 adhered to the inner surface of the heel tabs 460 are removed. The heel tabs 460 are then pressed against the sides of the heel of the foot 100 and secured in place by contact between the adhesive layer 411 and the outer skin surface 178. As the foot sole support 410 is subjected to lateral and longitudinal forces, the heel tabs 460 provide additional resistance to the lateral and longitudinal forces to help maintain the installed position of the foot sole support 410.

The stretch resistant plantar fascia support system 400 also includes front straps 450. The front straps 450 assist in maintaining the position of the foot sole support 410 and provide extra support to the area near the ball of the foot 100. To install the front straps 450, the removable protective covers 416 adhered to the inner surface of the front straps 450 are removed. The front straps 450 are then wrapped up and over the top of the foot 100. To secure the front straps 450 in place, one of the front straps 450 may overlap another front strap 450 and be adhered to the outer surface of the other front strap 450.

In the alternative, only one front strap 450 may be used. With only one front strap 450, the front strap 450 may wrap laterally over the top of the foot 100 and adhere to the bottom surface of the foot sole support 410 on the opposite side of the foot 100.

In another alternative embodiment, only one front strap 450 may be used and the front strap 450 may be separate and distinct from the foot sole support 410. With the foot sole support 410 already installed on the bottom of the foot 100, the front strap 450 may then be adhered to the foot sole support 410 on one side of the foot 100. The front strap 450 may then be wrapped laterally over the foot 100, down the opposite side of the foot 100, and adhered to the foot sole support 410 on the opposite side of the foot 100.

During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the front straps 450 near the ball of the foot 100 provides extra resistance to lateral and longitudinal forces that may otherwise cause the foot sole support 410 to shift around on the bottom of the foot.

Installation of the front straps 450 also reduces stress on the plantar fascia. As shown in FIG. 1, portions of the plantar fascia attach to the ball of the foot and other portions such as the superficial tracts 130 continue past the ball of the foot 100 to the toe region. Due to the complex structure of tissue and bones in the human foot, tissues near the ball of the foot interact with other tissues in the foot to transfer forces induced during walking. Through the attachments near the ball of the foot, tissues near the ball of the foot transfer forces to and from the plantar fascia 110. Providing extra support near the ball of the foot 100 reduces the amount of stress transferred between the ball of the foot and the plantar fascia 110.

The stretch resistant plantar fascia support system 400 includes a toe strap 440. Installation of the toe strap 440 assists in maintaining the position of the foot sole support 410. To install the toe strap 440, the removable protective cover 416 adhered to the inner surface of the toe strap 440 is removed. The toe strap 440 is then pressed against the underside of the toe and the adhesive layer secures the toe strap 440 in place.

To further secure the toe strap 440 in place, the toe strap 440 includes a toe strap tab 442. To install the toe strap tab 442, the removable protective cover 416 adhered to the inner surface of the toe strap tab 442 is removed. The toe strap tab 442 is then wrapped up and over the top of the toe of the foot 100. The toe strap is wrapped back down the opposite side of the toe and adhered to the underside of toe strap 440 on the opposite side of the toe.

In the alternative, more than one toe strap tab 442 may be attached to the toe strap 440. For example, a second toe strap tab may be positioned opposite the toe strap tab shown in FIG. 3 on the opposite side of the toe strap 440. To install the toe strap tabs 442, the removable protective cover 416 adhered to the inner surface of the toe strap tabs 442 is removed. The toe strap tabs 442 are then wrapped up and over the top of the toe. To secure the toe strap tabs 442 in place, one of the toe strap tabs 442 may overlap the other toe strap tab 442 and be adhered to the outer surface of the other toe strap tab 442 similar to the arch straps 420 shown in FIG. 3.

In another alternative embodiment, only one toe strap tab 442 may be used and the toe strap tab 442 may be separate and distinct from the toe strap 440 and the foot sole support 410. With the toe strap 440 already installed on the bottom of the toe, the toe strap tab 442 may then be adhered to the toe strap 440 on one side of the toe. The toe strap tab 442 may then be wrapped laterally over the toe, down the opposite side of the toe, and adhered to the toe strap 440 on the opposite side of the toe.

The stretch resistant plantar fascia support system 410 may also include indicia 415 printed on the removable protective covers 416. The indicia 415 may represent instructions for the installation of the stretch resistant plantar fascia support system 410. For example, the indicia 415 may be numerical or alphabetic designations for the order in which portions of the stretch resistant plantar fascia support system 410 are to be installed. In FIG. 3, the indicia 415 on the removable protective cover 416 over the foot sole support 410 is the number "1" designating that the foot sole support 410 is to be installed first. The indicia 415 on the removable protective cover 416 on the arch straps 420 is the number "2" designating that the arch straps 420 are the next portion to be installed. Thus, the indicia may be increased or decreased incrementally to designate the order in which the portions of the stretch resistant plantar fascia support system 400 are to be installed.

In the alternative, letters or words may be used instead of numerals as the indicia 415 to designate the order in which the portions of the stretch resistant plantar fascia support system 400 are to be installed. For examples, letters "A", "B", and "C" or the words "First", "Second", and "Third" may be used to designate the order in which the first three portions are to be installed.

In the alternative, the indicia 415 may be printed on the various portions of the stretch resistant plantar fascia support system 400. For example, if an adhesive spray is applied to the skin rather than using an adhesive layer 411 and removable protective covers 416, the indicia 415 may be printed on the inner surface of components such as the foot sole support 410 and a consumer may still be able to see the indicia and determine the order of application.

In an alternative embodiment, the stretch resistant plantar fascia support system 400 may include the foot sole support 410 without the arch straps 420, the heel strap 430, the toe strap 440, and front strap 450 and the heel tabs 460. Similar to the embodiment shown in FIG. 3, the foot sole support 410 would be adhesively applied to the bottom surface of the foot.

In the alternative, the stretch resistant plantar fascia support system 400 may include various combinations of the arch straps 420, the heel strap 430, the toe strap 440, and front straps 450 and the heel tabs 460. For example, an alternative embodiment of the stretch resistant plantar fascia support system 400 may include the foot sole support 410 with arch straps 420. Another alternative embodiment of the stretch resistant plantar fascia support system 400 may include the foot sole support 410 with the heel strap 430. Yet another alternative embodiment of the stretch resistant plantar fascia support system 400 may include the foot sole support 410 with the toe strap 440. Consequently, various alternative embodiments of the stretch resistant plantar fascia support system 400 may be used that include the foot sole support 410 with different combinations of the arch straps 420, the heel strap 430, the toe strap 440, and front strap 450 and the heel tabs 460.

Figure 4:
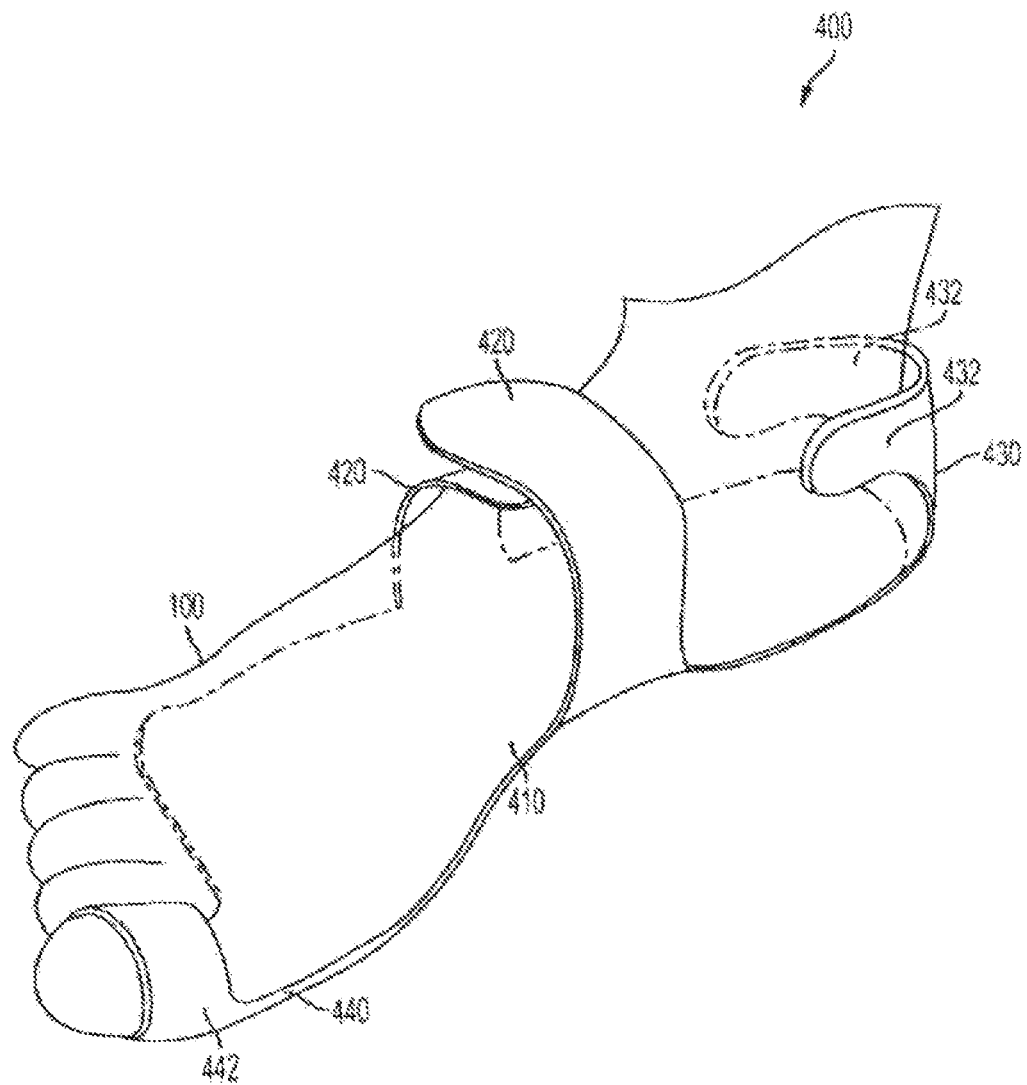
FIG. 4 illustrates a stretch resistant plantar fascia support system in accordance with an alternative embodiment of the present invention.

FIG. 4 illustrates a stretch resistant plantar fascia support system 500 as an alternative embodiment of the stretch resistant plantar fascia support system 400 of FIG. 3 installed on a human foot. The alternative embodiment shown in FIG. 4 includes a foot sole support 410, arch straps 420, heel strap 430, heel strap tabs 432, toe strap 440, and toe strap tab 442.

As shown in FIG. 4, the foot sole support 410 may be adhered to the sole of the foot to provide additional support to the region underneath the plantar fascia. The arch straps 420 may be wrapped around the top of the foot to provide additional support near the arch. The heel strap 430 may be adhered to the back of the heel to provide additional support to the heel and stabilize the position of the foot sole support 410. The toe strap 440 may be adhered to the bottom of the toe and the toe strap 442 wrapped around the toe to provide additional support to the toe and stabilize the position of the foot sole support 410.

Figure 2:
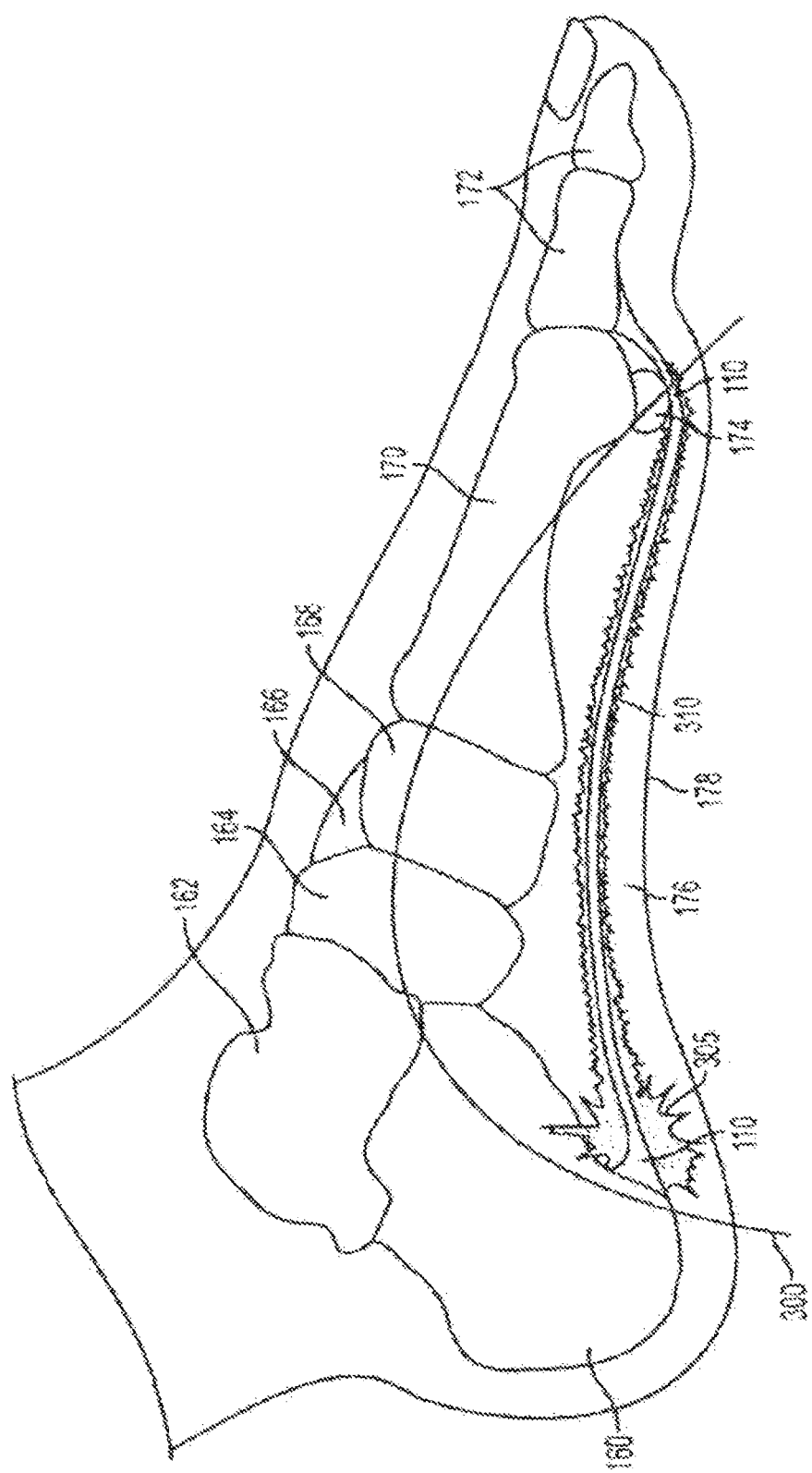
FIG. 2 illustrates a simplified side view of tissue and bone structure in the human foot.
Figure 5:
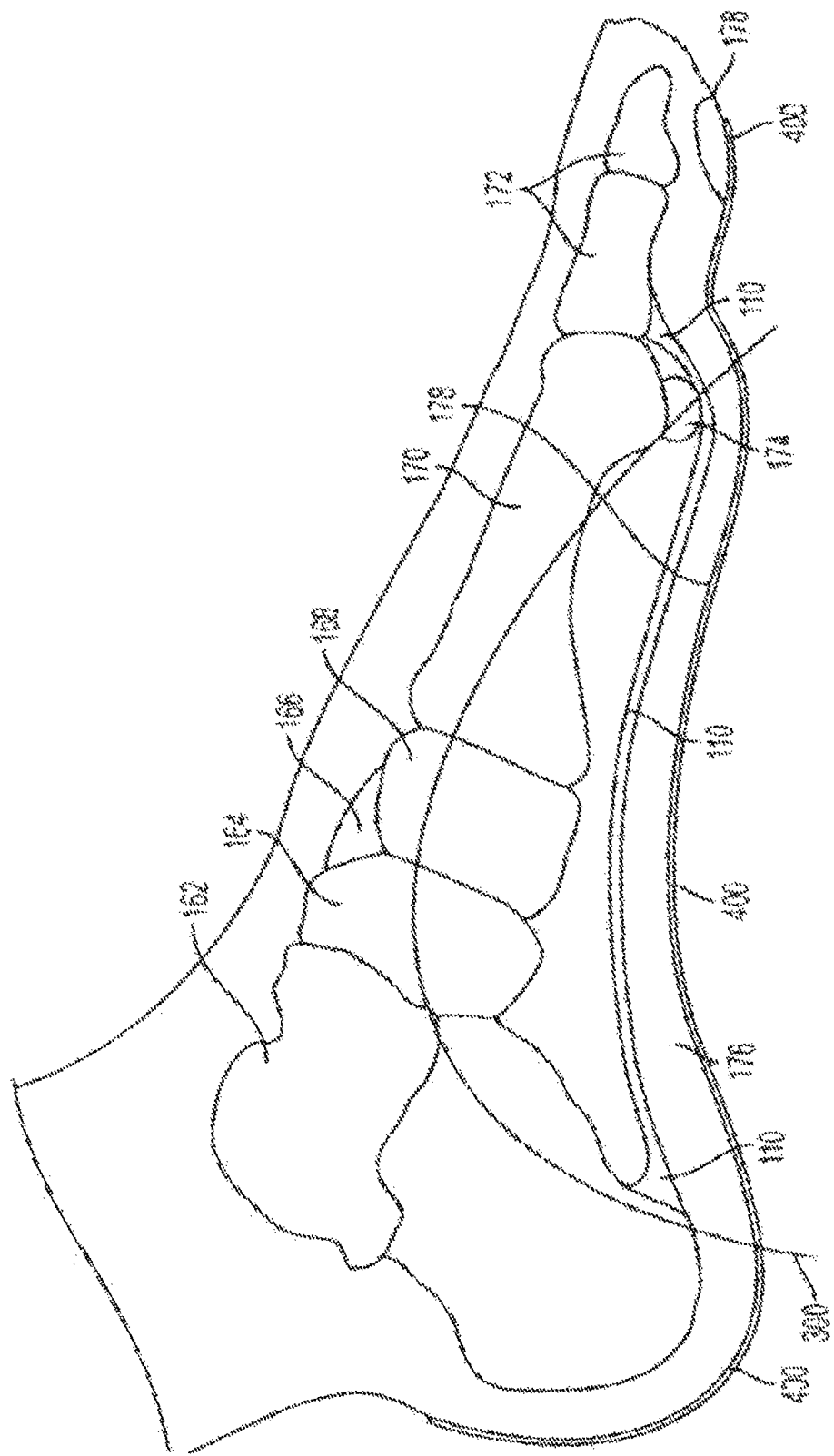
FIG. 5 illustrates stresses in the human foot with a stretch resistant plantar fascia support system installed in accordance with an embodiment of the present invention.

FIG. 5 illustrates stresses in the human foot 100 shown in FIG. 2 with a stretch resistant plantar fascia support system 400 attached to the human foot 100 in accordance with an embodiment of the present invention. As described previously with regard to FIG. 2, the stress line 300 shows an approximation of the line of forces transferred through a foot 100 during typical motion. The stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

To reduce the tensile forces on the plantar fascia 110, the stretch resistant plantar fascia support system 400 is attached to the bottom of the foot. As depicted in FIG. 5, the stretch resistant plantar fascia support system 400 is analogous to another string in the archer's bow connected in parallel with the plantar fascia 110. Tensile forces induced in the bottom of the foot are shared between the plantar fascia 110 and the stretch resistant plantar fascia support system 400. Consequently, tensile force in the plantar fascia 110 is reduced and damaged areas may heal with a reduced likelihood of being subjected to excessive tensile forces.

Thus, a stretch resistant plantar fascia support system using a substantially stretch resistant material may be conveniently and easily applied to the foot of a patient by the patient for the treatment of plantar fasciitis. For example, the entire foot sole support, or portions of the foot sole support, of the stretch resistant plantar fascia support system may be made of a flexible material that exhibits less than 15 percent elongation when subjected to a 25 lb tensile load under test conditions specified in ASTM D3759. In addition, a material with a ratio of elongation to tensile strength (lb/in-width) that is less than 0.9 may be used to provide a balanced combination of strength and resistance to elongation.

Additionally, to simplify manufacturing and reduce cost, the stretch resistant plantar fascia support system may be made of a uniform material supplied in sheet form. Portions of the stretch resistant plantar fascia support system may be cut or punched from sheets of material. For example, the foot sole support may be shaped to resemble the outline of the sole of a left or right foot. Alternatively, the foot sole support may also be shaped for interchangeable use on either a left or right foot.

The stretch resistant plantar fascia support system may then be packaged individually, in multiples, or in a continuous package such as a roll with individual patches separated by perforations. For example, the individual packaging could be used by the average consumer for everyday use around the home. The continuous packaging could be used in high use situations such as locker rooms where access to stretch resistant plantar fascia support systems is required by multiple people.

Alternatively, the invention includes an article of manufacture that is an anatomical foot support kit for treating plantar fasciitis and other kinds of foot pain. The kit includes at least one sheet of stretch resistant material that can be adapted for application to the user's foot as a support system to treat plantar fasciitis, instructions that instruct the user on how to apply and use the support system, and packaging that allows for the distribution of the support system and instructions.

Figure 6:
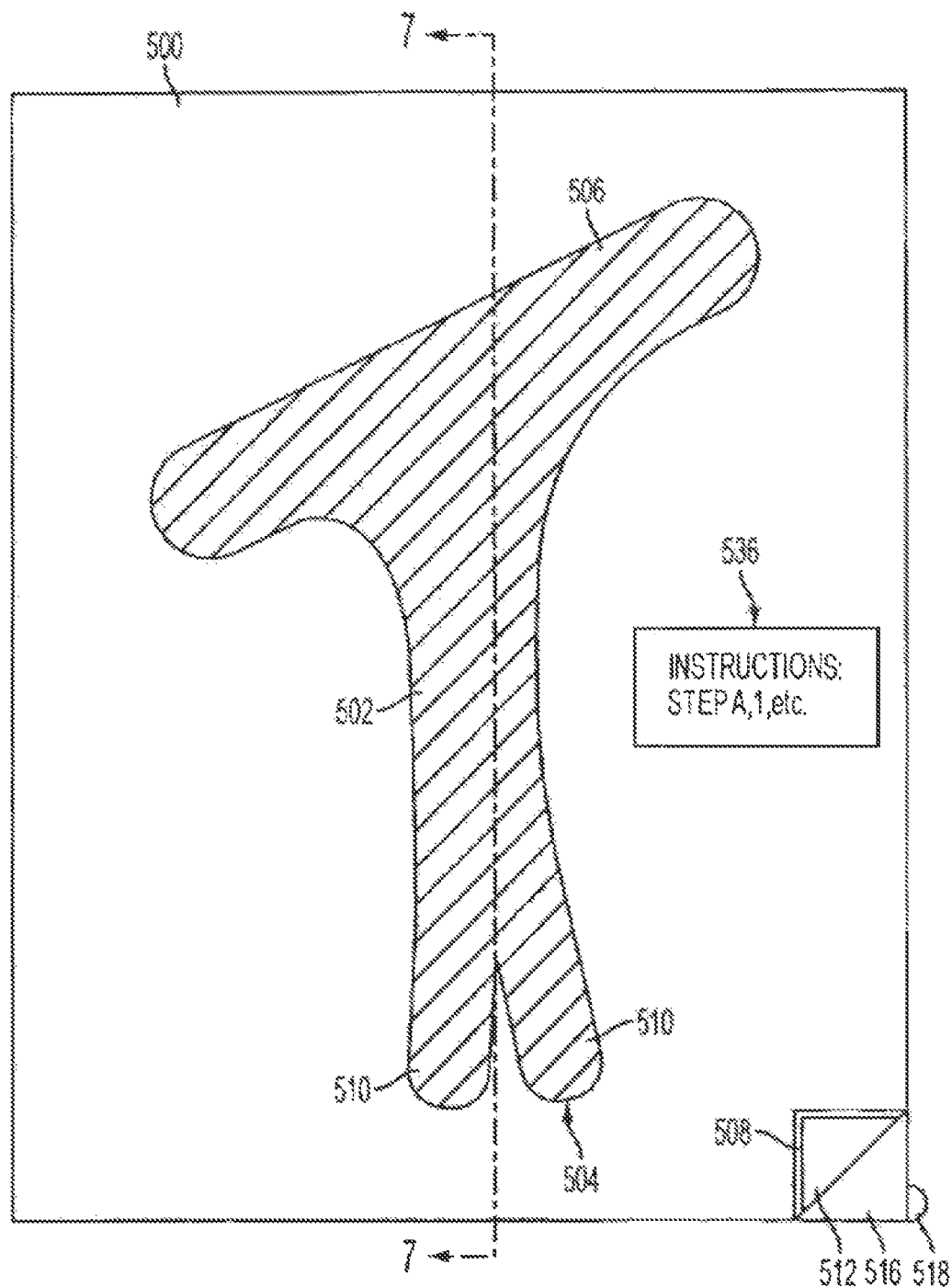
FIG. 6 illustrates a top view of a sheet of material containing a support system in accordance with an embodiment of the present invention.

FIG. 6 illustrates a top view of a sheet 500 of material. A support system 504 is formed and removed from the sheet 500 of material for use as the stretch resistant plantar fascia support system on the user's foot. The support system 504 is shaped to be applied to the user's foot or a portion of the foot. The support system 504 includes a sole portion 502 shaped for application to the sole of a foot, a ball strap 506 and heel tabs 510 for retaining the sole portion 502 to the foot or a portion of the foot. Alternatively, support system 504 may be shaped like the support system 400 shown in FIGS. 3 and 4 or have any number of other shapes for being connected to the user's foot. The support system 504 may be shaped for either a left or a right foot. The support system 504 may be pre-cut or perforated into the sheet 500 for the user to punch out of the sheet 500. Alternatively, the user may use cutting tools to cut the support system 504 from the sheet 500 along an outline imprinted on the sheet 500 or cut by freehand to suit the user's particular foot shape. The sheet 500 may be large enough to include more than one support system 504. Alternatively, the sheet 500 may be smaller such that the user may remove multiple smaller portions of a single support system 504 from the sheet 500 for application to the foot. The sheet 500 may be manufactured by a number of different techniques. Additionally, the sheet 500 may be pre-cut or perforated to form the support system 504 by a number of different techniques. By way of example only, the sheet 500 may be cut by die-cutting or laser cutting.

Figure 7:
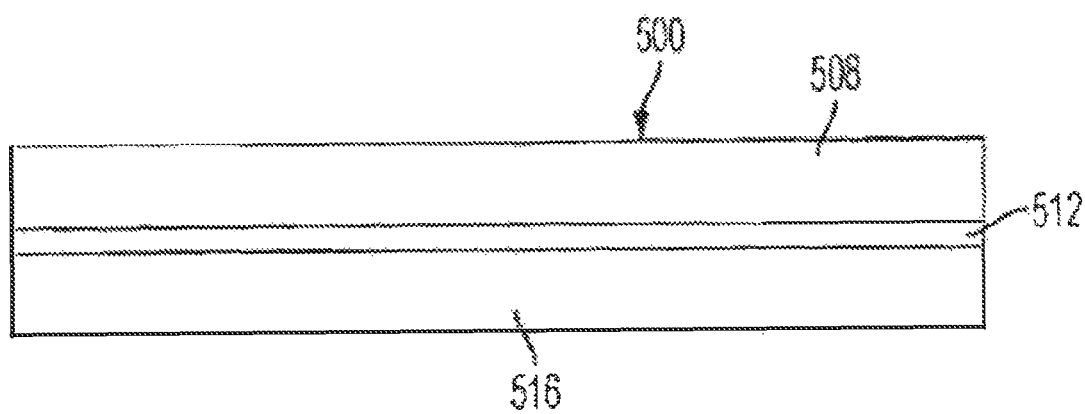
FIG. 7 illustrates an enlarged cross-sectional side view of the sheet of FIG. 6 taken along line 7-7.

FIG. 7 illustrates an enlarged cross-sectional side view of the sheet 500 of FIG. 6 taken along lines 7-7. Similar to the support system 400 of FIG. 3, the sheet 500 includes a backing or support layer 508, an adhesive layer 512, and a removable protective cover layer or release liner 516. Alternatively, the adhesive layer 512 may be an adhesive that is applied or coated to the support layer 508. The sheet 500 has a generally uniform thickness. By way of example only, the sheet 500 may have a thickness of up to ⅜ inch. By way of example only, the thickness of the sheet 500, including all three layers 508, 512, and 516, may be less than 60 mils. By way of example only, the thickness of the sheet 500, including all three layers 508, 512, and 516, may be less than 45 mils. The relative thicknesses of the layers 508, 512, and 516 may vary from each other differently from what is shown in FIG. 7.

Returning to FIG. 6, the support layer 508 is made of a material having the mechanical integrity to provide support under cyclic loading for the duration of application to the user's foot without excessive elongation, fraying or other forms of degradation. The support layer 508 is sufficiently flexible so that it can conform to the shape of the section of the foot to which it is adhesively connected and provide structural support to the body part. The material of the support layer 508 may be made of a single layer or a plurality of layers. By way of example only, the support layer 508 may be less than 15 mils thick and by further way of example may be less than 5 mils thick. The support layer 508 more easily conforms to the shape of the foot where the material of the support layer 508 is thinner. Additionally, the support layer 508 may also be compliant and non-irritating to the skin of the user. Furthermore, the support layer 508 may be of any color. For example, the support layer 508 may be tan or a skin-tone color such that the support layer 508 is less visible when applied to the user's foot.

The material of the support layer 508 is substantially stretch resistant in at least one direction. By way of example only, the support layer 508 may exhibit less than 15 percent total elongation in at least one direction when subjected to a 25 lb tensile load under test conditions specified in ASTM (American Society for Testing and Materials) D3759. In addition, by way of example only, the support layer 508 may have a ratio of elongation to tensile strength (lb/in-width) that is less than 0.9 to provide a balanced combination of strength and resistance to elongation. By way of example only, the support layer 508 may have a tensile strength of greater than 10 lb/in-width per ASTM D-1000 and by further way of example may have a tensile strength of greater than 20 lb/in-width per ASTM D-1000.

The support layer 508 may be manufactured from a wide range of materials such as woven and non-woven materials, polymeric materials such as apertured formed thermoplastic films, or apertured plastic films, synthetic or natural fibers, or a combination of materials. By way of example only, the support layer may be made of a woven rayon microfiber with a 3600 thread count and/or thickness of less than 30 mils, or alternatively less than 15 mils, such that the stretch resistant plantar fascia support system is thin enough to comply with the contours of the foot and strong enough to provide adequate strength.

Additionally, the support layer 508 may be breathable. By way of example only, the support layer 508 may have a moisture vapor transfer rate (MVTR) of at least 100 g/24 h/m.sup.2. By way of example only, the support layer 508 may have a MVTR of greater than 400 100 g/24 h/m.sup.2.

The adhesive layer 512 includes an adhesive that provides the requisite degree of adhesion to hold the support layer 508 against the user's foot for the duration of use and is relatively easy to remove at the end of use. The adhesive on the adhesive layer 512 is non-toxic and non-allergenic or hypoallergenic and may or may not be vapor permeable. The adhesive may provide enough tack such that the support layer 508 may be easily applied and re-adjusted to the foot if necessary. The adhesive is highly resistant to slippage or movement caused by the potentially high sheer stresses of the application. By way of example only, the adhesive layer 512 may be less than 10 mils thick, and by further way of example may be less than 5 mils thick. By way of example only, the adhesive may provide a holding strength of greater that 15 oz/in when tested according to a PSTC-3 (Pressure sensitive tape council) standard Adhesion-to-Steel 180 degree Peel test. By way of example only, the adhesive may provide a holding strength of greater that 30 oz/in when tested according to the Adhesion-to-Steel 180 degree Peel test.

The release paper 516 is provided over the adhesive layer 512. The release paper 516 should remain in place over the adhesive layer 512 until removed by the user. By way of example only, the release paper 516 may be made of 3.5 mil. 60# Kraft paper. The release paper 516 may include a tab 518 that can be pulled to easily remove the release paper 516 from the adhesive layer 512. Alternatively, to ease removal of the support layer 508 of the support system 504 from the release paper 516, the support layer 508 and the adhesive layer 512 that form the shape of the support system 504 may not be surrounded by any further support layers 508 or adhesive layers 512 on the release paper 516 such the surrounding release liner 512 is visible about the support system 504. Alternatively, the sheet 500 may be the shape of the support system 504 so that the support system 504 does not need to be removed from a larger sheet. Thus, the user can simply remove the release paper 516 from the sheet 500 in order to apply the support system 504.

Figure 8:
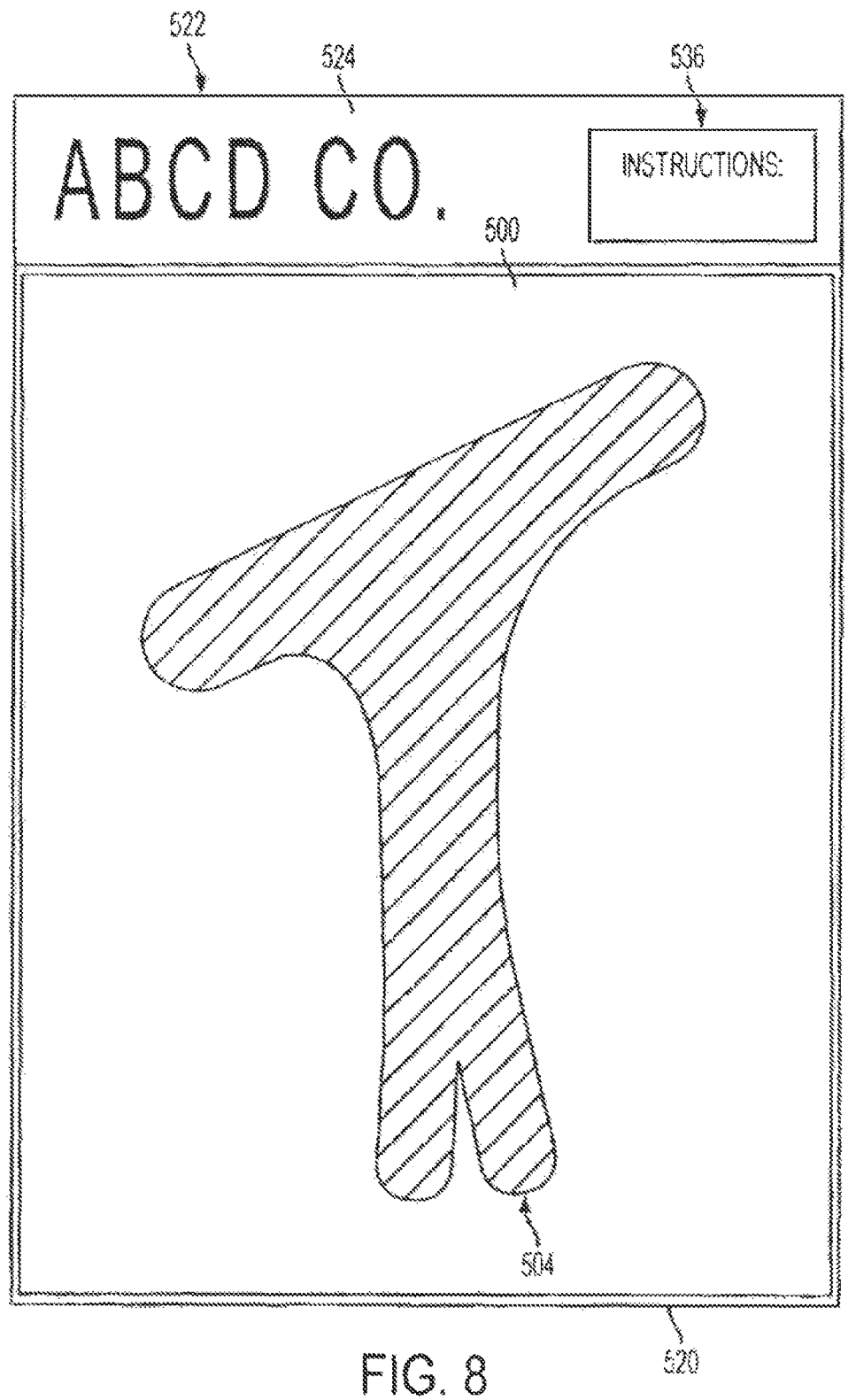
FIG. 8 illustrates a top view of a packaged anatomical foot support kit in accordance with an embodiment of the present invention.
Figure 9:
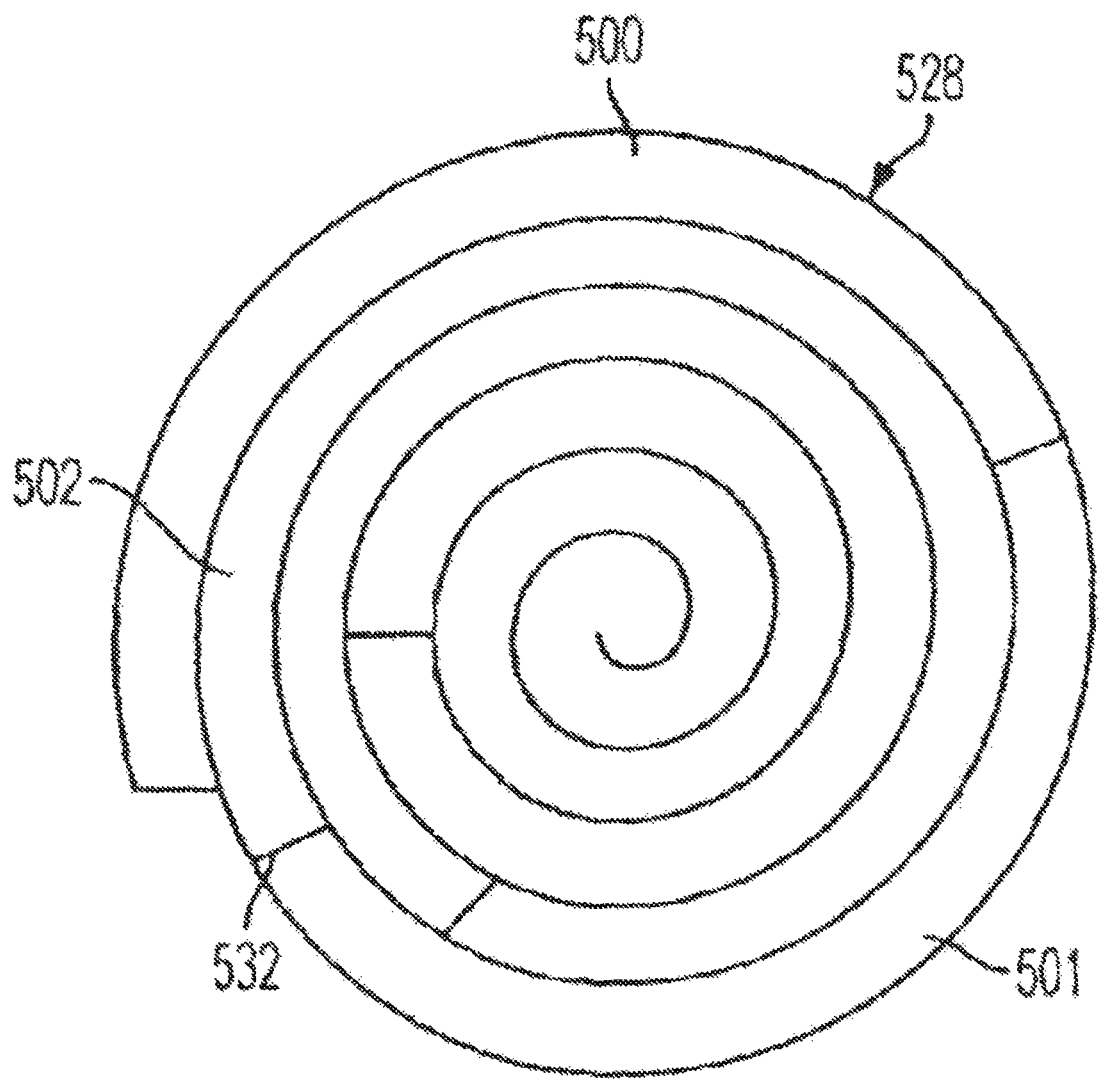
FIG. 9 illustrates a side view of an anatomical foot support kit in accordance with an embodiment of the present invention.

As shown in FIG. 8, the sheet 500 (or multiple sheets 500) may be provided in a package 522 for sales or distribution in stacked flat layers and sealed in a pouch or bag 520 with labeling 524. By way of example only, the bag 520 may be cellophane or another suitable material. Alternatively, as shown in FIG. 9, the sheet 500 (or multiple sheets 500) may be packaged by wrapping a plurality of sheets 500 about themselves in the shape of a roll 528. A specific sheet, bearing reference numeral 501, in a roll 528 is connected to an adjacent sheet, bearing reference numeral 502, in the roll 528 along a perforation 532. Alternatively, the user may unroll the sheets 500 and cut adjacent sheets 501 and 502 from each other. Alternatively, the roll 528 may include just one continuous sheet 500 wrapped about itself that the user may unwrap and cut where appropriate. The roll 528 may include a center spool (not shown) about which the sheet(s) 500 are wrapped. The roll 528 may be packaged in a labeled box or bag, or any number of other kinds of packaging.

Alternatively, the sheet 500 or multiple sheets 500 may be packaged in any number of other ways in boxes, bags, envelops, pouches, bottles, jars, cartons, packets, tubes, or any combination thereof or any number of other forms of packaging.

Figure 27:
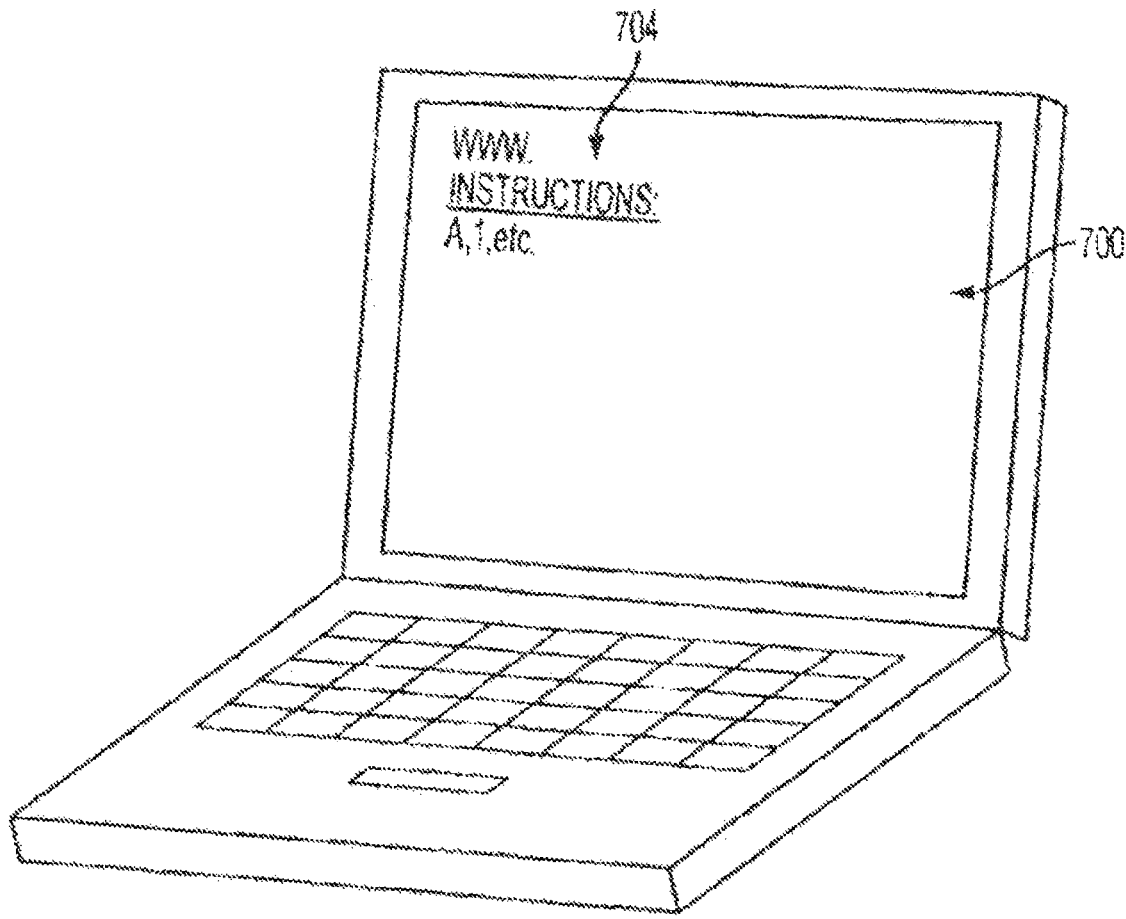
FIG. 27 illustrates a front view of a website showing instructions formed according to an embodiment of the present invention.

Returning to FIG. 6, instructions 536 are included with the sheet 500 instructing the user on how to apply and use the sheet 500 as a support system to treat plantar fasciitis. The instructions 536 instruct the user on how to cut or remove or shape the portion 504 to conform to the foot, and/or apply the portion 504 of material in a manner intended to provide anatomical support to the arch of the foot. As shown in FIG. 27, the instructions 536 may also direct the user to a specific computer internet website 700. The website 700 may provide a set of instructions 704 for cutting, removing, shaping and/or applying the portion 504 to the foot. The instructions 536 may also provide information on, or direct the user to a website 700 that provides information on, the causes and treatments of plantar fasciitis, and/or heel pain, and/or arch pain. Furthermore, the set of instructions 536 may contain, or direct the user to a website 700 that contains, other helpful and commonly known information regarding diagnosing or treating plantar fasciitis, heal pain and arch pain, including such items as stretching or therapeutic exercises, which may be used in combination with the support system of the sheet 500. The instructions 536 may be provided by a printed statement, indicia (such as alphabetical or numerical indicia similar to those shown in FIG. 3), a pattern, a photograph, an illustration, or an outline printed separately with, or directly on, the sheet 500 or portion 504. Alternatively, the instructions 536 may be provided on a brochure, print advertisement, card, manual, leaflet, or an electronic media storage device (such as a compact disc, digital video disc, memory stick, etc.) included in the packaging or the instructions 536 may be printed directly on the packaging 522 as shown in FIG. 8. Alternatively, the instructions 536 may be provided by any combination of the above.

Furthermore, the instructions 536 may direct the user to an interactive website 700 or other media where the user may further learn about the support system 504, plantar fasciitis, foot pain, arch pain, heal pain, and treatments and exercises. For example, the website 700 may provide the user with illustrations, descriptions of symptoms, and provide answers to questions to assist the user in confirming the diagnosis of plantar fasciitis. The website 700 may have numbered illustrations of the foot or sections of the foot that the user can select to describe the location of the pain. The website 700 may provide a questionnaire asking about the user's height, weight, age, flexibility, activities and activity level, changes in height or activity level, foot type (high arched, normal arched, flat footed), family history of plantar fasciitis, severity of pain, shoe sizes, shoes types and any number of other topics that will allow the website to advise the user on whether the user has plantar fasciitis and/or other kinds of foot pain or injuries such as a bruised heel, bunion, plantar wart, or any number of other problems. The website 700 helps the user determine whether the user actually has plantar fasciitis and thus whether the user should use the support system 504. People suffering from foot problems other than plantar fasciitis may not benefit from using the support system 504.

The interactive process of the website 700 provides the user with illustrations and instructions to help the user determine whether the user should use the support system 504 and determine the best size and shape of the support system 504 for the user to use. The interactive process may further instruct the user as to how to prepare the foot for application of the support system 504, such as by shaving or removing hair from the foot and removing oils and lotions from the foot. The interactive process may further instruct the user on the temperature at which to use the support system 504 and what tension levels are appropriate for use of the support system 504. The interactive process may further allow the user to chart and report progress in treating plantar fasciitis and answer questions the user may have during the course of the treatment. The interactive process may also provide methods to ease removal of the support system 504.

The website 700 may also educate the user on the causes of stress on the plantar fascia and the factors which may contribute to plantar fasciitis such that the user may be able to change or alter activities that irritate or damage the plantar fascia. For example, the website 700 may inform users who climb stairs for exercise that such a practice may contribute to plantar fasciitis and provide ways to alter the user's behavior so as to reduce inflammation of the plantar fascia.

As part of the interactive process, the website 700 may provide the user with therapeutic exercises or stretches to perform while using the support system 504. Stretches which focus on the plantar fascia may be appropriate in later stages of treatment, and the interactive process may recommend exercises to the user at the appropriate point in the user's recovery that will further benefit the recovery. For example, because a biomechanical relationship exists between the calf muscle, the Achilles tendon, and the plantar fascia, the website may recommend exercises to stretch these areas while the user wears the support system such that the stress on the plantar fascia is controlled during stretching. The website 700 may recommend common calf-stretching exercises that incorporate the use of an angled board, stairs, a block, or a towel while wearing the support system 504. Examples of such exercises are described in American Family Physician, Vol. 63, Number 3, pages 469-470, the subject matter of which is incorporated herein by reference.

The interactive process of the website 700 may also suggest a particular shape or size of the support system 504 for the user based on the user's particular condition, footwear, or activities. By way of example only, the website 700 may recommend a support system 504 having a strapless sole portion 502 for a woman who wishes to wear open toed shoes. By way of example only, the website 700 may recommend a support system 504 having a sole portion 502, heel tabs 510, a ball strap 506 and an additional strap (not shown) for the arch of the foot to an overweight user who places a lot of weight to the arch of the foot. By way of example only, the website 700 may recommend a support system 504 having no straps across the arch of the foot to a runner that wears good arch-supporting running shoes.

In order to gain access to the interactive website 700, the user may be required to log-on with a code that is provided with the support system 504. Medical professionals such as doctors who are not the end users of the support system 504 may be allowed to enter and use the interactive website through separate method of access.

In operation, the user removes a sheet 500 from the packaging 522 of FIG. 8. The user may review the instructions 536 that come with the sheet 500 to learn how to apply and use the support system 504. The user removes or punches or cuts out the support system 504 from the sheet 500.

Figure 10:
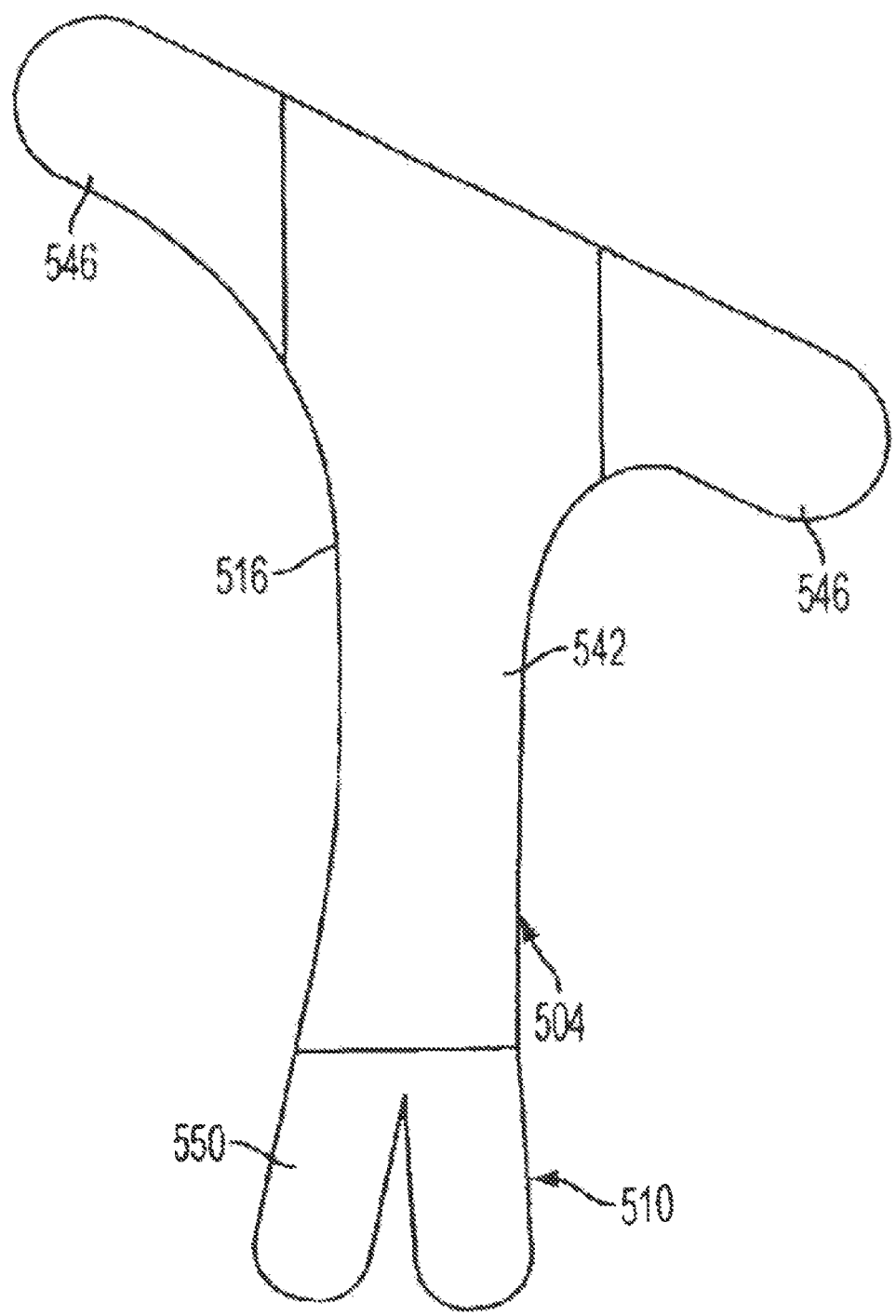
FIG. 10 illustrates a bottom view of a support system in accordance with an embodiment of the present invention.
Figure 11:
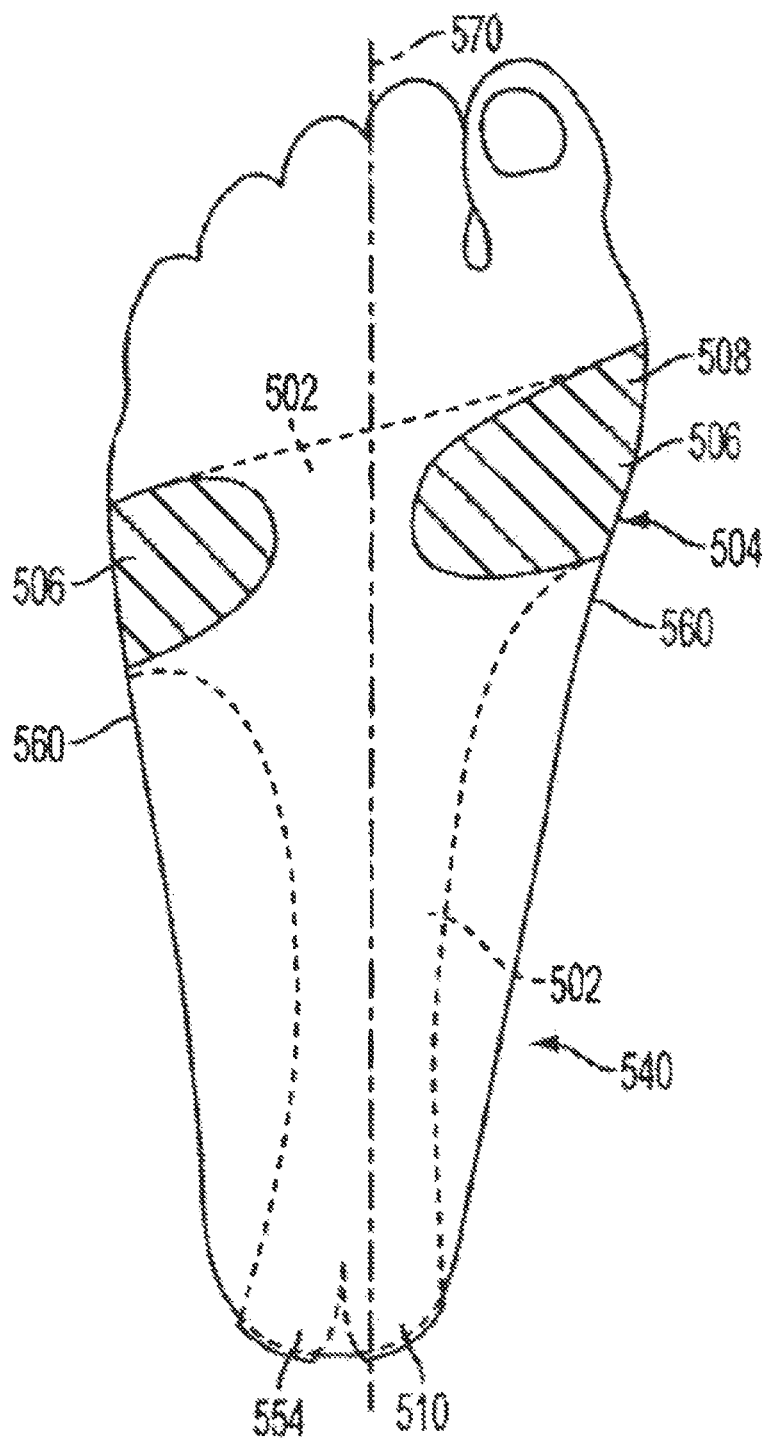
FIG. 11 illustrates a top view of a foot having the support system of FIG. 10 affixed to the foot.
Figure 12:
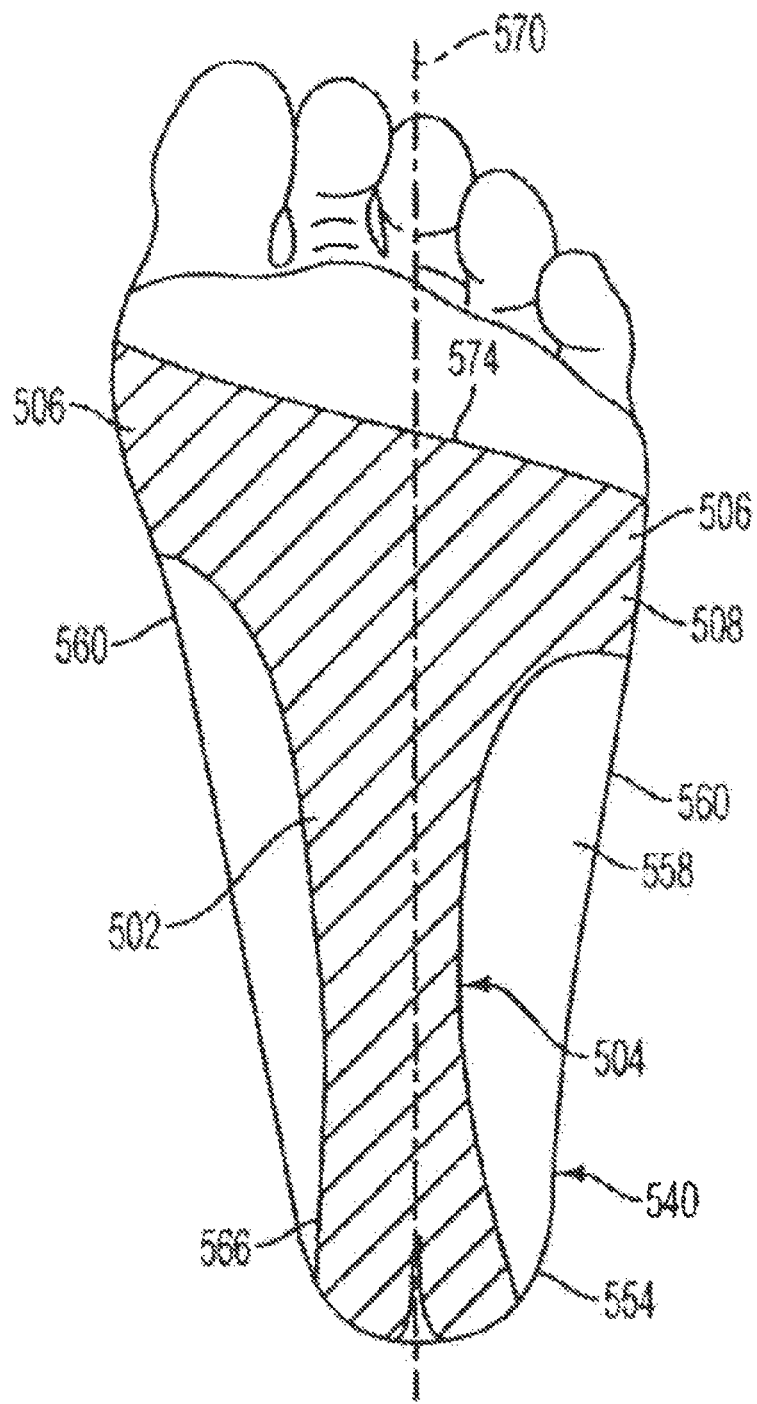
FIG. 12 illustrates a bottom view of the foot and support system of FIG. 11.
Figure 13:
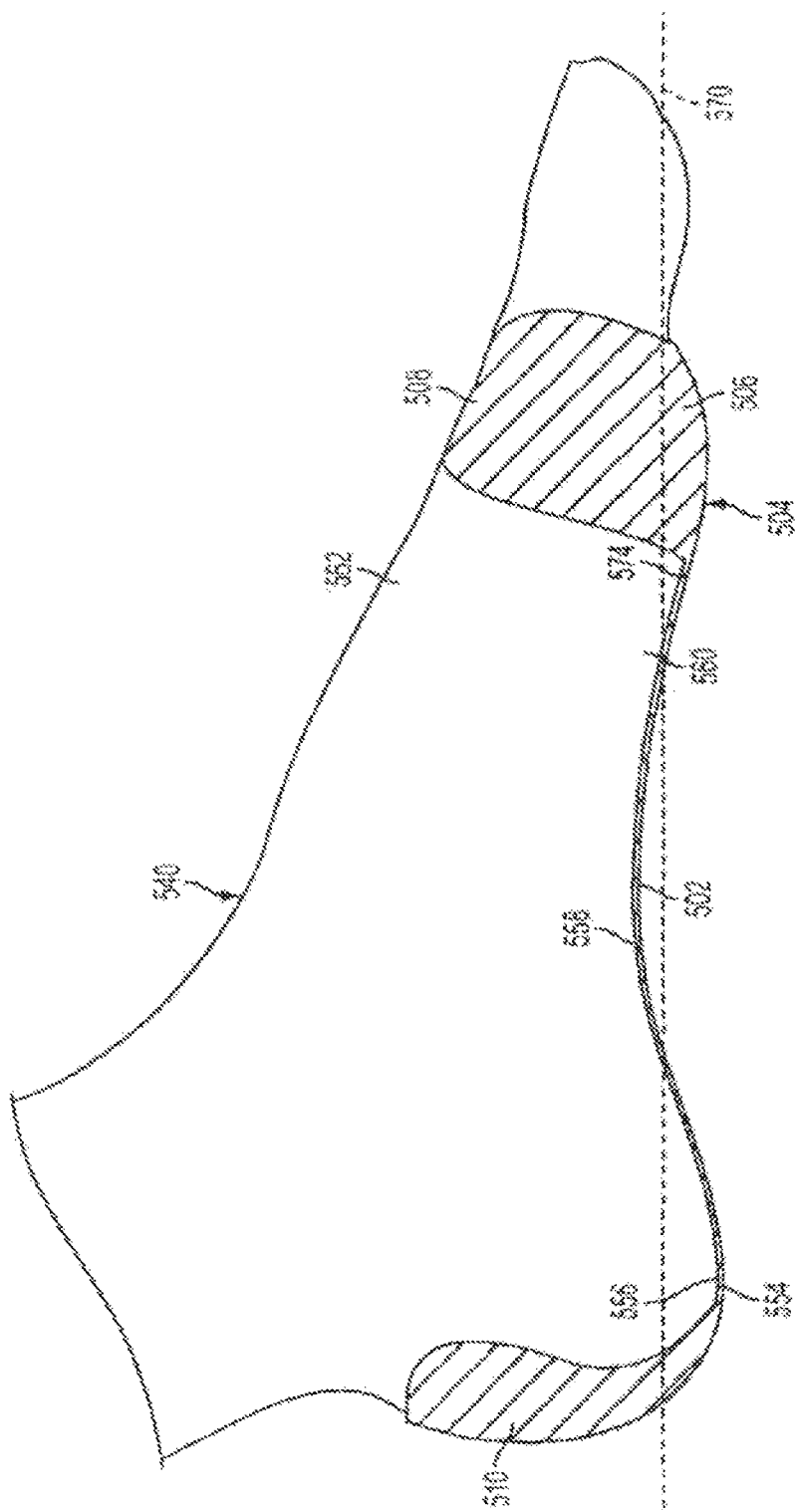
FIG. 13 illustrates a side view of the foot and support system of FIG. 11.
Figure 14:
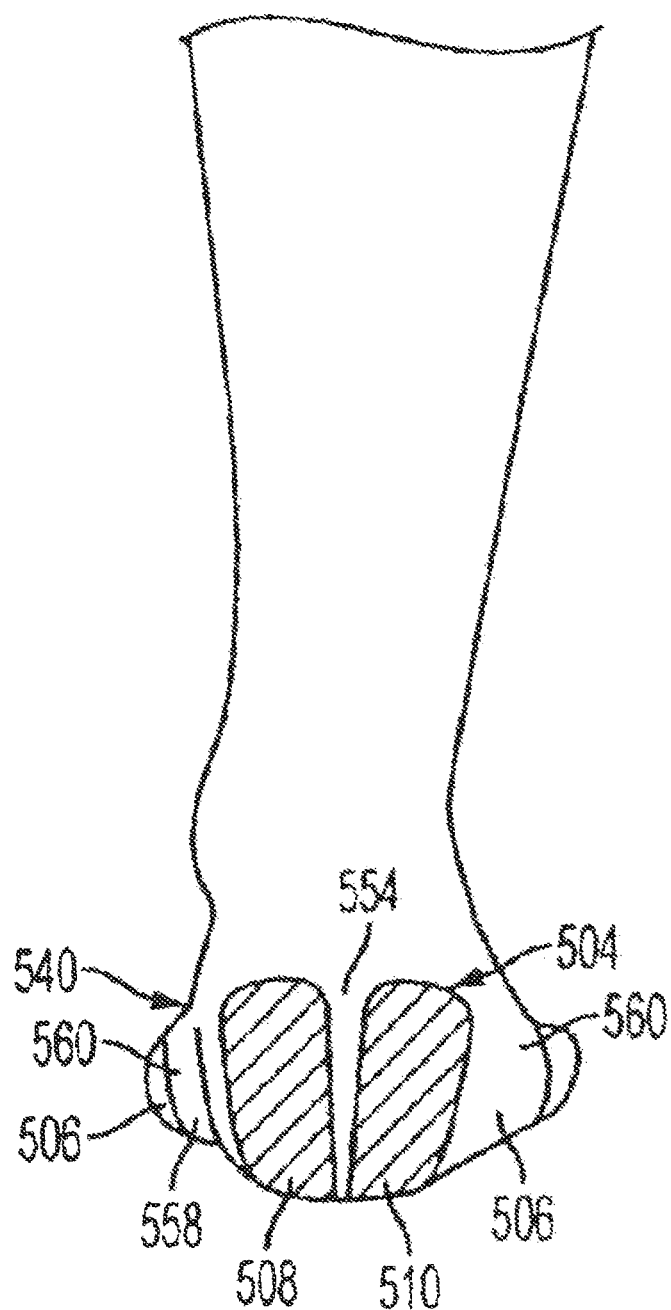
FIG. 14 illustrates a rear view of the foot and support system of FIG. 11.

Referring to FIG. 10, a support system 504 has been removed from the sheet 500. A release liner 516 is separated or perforated into a sole section 542, strap sections 546, and a tab section 550 such that different sections of the release liner 516 may be removed from the support system 504 as necessary. Alternatively, the release liner 516 may have any number of sections as necessary to accommodate the shape and use of the support system 504. After removing the support system 504 from the sheet 500, the user may further cut and form the support system 504 as necessary for application. For example, the user may trim the heel tab 510 such that the heel tab 510 better fits the user's foot.

Referring to FIGS. 11-14, a support system 504 is applied to a foot 540 or a portion of the foot 540. The user peels the tab section 550 (FIG. 10) of the release liner 516 (FIG. 7) from the heel tab 510 of the support system 504 and applies the heel tab 510 of the support layer 508 to the heel 554 of the user's foot 540 such that the adhesive layer 512 (FIG. 7) is affixed to the skin of the user's heel 554 and retains the support layer 508 to the heel 554. The user then peels the sole section 542 of the release liner 516 from the sole portion 502 of the support system 504 and adhesively applies the sole section 542 of the support layer 508 to the sole 558 of the user's foot 540. The sole portion 502 should be positioned about the sole 558 of the foot 540 from the bottom 566 of the heel 554 along a longitudinal axis 570 axis of the foot 540 to the ball 574 of the foot 540. The user then peels the strap sections 546 of the release liner 516 from the ball strap 506 of the support system 504 and adhesively applies the ball strap 506 of the support layer 508 transversely to the longitudinal axis 570 of the foot 540 across the sole 558 of the foot 540 about the sides 560 and top 562 of the user's foot 540 to secure the sole portion 502 about the sole 558. Thus, the multiple sections of the release liner 516 allow the user to use the heel tab 510 as an anchoring connection to the foot 540 such that the sole section 542 and the ball strap 506 may be more easily aligned and affixed to the foot 540 than if the entire support layer 508 was applied to the foot 540 at once. The user may remove and re-apply or adjust the support layer 508 on the foot 540 to obtain a better placement. Once the support layer 508 has been secured to the foot 540 as shown in FIGS. 11-14, the support layer 508 may be worn all day long and changed on a daily basis. The support system 504 may be used continuously or on a periodic basis as needed. Once each support layer 508 has been used, the user removes and disposes of the support layer 508 and reapplies a new support layer 508. The support layer 508 may be used with orthotic practices, physical therapy, and other treatment modalities to treat plantar fasciitis and other foot pain.

Figure 15:
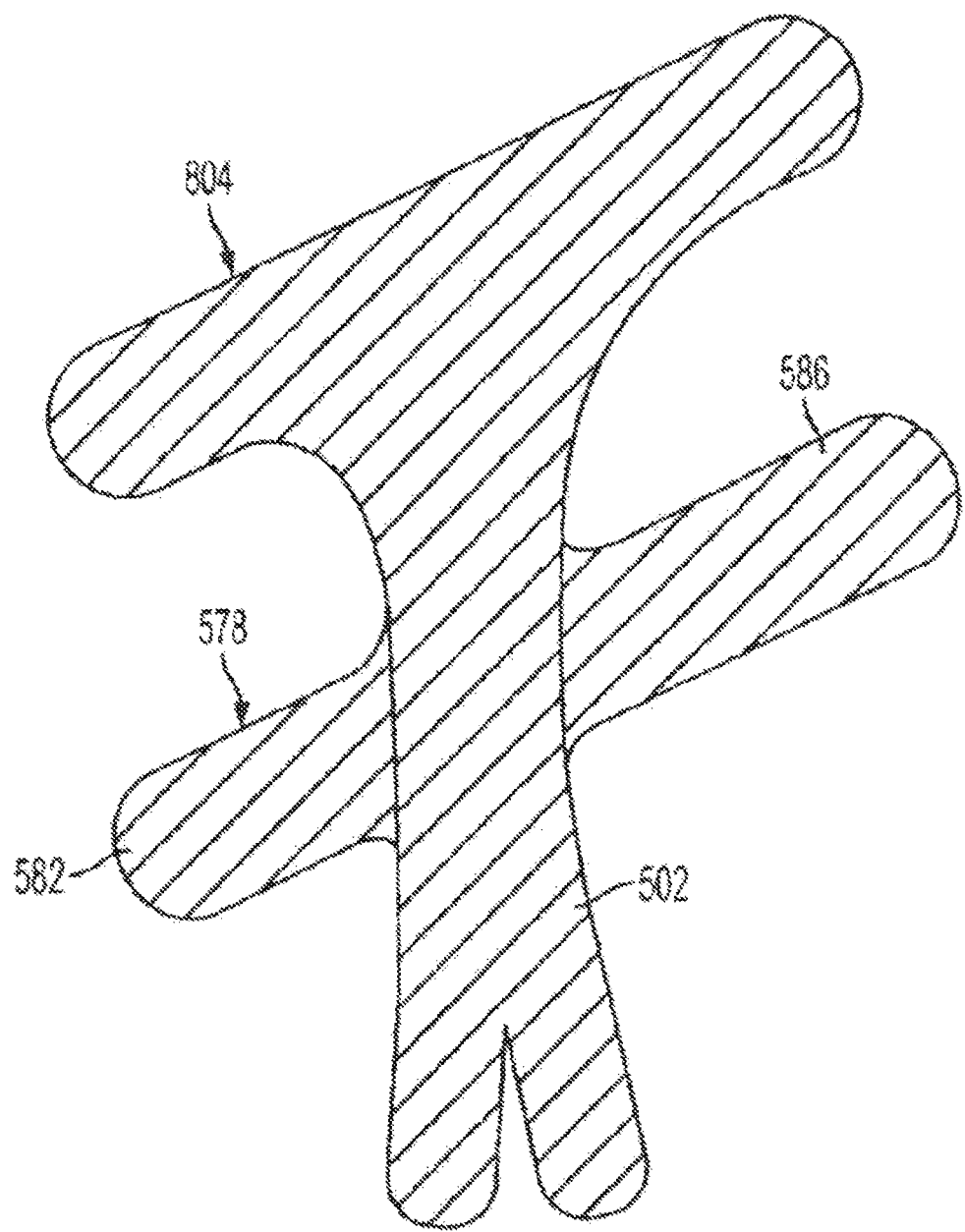
FIG. 15 illustrates a bottom view of a support system in accordance with an embodiment of the present invention.
Figure 16:
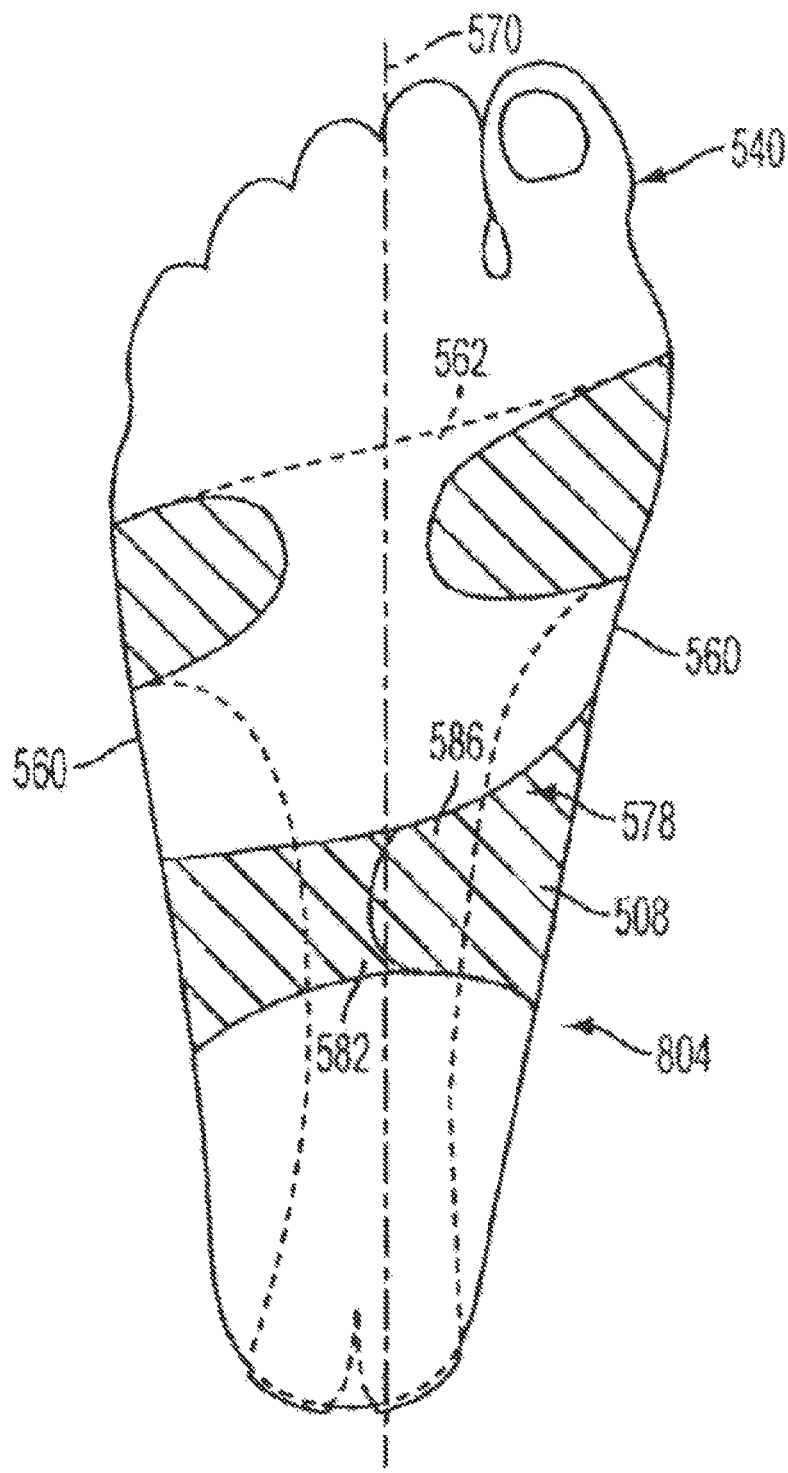
FIG. 16 illustrates a top view of a foot and the support system of FIG. 15 affixed to the foot.
Figure 17:
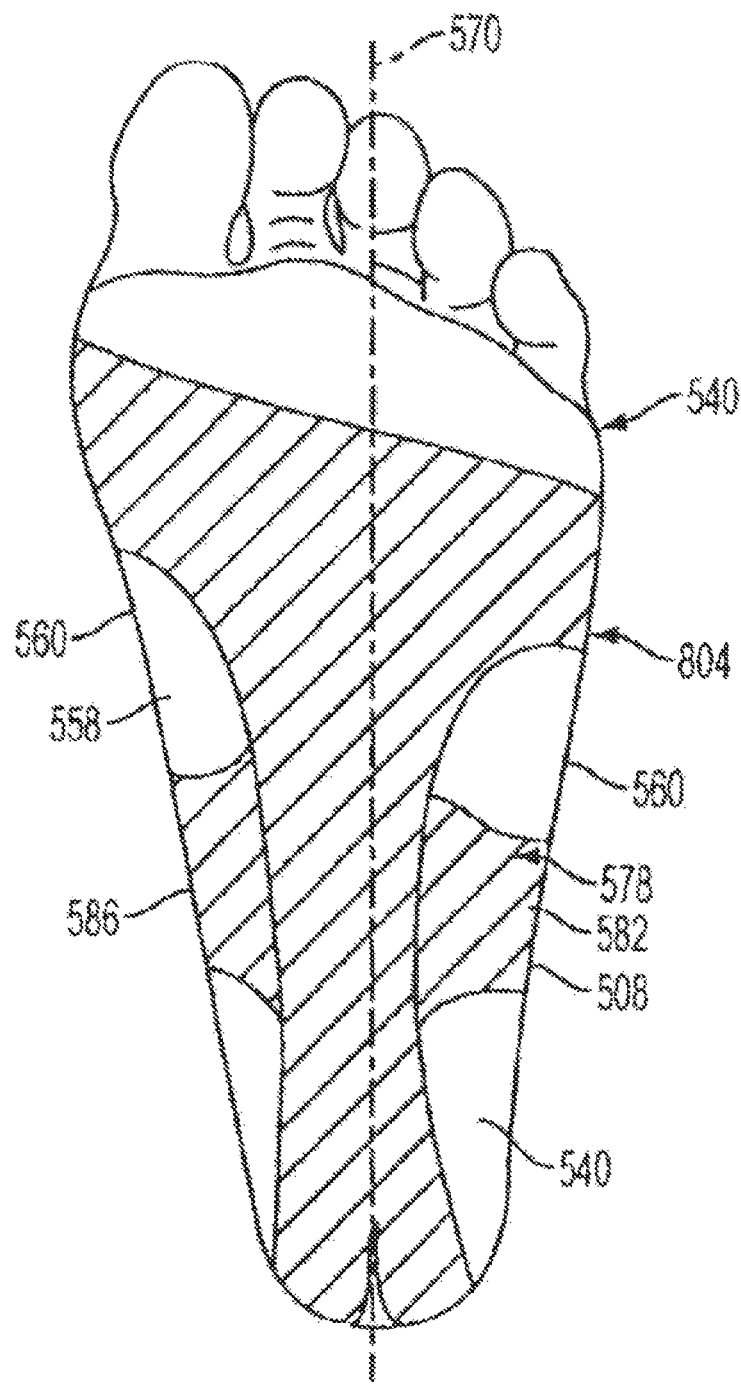
FIG. 17 illustrates a bottom view of the foot and support system of FIG. 15.
Figure 18:
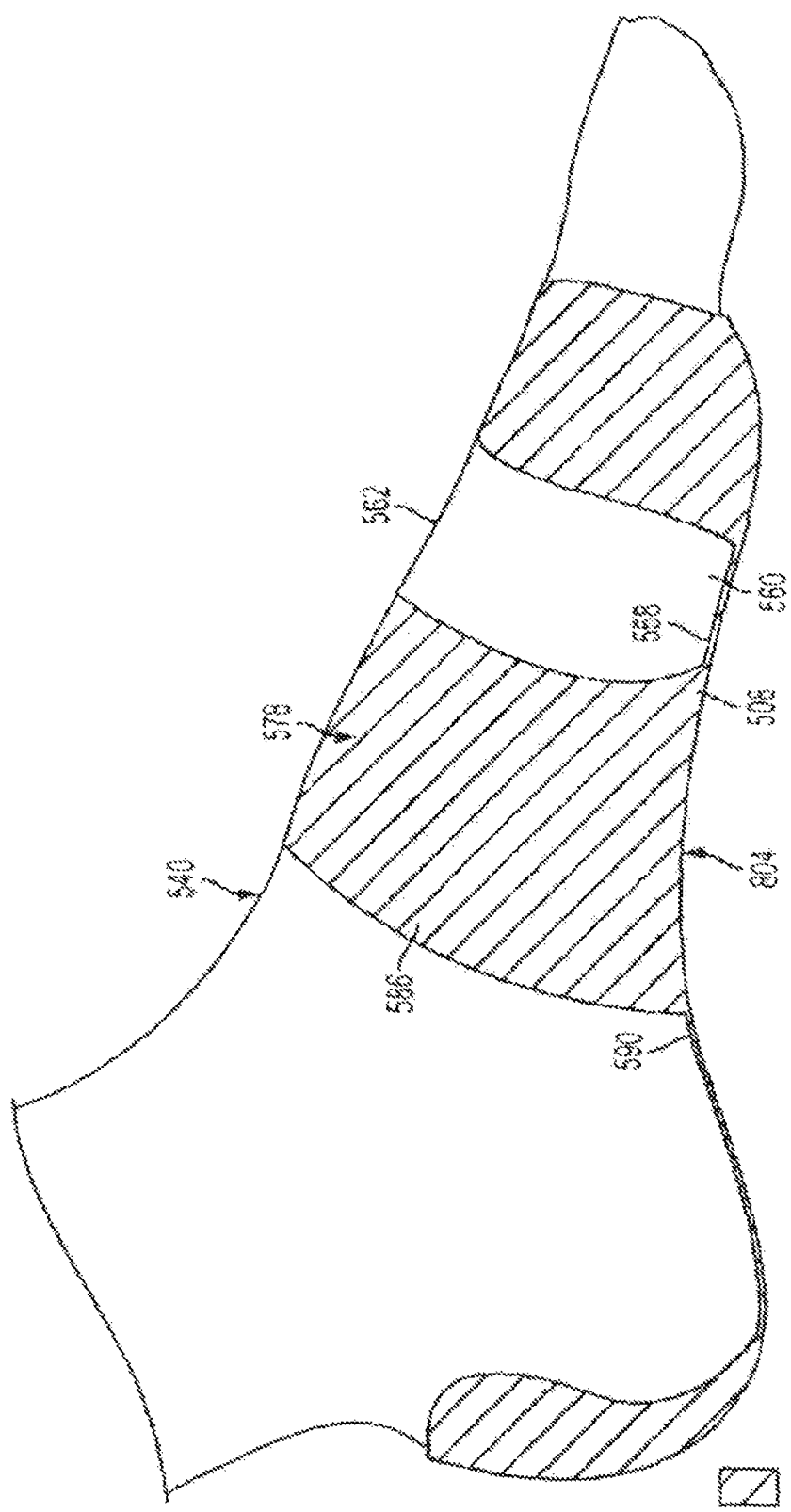
FIG. 18 illustrates a side view of the foot and support system of FIG. 15.

Alternatively, the support system may have any number of different configurations for use with a foot. Referring to FIG. 15, a support system 804 includes an additional arch strap 578 having first and second ends 582 and 586 extending transversely from the sole portion 502. FIGS. 16-18 illustrate multiple views of the support system 804 of FIG. 15 applied to a foot 540. The support system 804 is applied to the foot 540 in generally the same manner as the support system of FIGS. 11-14. However, the user also adhesively applies the arch strap 578 of the support layer 508 transversely to the longitudinal axis 570 and arch 590 of the foot 540 across the sole 558 of the foot 540 and about the sides 560 and top 562 of the user's foot 540 such that the first and second ends 582 and 586 may or may not overlap and are adhesively connected at the top 562 of the user's foot 540. The embodiment of the support system 804 with the arch strap 578 provides additional support along the arch 590 of the foot 540.

Figure 19:
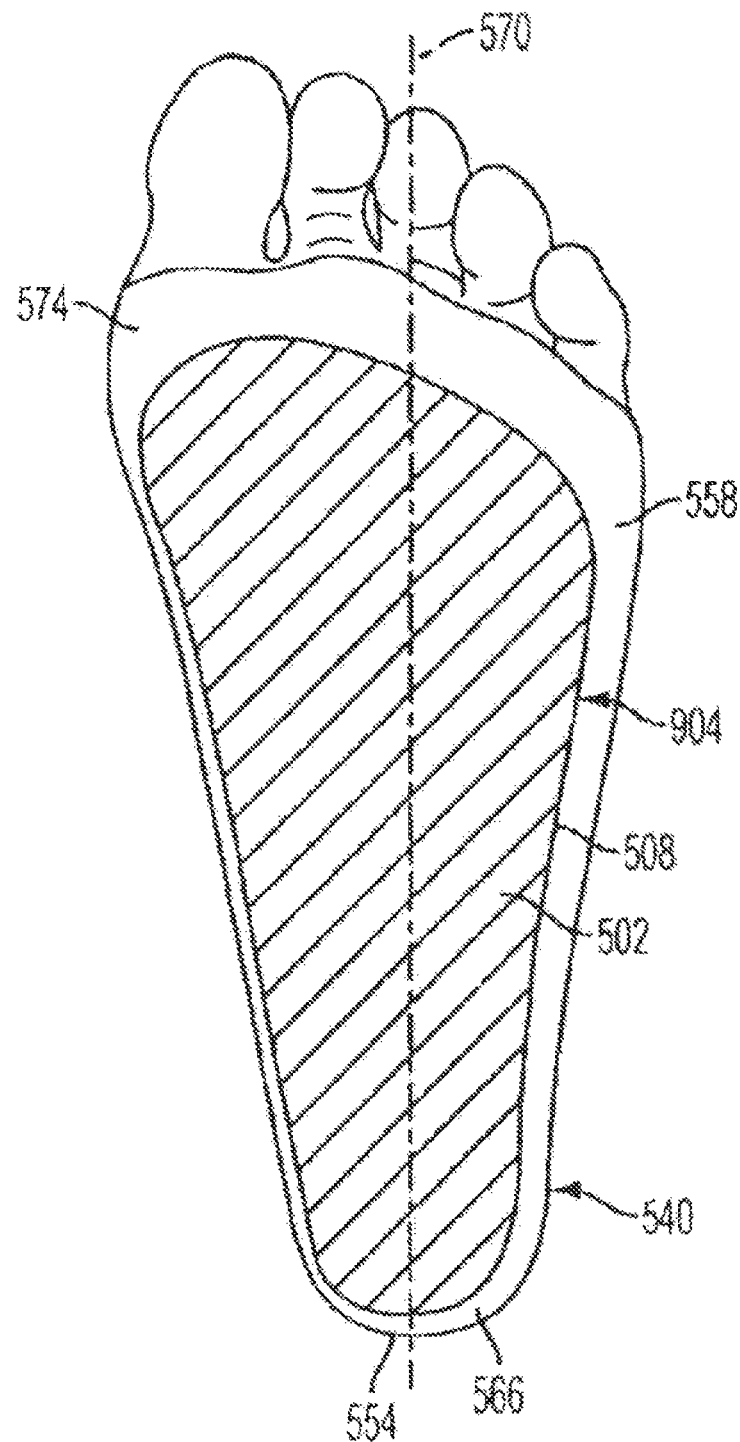
FIG. 19 illustrates a bottom view of a foot and a support system in accordance with an embodiment of the present invention.

Referring to FIG. 19, a support system 904 may include a strapless sole portion 502 that is adhesively applied to the entire sole 558 of the foot 540 from the bottom 566 of the heel 554 along the longitudinal axis 570 axis of the foot 540 to the ball 574 of the foot 540. Alternatively, the sole portion 502 may only cover a portion of the sole 558. Because the support system 904 does not include any straps, users may discretely wear the support system 904 with shoes that reveal the top and sides of the user's foot, such as sandals or other open shoes.

Figure 20:
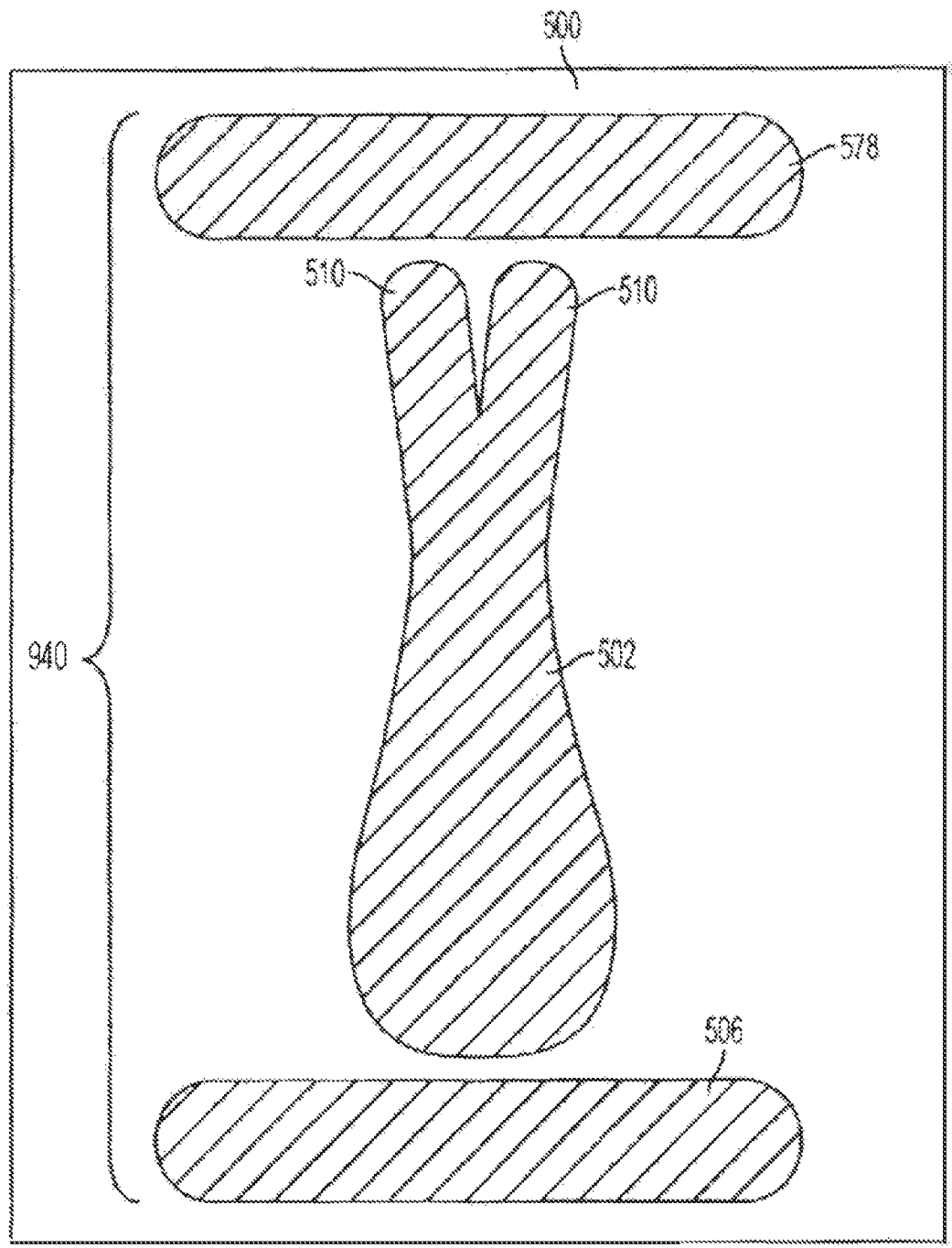
FIG. 20 illustrates a top view of a sheet of material containing a support system in accordance with an embodiment of the present invention.

Alternatively, as shown in FIG. 20, the support system 940 may include separate portions that can be removed from the sheet 500. The support system 940 includes the sole portion 502 with heel tabs 510, the ball strap 506, and the arch strap 578, each of which can be removed separately from the sheet 500 for application to the foot 540. For example, the user may apply the sole portion 502 first, and then apply either or both of the ball strap 506 and the arch strap 578 as the user sees fit. Alternatively, the user may only apply one of the sole portion 502, the ball strap 506 or the arch strap 578, or any combination thereof. Thus, the embodiment of FIG. 20 offers the user more flexibility in tailoring the treatment to the user's specific needs for treating pain while limiting the visibility of the support system 940.

Figure 21:
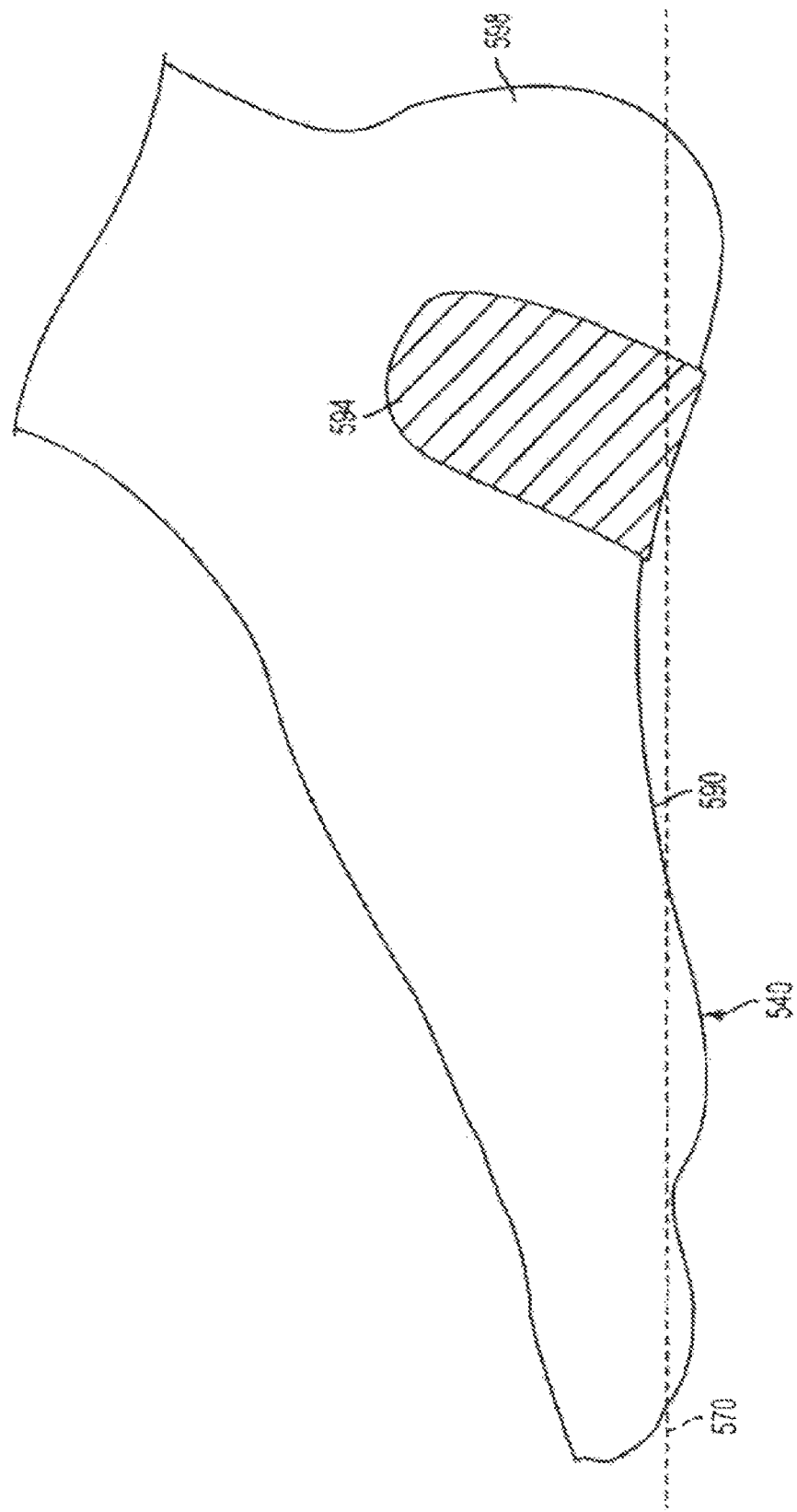
FIG. 21 illustrates a left side view of a foot and a strap affixed to the foot in accordance with an embodiment of the present invention.
Figure 22:
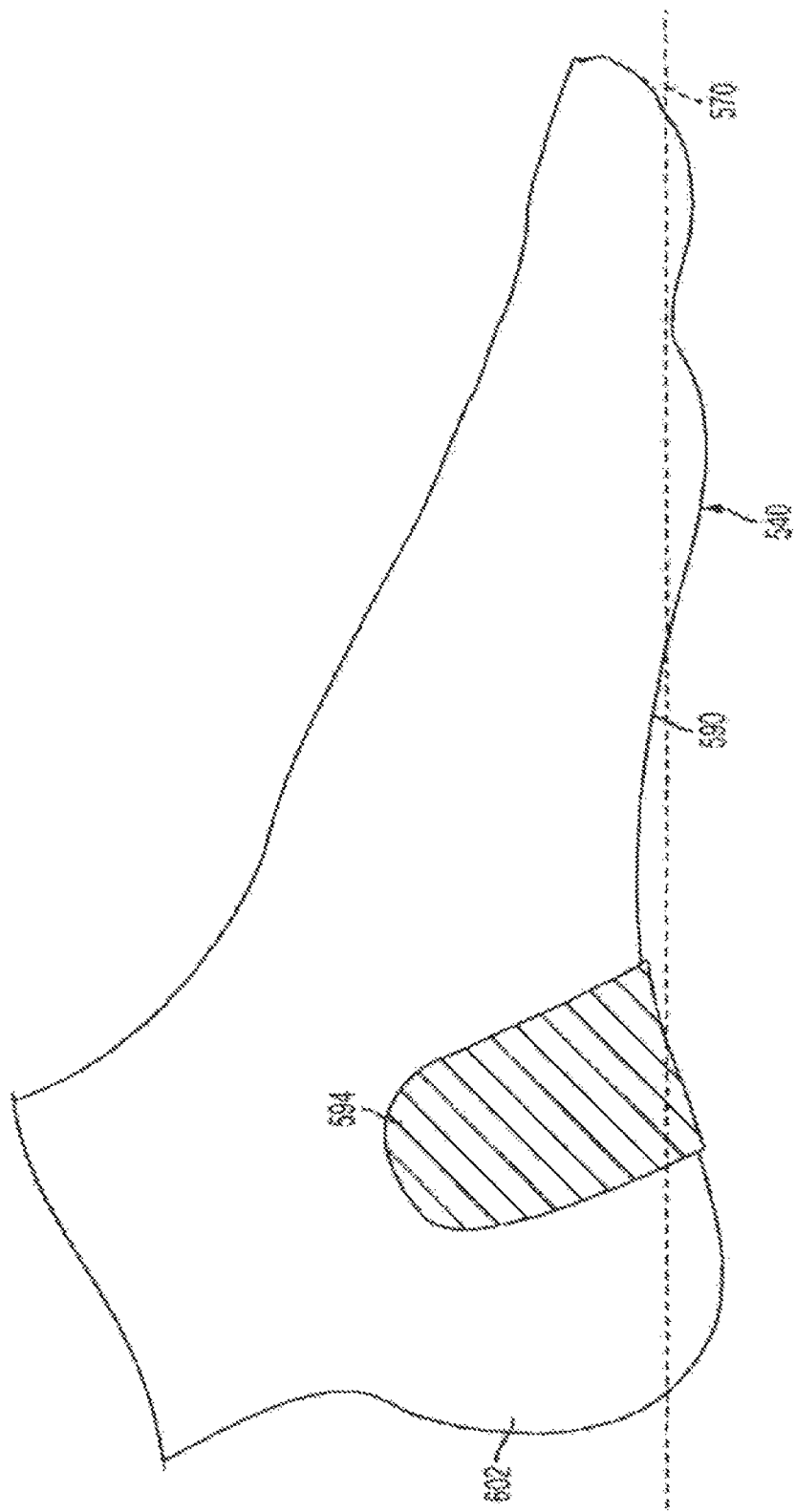
FIG. 22 illustrates a right side view of the foot and strap of FIG. 21.
Figure 23:
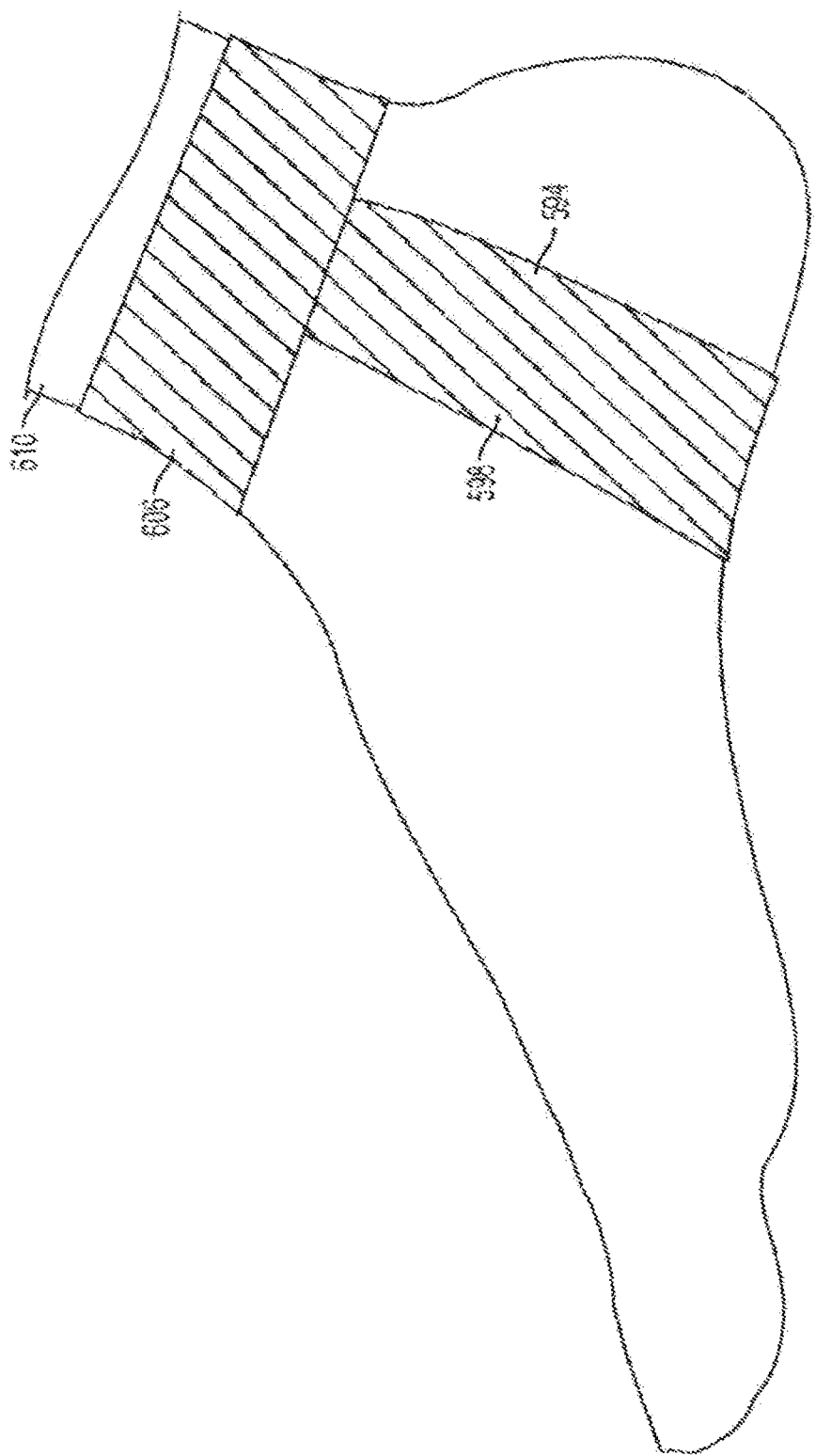
FIG. 23 illustrates a side view of a foot and a strap affixed to the foot in accordance with an embodiment of the present invention.

Alternatively, the support system may include a single strap that the user can use in combination with orthotic practices to address specific pain problems. The strap may be sized and shaped to address the particular areas of the user's foot that need treatment. FIGS. 21 and 22 illustrate opposite side views of a strap 594 applied to a foot 540. The single strap 594 may be applied to the foot 540 transversely to the arch 590 and longitudinal axis 570 of the foot 540 from ankle 598 to ankle 602. The strap 594 provides constant pressure along the arch 590 of the foot 540 to reduce inflammation and thus reduces pain. The strap 594 may be worn at night when the user sleeps. Alternatively, as shown in FIG. 23, the strap 594 may include a support strap 606 configured to hold the strap 594 about the ankles 598 and 602. By way of example only, the support strap 606 may be retained about the leg 610 by adhesive, elastic, or Velcro.

Figure 24:
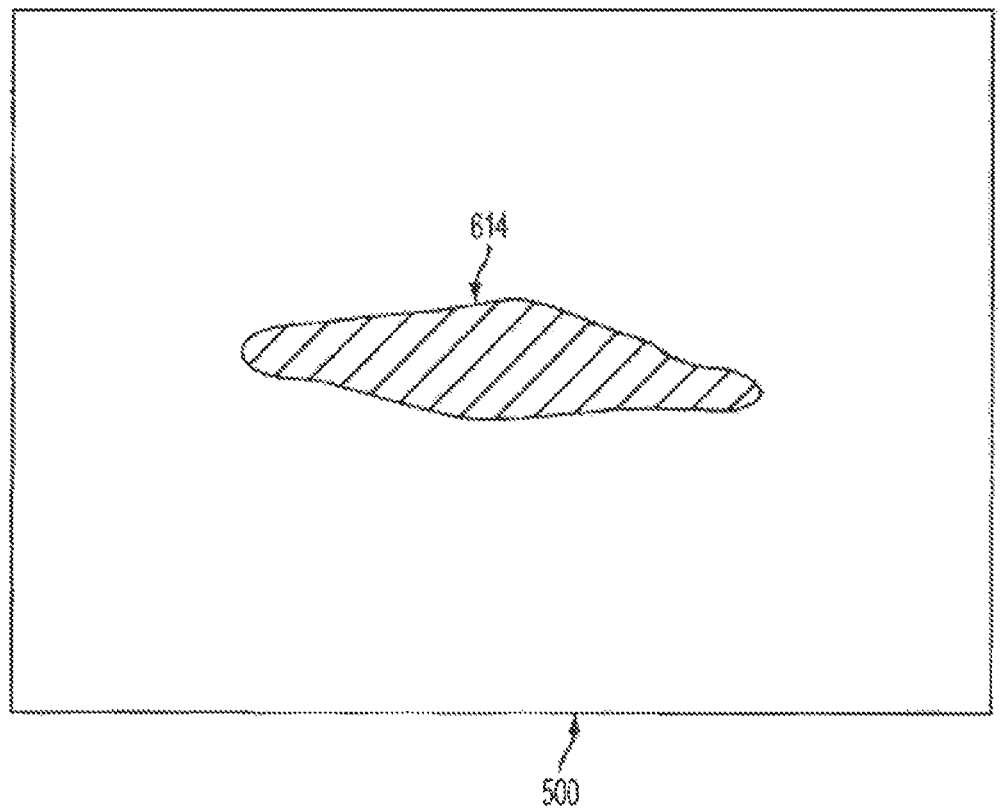
FIG. 24 illustrates a top view of a sheet of material containing a support system in accordance with an embodiment of the present invention.
Figure 25:
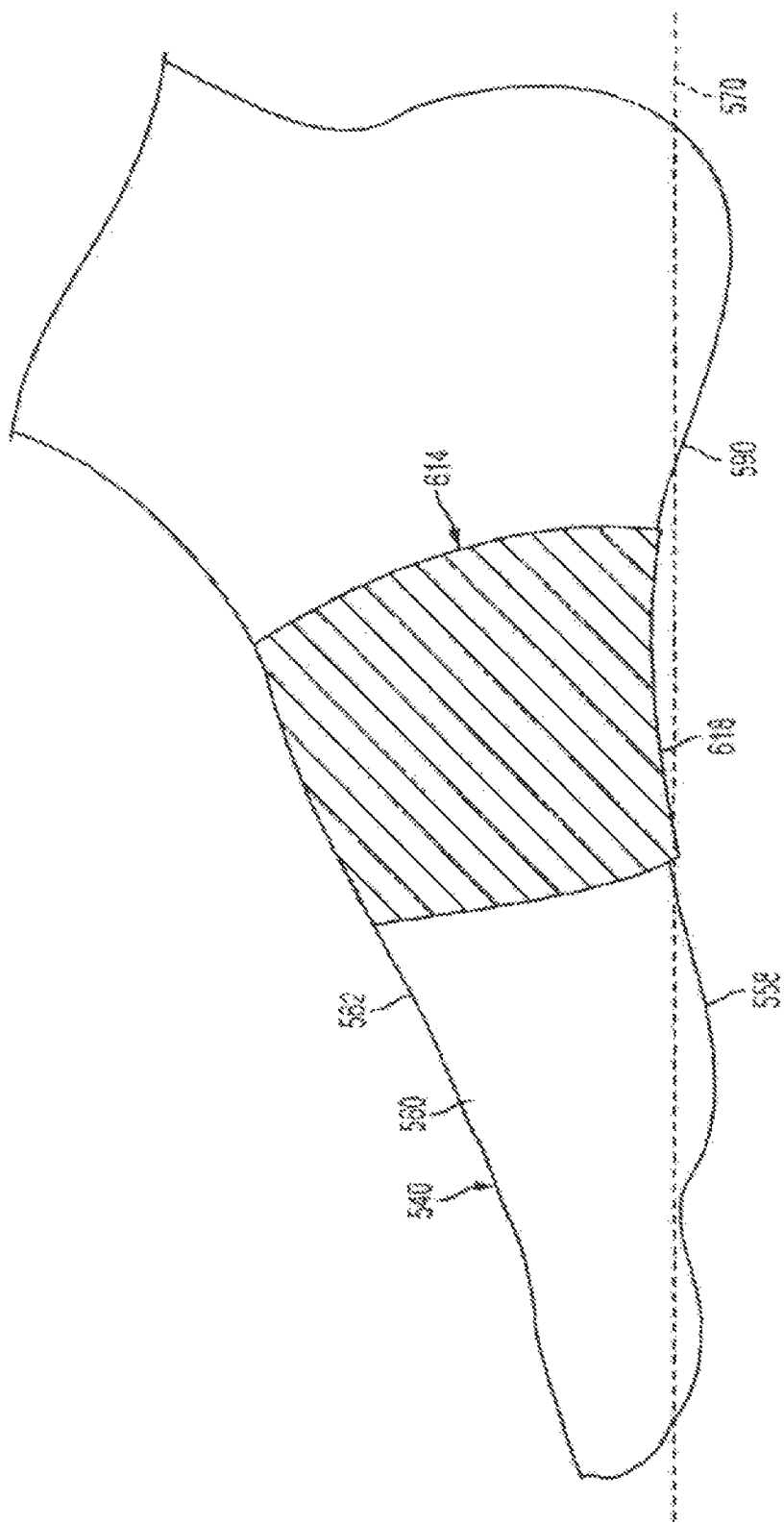
FIG. 25 illustrates a side view of a foot and the support system of FIG. 24.

FIG. 24 illustrates a top view of a diamond-shaped strap 614 that may be provided on a sheet 500 as part of a support system according to an embodiment of the present invention. As shown in FIG. 25, the strap 614 may be applied to the foot 540 transversely to the longitudinal axis 570 and arch 590 of the foot 540 across the sole 558 of the foot 540 and about the sides 560 and top 562 of the user's foot 540 like the arch strap 578 of FIG. 15. The strap 614 anatomically supports the medial arch of the foot 540 instead of specifically to the longitudinal arch.

Figure 26:
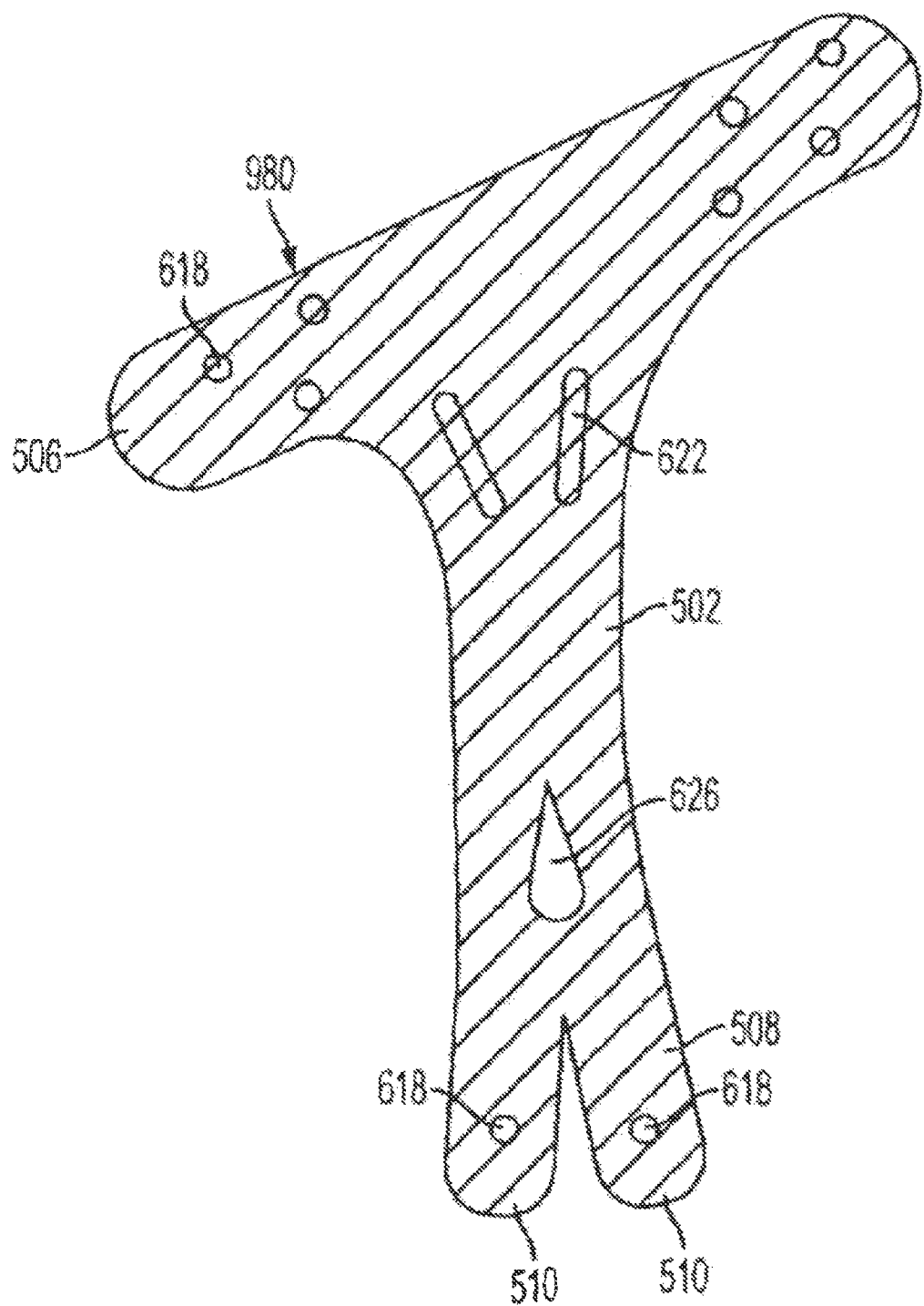
FIG. 26 illustrates a top view of a support system in accordance with an embodiment of the present invention.

FIG. 26 illustrates a top view of the support system 980 in accordance with an embodiment of the present invention. The support system 504 includes holes 618 along the ball strap 506 and heel tabs 510 and slots 622 and a tear-shaped aperture 626 along the sole portion 502. Alternatively, the support system 980 may include any number of apertures having other shapes. Alternatively, the support system 504 may have at least one of, or any combination of, the holes 618, slots 622 and aperture 626 at any other locations thereon. The holes 618, slots 622, and aperture 626 are provided to alter the stretch resistant properties of the support system 980, focus or transfer the stress carried by the support system 980, or aid in preventing direct application of pressure to inflamed areas of the foot when the support layer 508 of the support system 980 is applied to the user's foot. Also, the holes 618, slots 622, and aperture 626 allow the skin from the foot to breathe and allow the skin to contact surfaces in order to reduce the possibility of the user slipping while wearing the support system 980. Additionally, the holes 618, slots 622, and aperture 6226, may be ornamental. The holes 618, slots 622, and aperture 626 may be pre-cut into the support system 980 or may be created by the user.

Like the support system 400 of FIG. 3, the foot support kit serves to restrict extension of the tissue on the bottom of the foot and thus the level of tensile stress on the plantar fascia to reduce foot pain, arch pain, and heel pain, and to rehabilitate the plantar fascia, and to prevent injury to the plantar fascia. The stretch resistant properties of the support layer 508 share the stresses normally absorbed by the plantar fascia alone. The support layer 508 manages foot pain and addresses the cause of plantar fasciitis by controlling and limiting the stress on the plantar fascia and surrounding tissues across both the medial and longitudinal arches and thus minimizes tears in the plantar fascia.

The stretch resistant plantar fascia support system of the different embodiments may be used while sleeping, while walking around with barefeet, or while wearing various types of footwear. Also, the stretch resistant plantar fascia support system non-invasively reduces the level of tensile stress carried by the plantar fascia and may prevent the need for complex and expensive surgery.

For example, a consumer may wake-up in the morning and experience pain along the bottom of the consumer's foot. The consumer may recognize the pain as plantar fasciitis and desire to treat the pain. Rather than schedule an appointment with a doctor and have to travel to the doctor's office for treatment, during which time the plantar fascia may be subjected to further excessive tensile stress, the consumer may desire to treat the pain at home.

With the stretch resistant plantar fascia support system of the present invention, the consumer may save the time, expense, and pain of traveling to a doctor's office for treatment. To use the stretch resistant plantar fascia support system, the consumer would simply remove the removable protective covers that protect the adhesive layer and apply the stretch resistant plantar fascia support system to the affected area.

While the above scenario described the consumer applying the stretch resistant plantar fascia support after waking up in the morning, the stretch resistant plantar fascia support system may also be worn to bed at night. By wearing the stretch resistant plantar fascia support system to bed at night, the stretch resistant plantar fascia support system may aid in the healing process while the consumer sleeps and protects the plantar fascia during the first few steps in the morning when stress is re-applied.

In addition, the stretch resistant plantar fascia support system may be comfortably worn when the consumer is not currently experiencing pain, but anticipates the potential for injury during a strenuous activity. For example, a consumer with a history of frequent occurrences of plantar fasciitis may desire to return to a strict exercise regiment following a prolonged period of inactivity. To avoid overstressing the plantar fascia until the foot has had enough time to become re-accustomed to the stresses of exercise, the consumer may desire to use the easily applied stretch resistant plantar fascia support system rather than some of the more cumbersome, less effective, and inconvenient alternatives such as taping and molded arch supports.

To aid the consumer with installation of the stretch resistant plantar fascia support system, the removable protective covers, or other portions of the stretch resistant plantar fascia support system, may include numerical indicia that indicate the order in which portions of the stretch resistant plantar fascia support system are applied to the foot. The consumer then applies the stretch resistant plantar fascia support system to the consumer's foot in the prescribed order.

In addition, the stretch resistant plantar fascia support system is comfortable and form fitting. The stretch resistant plantar fascia support system may be supplied for a plurality of foot sizes and the consumer may select the stretch resistant plantar fascia support system much like shoes are selected based upon standard shoe sizes. The foot sole support of the stretch resistant plantar fascia support system may even be shaped to conform to the shape of the sole of a foot. If an adjustment is needed to adapt the stretch resistant plantar fascia support system to an irregularity in a particular consumer's foot, the stretch resistant plantar fascia support system may be easily adapted by cutting the stretch resistant plantar fascia support system to accommodate the irregularity.

Because the stretch resistant plantar fascia support system is form fitting, the consumer may wear the stretch resistant plantar fascia support system in a variety of situations. For example, if a woven rayon microfiber with a 3600 thread count and/or thickness less than 30 mils, or alternatively less than 15 mils, is used, then the stretch resistant plantar fascia support system is thin enough to comply with contours of the foot and strong enough to provide adequate strength. While the consumer has the stretch resistant plantar fascia support system attached to the consumer's foot, the consumer has the option of walking around in bare feet, pulling a sock over the foot, or putting on shoes. The consumer may also wear the stretch resistant plantar fascia support system while using other additional devices such as arch supports, night splints, and custom orthotics.

Also, the stretch resistant plantar fascia support system does not interfere with rotation and movement of the ankle or calves. The stretch resistant plantar fascia support system is positioned beneath the ankle. The heel straps and the heel strap tabs are sized to avoid interference with the ankle bone. Because the stretch resistant plantar fascia support system is positioned beneath the ankle, contact between adhesive and leg hair is reduced. Thus, the need for shaving portions of the leg and ankle is reduced.

Also, different embodiments of the stretch resistant plantar fascia support system may be used depending on the type of footwear the consumer desires to wear while the stretch resistant plantar fascia support system is attached. For example, if the consumer is going to wear sandals, the consumer may desire to use a stretch resistant plantar fascia support system with a foot sole support and no adhesive straps or tabs to reduce the visibility of the stretch resistant plantar fascia support system. On the other hand, the consumer may desire to wear boots, where visibility of the stretch resistant plantar fascia support system is not an issue, and the consumer desires to have straps and tabs along with the foot sole portion for added stability.

The present invention may also include other items that can benefit a user. For example, to minimize the potential for skin damage and foot odor from the presence of moisture, the stretch resistant plantar fascia support system may be made of a permeable material. The stretch resistant plantar fascia support system may be made of a permeable material that wicks moisture away from the skin or the stretch resistant plantar fascia support system may include holes in the material to allow for the evaporation of moisture. In conjunction with the permeable material, adhesive may be applied in an intermittent manner to further increase the permeability and reduce the presence of moisture trapped between the foot and the stretch resistant plantar fascia support system. Also, the stretch resistant plantar fascia support system may include additives such as medicines, anti-fungal treatments, anti-microbial treatments, anti-inflammatory treatments, cooling compounds, heating compounds, deodorants, zeolite, perfumes, moisturizers, tee tree oil, talcum powder, and zinc oxide.

Thus, the present invention provides an effective system for the treatment of plantar fasciitis that is both economical and easy to use. The present invention provides a stretch resistant system that may be discretely attached to a patient's foot and reduces stress on the plantar fascia.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system of elongate strap supports to provide anatomical support, to reduce pain, or to provide therapeutic treatment, the system comprising:
a first elongate strap support, including:
a support layer of woven fabric, wherein:
the woven fabric is shaped to form an elongate strap with straight sides and with rounded portions;
the woven fabric is substantially resistant to stretching in only one test direction of two test directions specified in ASTM (American Society for Testing and Materials) D3759; and
the woven fabric has a thickness that is less than 30 mils and a tensile strength that is greater than 10 lb/in-width;
an adhesive layer on the support layer for adhesive attachment of the support layer to an outer skin surface of a body; and
a removable cover layer on the adhesive layer;
at least one additional elongate strap support; and
a package containing the first elongate strap support and the at least one additional elongate strap support.

2. The system of claim 1, wherein the woven fabric has a ratio of elongation in percent to tensile strength (lb/in-width) that is less than 0.9 in the only one test direction, wherein elongation and tensile strength are determined in accordance with ASTM D3759.

3. The system of claim 1, wherein the woven fabric includes a combination of natural and synthetic fibers.

4. The system of claim 1, wherein the woven fabric includes Rayon.

5. The system of claim 1, wherein the woven fabric consists essentially of of synthetic fibers.

6. The system of claim 1, wherein the adhesive layer has a holding strength of greater than 15 oz/in.

7. The system of claim 1, wherein the first elongate strap support exhibits less than 15% elongation when subjected to a 25 lb tensile load in the only one test direction.

8. The system of claim 1, wherein the woven fabric of the first elongate strap support has a tensile strength of greater than 20 lb/in-width.

9. The system of claim 1, wherein the first elongate strap support further comprises an anti-microbial.

10. The system of claim 1, wherein the first elongate strap support is configured for use in conjunction with at least one additional elongate strap support such that when applied to the body the first elongate strap support and the at least one additional strap support intersect.

11. The system of claim 1, wherein the first elongate strap support further comprises a heating compound.

12. The system of claim 1, wherein the woven fabric is a microfiber fabric.

13. The system of claim 1, wherein at least one of the elongate strap supports is an arch strap configured for ease of application to a foot generally transversely to a longitudinal axis of the foot in an arch area and to extend from a first side of a foot to a second side of a foot.

14. The system of claim 13, wherein the arch strap is configured to be applied to the foot in conjunction along with at least one additional elongate strap support, such that the arch strap and the additional elongate strap intersect when applied to the foot.

15. The system of claim 1, wherein the first elongate strap support and one of the at least one additional elongate strap support are configured to be applied to the body in combination.

16. The system of claim 15, wherein the first elongate strap support and said one of the at least one additional elongate strap support are configured to intersect when applied to the body.

17. The system of claim 1, wherein the adhesive layer is intermittent across the support layer, such that permeability is enhanced.

18. The system of claim 1, wherein the first elongate strap support and at least one additional elongate strap support are of different sizes.

19. A system of elongate strap supports to provide anatomical support, to reduce pain, or to provide therapeutic treatment, the system comprising:
   a first elongate strap support, including:
      a woven fabric support layer including at least fibers other than only natural fibers, wherein:
         the woven fabric support layer is shaped to form an elongate strap that is pre-cut to include rounded portions;
         the woven fabric support layer is substantially resistant to stretching in at least a first test direction specified in ASTM (American Society for Testing and Materials) D3759; and
         the woven fabric support layer has a tensile strength of greater than 10 lb/in-width in the at least one direction and a thickness less than 30 mils;
      an adhesive layer on the woven fabric support layer for adhesive attachment of the woven fabric support layer to an outer skin surface of a body; and
      a removable cover layer on the adhesive layer;
   at least one additional elongate strap support; and
   a package containing the first elongate strap support and the at least one additional elongate strap support.

20. The system of claim 19, wherein the woven fabric support layer is less stretch-resistant in a second test direction specified in ASTM D3759 than in the first test direction.

21. The system of claim 19, wherein:
   the woven fabric support layer has a ratio of elongation in percent to tensile strength (lb/in-width) that is less than 0.9 in the first test direction and a ratio of elongation in percent to tensile strength (lb/in-width) is greater than 0.9 in a second test direction specified in ASTM D3759, wherein elongation and tensile strength are determined in accordance with ASTM D3759.

22. The system of claim 19, wherein the woven fabric support layer includes a combination of natural and synthetic fibers.

23. The system of claim 19, wherein the woven fabric support layer includes Rayon.

24. The system of claim 19, wherein the woven fabric support layer is a microfiber fabric.

25. The system of claim 19, wherein the first elongate strap support exhibits less than 15% elongation when subjected to a 25 lb tensile load in the first test direction.

26. The system of claim 19, wherein the woven fabric support layer is substantially stretch-resistant in a second test direction specified in ASTM D3759.

27. The system of claim 19, wherein at least one of the elongate strap supports is an arch support strap configured for ease of application to a sole of a foot across the longitudinal axis of the foot in an arch area from a first side of a foot to a second side of a foot.

28. The system of claim 27, wherein the arch support strap has a length sufficient to extend across a sole of a foot, from a top or side of a foot on one side of the foot, to the opposite side of the foot, and wherein the arch support strap is configured to be applied to the foot, in conjunction with at least one additional elongate strap support, such that the arch strap and the additional elongate strap intersect when applied to the foot.

29. The system of claim 19, wherein the first elongate strap support and one of the at least one additional elongate strap support are configured to be applied to the body in combination.

30. The system of claim 29, wherein the first elongate strap support and said one of the at least one additional elongate strap support are configured to intersect when applied to the body.

31. The system of claim 19, wherein the adhesive layer is intermittent across the support layer, such that permeability of the first elongate strap support is enhanced.

32. The system of claim 19, wherein the first elongate strap support and at least one additional elongate strap support are of different sizes.

33. An elongate strap support system for anatomical support, pain reduction, or therapeutic treatment, the elongate strap support system comprising:
   a first elongate strap support including:
      a woven fabric support layer including fibers that are not natural fibers, wherein:
         the woven fabric support layer is pre-cut to form an elongate strap with rounded portions;
         the woven fabric support layer is substantially resistant to stretching in only one test direction specified in ASTM (American Society for Testing and Materials) D3759; and
         the woven fabric support layer has thickness that is less than 30 mils and a tensile strength that is greater than 10 lb/in-width in at least one direction;
      an adhesive layer on the woven fabric support layer for adhesive attachment of the woven fabric support layer to an outer skin surface of a body; and
      a removable cover layer on the adhesive layer;
   at least one additional elongate strap support; and
   a package containing the first elongate strap support and the at least one additional elongate strap support.

34. The elongate strap support system of claim 33, wherein the woven fabric support layer includes Rayon.

35. The elongate strap support system of claim 33, further comprising an antimicrobial.

36. The elongate strap support system of claim 33, wherein the first elongate strap support and one of the at least one additional elongate strap support are configured to be applied to the body in combination.

37. The elongate strap support system of claim 36, wherein the first elongate strap support and said one of the at least one additional elongate strap support are configured to intersect when applied to the body.

38. The elongate strap support system of claim 33, wherein the adhesive layer is intermittent across the support layer, such that permeability of the first elongate strap support is enhanced.

39. The elongate strap support system of claim 33, wherein the first elongate strap support and at least one additional elongate strap support are of different sizes.

40. An elongate strap support system for anatomical support, pain reduction, or therapeutic treatment, the elongate strap support system comprising:
   a first elongate strap support, including:
      a woven fabric support layer including synthetic fibers, wherein:
         the woven fabric support layer is shaped to form an elongated strap with rounded portions;

the woven fabric support layer is substantially resistant to stretching in only one test direction specified in ASTM (American Society for Testing and Materials) D3759; and an adhesive layer on the woven fabric support layer for adhesive attachment of the woven fabric support layer to an outer skin surface of a body; and a removable cover layer on the adhesive layer;

at least one additional elongate strap support; and a package containing the first elongate strap support and the at least one additional elongate strap support.

41. The elongate strap support system of claim 40, wherein the woven fabric support layer has a ratio of elongation in percent to tensile strength (lb/in-width) that is less than 0.9 in said one test direction, wherein elongation and tensile strength are determined in accordance with ASTM D3759.

42. The elongate strap support system of claim 40, wherein at least one of the elongate strap supports includes an arch strap configured for ease of application to the sole of a foot across the longitudinal axis of the sole in an arch area of the foot from a first side of a foot to the opposite side of the foot.

43. The elongate strap support system of claim 42, wherein the arch strap is configured to be applied to the foot, with at least one additional elongate strap support, such that the arch strap and the additional elongate strap intersect when applied to the foot.

44. The elongate strap support system of claim 40, wherein the first elongate strap support and one of the at least one additional elongate strap support are configured to be applied to the body in combination.

45. The elongate strap support system of claim 44, wherein the first elongate strap support is configured for use in conjunction with at least one additional elongate strap support such that when applied to the body the first elongate strap support and one additional strap support intersect.

46. The elongate strap support system of claim 40, wherein the woven fabric support layer is a microfiber fabric.

47. The elongate strap support system of claim 40, wherein the woven fabric support layer is fully synthetic.

48. The elongate strap support system of claim 40, wherein the adhesive layer is intermittent across the support layer, such that permeability of the first elongate strap support is enhanced.

49. The elongate strap support system of claim 40, wherein the first elongate strap support and at least one additional elongate strap support are of different sizes.

50. A system of anatomical supports, the system comprising:

a first elongate strap support, including:

a support layer of a woven fabric, wherein:

the woven fabric includes synthetic fibers and is shaped to form an elongate strap with straight portions and rounded portions;

the woven fabric has a thickness that is less than 30 mils and a tensile strength that is greater than 10 lb/in-width;

an adhesive layer on the support layer for adhesive attachment of the support layer to an outer skin surface of a body, wherein the adhesive layer is intermittent across the support layer; and a removable cover layer on the adhesive layer;

at least one additional elongate strap support; and a package containing the first elongate strap support and the at least one additional elongate strap support, wherein the synthetic fibers of the woven fabric and the intermittent adhesive layer allow the first elongate strap support to be breathable.

51. The system of claim 50, wherein the woven fabric is a fully synthetic fabric.

52. The system of claim 50, wherein the first elongate strap support and one of the at least one additional elongate strap support are configured to be applied to the body in combination.

53. The system of claim 52, wherein the first elongate strap support and said one of the at least one additional elongate strap support are configured to intersect when applied to the body.

54. The system of claim 50, wherein the woven fabric support layer is more stretch-resistant in a first test direction specified in ASTM (American Society for Testing and Materials) D3759 and less stretch-resistant in a second test direction specified in ASTM D3759.

55. The system of claim 50, wherein the first elongate strap support and at least one additional elongate strap support are of different sizes.

56. The system of claim 50, wherein the first elongate strap support and the at least one additional elongate strap support are formed in a roll in the package.

57. The system of claim 56, further comprising a center spool about which the roll is formed.

58. The system of claim 56, wherein the package includes a tube.

59. The system of claim 58, wherein the woven fabric includes only synthetic fibers.

60. The system of claim 58, wherein the package further includes a box.

61. The system of claim 50, wherein:

the system further comprises a center spool;

within the package, the first elongate strap support and the at least one additional elongate strap support are formed in a roll about the center spool;

the woven fabric includes only synthetic fibers; and the package includes a tube and a box.

62. A system of anatomical supports having enhanced breathability, the system comprising:

a first elongate strap support, including:

a support layer of a woven fabric, wherein:

the woven fabric includes synthetic fibers and is shaped in an elongate strap with straight portions and rounded portions;

the woven fabric has a thickness that is less than 30 mils and a tensile strength that is greater than 10 lb/in-width;

an adhesive layer on the support layer for adhesive attachment of the support layer to an outer skin surface of a body, wherein the adhesive layer is intermittent across the support layer; and a removable cover layer on the adhesive layer;

at least one additional elongate strap support; and a package containing the first elongate strap support and the at least one additional elongate strap support, wherein the synthetic fibers of the woven fabric and the intermittent adhesive layer allow the first elongate strap support to be breathable.

63. The system of claim 62, wherein the woven fabric is a microfiber fabric.

64. The system of claim 62, wherein the woven fabric is a breathable woven fabric.

65. The system of claim 62, wherein the woven fabric is a moisture-wicking woven fabric.

66. The system of claim 62, wherein the support layer has a moisture vapor transfer rate (MVTR) of at least 100 g/24 h/m².

\* \* \* \* \*